US010610096B2

(12) United States Patent
Scheibler et al.

(10) Patent No.: US 10,610,096 B2
(45) Date of Patent: Apr. 7, 2020

(54) MINIATURIZED MOBILE, LOW COST OPTICAL COHERENCE TOMOGRAPHY SYSTEM FOR HOME BASED OPHTHALMIC APPLICATIONS

(71) Applicant: Acucela Inc., Seattle, WA (US)

(72) Inventors: Lukas Scheibler, Telluride, CO (US); Matthias Pfister, Liebefeld-Bern (CH); Urban Schnell, Munchenbuchsee (CH); Stefan Troller, Sissach (CH); Ryo Kubota, Seattle, WA (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 15/996,329

(22) Filed: Jun. 1, 2018

(65) Prior Publication Data

US 2018/0271363 A1  Sep. 27, 2018

Related U.S. Application Data

(63) Continuation of application No. PCT/US2017/067603, filed on Dec. 20, 2017.
(Continued)

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/0008* (2013.01); *A61B 3/0025* (2013.01); *A61B 3/10* (2013.01);
(Continued)

(58) Field of Classification Search
CPC ....... A61B 3/102; A61B 5/0066; A61B 18/20; A61B 3/0025; A61B 2017/00508;
(Continued)

(56) References Cited

U.S. PATENT DOCUMENTS

| 6,053,613 A | 4/2000 | Wei et al. |
| 6,325,512 B1 | 12/2001 | Wei |

(Continued)

FOREIGN PATENT DOCUMENTS

| WO | 2015116981 A1 | 8/2015 |
| WO | 2015120055 A1 | 8/2015 |

(Continued)

OTHER PUBLICATIONS

Moon, "VCSEL-based swept source for low-cost optical coherence tomography", Biomedical Optics Express, Feb. 1, 2017, pp. 1110-1121, vol. 8, No. 2.
(Continued)

*Primary Examiner* — Brandi N Thomas
(74) *Attorney, Agent, or Firm* — Fisherbroyles LLP; John Shimmick

(57) ABSTRACT

Improved optical coherence tomography systems and methods to measure thickness of the retina are presented. The systems may be compact, handheld, provide in-home monitoring, allow the patient to measure himself or herself, and be robust enough to be dropped while still measuring the retina reliably.

23 Claims, 60 Drawing Sheets

Related U.S. Application Data

(60) Provisional application No. 62/547,314, filed on Aug. 18, 2017, provisional application No. 62/546,935, filed on Aug. 17, 2017, provisional application No. 62/539,382, filed on Jul. 31, 2017, provisional application No. 62/437,486, filed on Dec. 21, 2016.

(51) Int. Cl.
  *A61B 3/00* (2006.01)
  *A61B 3/12* (2006.01)
  *A61B 5/00* (2006.01)
  *G01B 9/02* (2006.01)

(52) U.S. Cl.
  CPC .......... *A61B 3/1005* (2013.01); *A61B 3/1225* (2013.01); *A61B 5/0013* (2013.01); *G01B 9/02* (2013.01); *A61B 2505/07* (2013.01); *A61B 2560/0425* (2013.01); *A61B 2560/0431* (2013.01); *A61B 2560/0456* (2013.01); *A61B 2576/00* (2013.01)

(58) Field of Classification Search
  CPC .... A61B 2018/1807; A61B 2018/2065; A61B 3/101; A61B 1/00188; A61B 3/113; A61B 5/00; A61B 5/0071; A61B 5/165; A61B 1/00096; A61B 1/00172; A61B 1/043; A61B 5/0068; A61B 5/444; A61B 8/0808; A61B 8/10; A61B 8/4461
  USPC ........ 351/200, 205–206, 209–211, 221–222, 351/243–246
  See application file for complete search history.

(56) References Cited

U.S. PATENT DOCUMENTS

| | | |
|---|---|---|
| 6,362,919 B1 | 3/2002 | Flanders |
| 6,409,395 B1 | 6/2002 | Wang et al. |
| 6,419,360 B1 | 7/2002 | Hauger et al. |
| 6,445,944 B1 | 9/2002 | Ostrovsky |
| 6,552,796 B2 | 4/2003 | Magnin et al. |
| 6,726,325 B2 | 4/2004 | Xie et al. |
| 6,736,508 B2 | 5/2004 | Xie et al. |
| 6,769,769 B2 | 8/2004 | Podoleanu et al. |
| 6,778,307 B2 | 8/2004 | Clark |
| 7,113,818 B2 | 9/2006 | Podoleanu et al. |
| 7,126,693 B2 | 10/2006 | Everett et al. |
| 7,140,730 B2 | 11/2006 | Wei et al. |
| 7,301,644 B2 | 11/2007 | Knighton et al. |
| 7,324,569 B2 | 1/2008 | Flanders et al. |
| 7,347,548 B2 | 3/2008 | Huang et al. |
| 7,375,818 B2 | 5/2008 | Kawahara |
| 7,391,520 B2 | 6/2008 | Zhou et al. |
| 7,452,077 B2 | 11/2008 | Meyer et al. |
| 7,482,589 B2 | 1/2009 | Flanders et al. |
| 7,542,145 B2 | 6/2009 | Toida et al. |
| 7,594,730 B2 | 9/2009 | Podoleanu |
| 7,602,500 B2 | 10/2009 | Izatt et al. |
| 7,633,623 B2 | 12/2009 | Hatori |
| 7,633,627 B2 | 12/2009 | Choma et al. |
| 7,701,585 B2 | 4/2010 | Hatori |
| 7,761,139 B2 | 7/2010 | Tearney et al. |
| 7,783,337 B2 | 8/2010 | Feldman et al. |
| 7,864,335 B2 | 1/2011 | Terakawa et al. |
| 7,872,759 B2 | 1/2011 | Tearney et al. |
| 7,929,148 B2 | 4/2011 | Kemp |
| 7,954,947 B2 | 6/2011 | Sugita et al. |
| 7,971,999 B2 | 7/2011 | Zinser |
| 7,980,694 B2 | 7/2011 | Keating et al. |
| 7,980,696 B1 | 7/2011 | Taki et al. |
| 7,997,728 B2 | 8/2011 | Huang et al. |
| 7,997,729 B2 | 8/2011 | McLean et al. |
| 8,025,403 B2 | 9/2011 | Maloca et al. |
| 8,049,900 B2 | 11/2011 | Kemp et al. |
| 8,055,107 B2 | 11/2011 | Masuda |
| 8,079,711 B2 | 12/2011 | Stetson et al. |
| 8,123,354 B2 | 2/2012 | Olivier et al. |
| 8,139,226 B2 | 3/2012 | Johnson |
| 8,192,024 B2 | 6/2012 | Yumikake et al. |
| 8,205,991 B2 | 6/2012 | Wei et al. |
| 8,220,924 B2 | 7/2012 | Hanebuchi et al. |
| 8,251,510 B2 | 8/2012 | Kobayashi et al. |
| 8,251,511 B2 | 8/2012 | Stetson et al. |
| 8,282,211 B2 | 10/2012 | Campbell et al. |
| 8,289,522 B2 | 10/2012 | Tearney et al. |
| 8,348,427 B2 | 1/2013 | Buckland et al. |
| 8,348,429 B2 | 1/2013 | Walsh et al. |
| 8,351,665 B2 | 1/2013 | Tearney et al. |
| 8,403,481 B2 | 3/2013 | Izatt et al. |
| 8,405,834 B2 | 3/2013 | Srinivasan et al. |
| 8,421,855 B2 | 4/2013 | Buckland et al. |
| 8,425,037 B2 | 4/2013 | Uhlhorn et al. |
| 8,442,284 B2 | 5/2013 | Rogers et al. |
| 8,446,593 B1 | 5/2013 | Ellerbee |
| 8,457,440 B1 | 6/2013 | Johnson |
| 8,467,051 B2 | 6/2013 | Flanders et al. |
| 8,474,978 B2 | 7/2013 | Huang et al. |
| 8,500,279 B2 | 8/2013 | Everett et al. |
| 8,526,006 B2 | 9/2013 | Nebosis et al. |
| 8,529,062 B2 | 9/2013 | Buckland et al. |
| 8,594,757 B2 | 11/2013 | Boppart et al. |
| 8,608,314 B2 | 12/2013 | Yoon et al. |
| 8,630,697 B2 | 1/2014 | Meyer et al. |
| 8,665,450 B2 | 3/2014 | Johnson et al. |
| 8,711,366 B2 | 4/2014 | Everett et al. |
| 8,721,078 B2 | 5/2014 | Torii et al. |
| 8,724,870 B2 | 5/2014 | Sekine et al. |
| 8,757,803 B2 | 6/2014 | Everett et al. |
| 8,781,287 B2 | 7/2014 | Flanders et al. |
| 8,794,763 B2 | 8/2014 | Stetson et al. |
| 8,801,184 B2 | 8/2014 | Hacker et al. |
| 8,820,931 B2 | 9/2014 | Walsh et al. |
| 8,836,953 B2 | 9/2014 | Johnson |
| 8,870,376 B2 | 10/2014 | Hogan |
| 8,894,207 B2 | 11/2014 | Hee et al. |
| 8,913,248 B2 | 12/2014 | Sharma et al. |
| 8,922,782 B2 | 12/2014 | Flanders |
| 8,926,097 B2 | 1/2015 | Sakagawa |
| 8,939,582 B1 | 1/2015 | Spaide et al. |
| 8,947,648 B2 | 2/2015 | Swanson et al. |
| 8,953,167 B2 | 2/2015 | Johnson et al. |
| 8,971,360 B2 | 3/2015 | Lewandowski et al. |
| 8,992,018 B2 | 3/2015 | Makihira |
| 8,994,753 B2 | 3/2015 | Nakano et al. |
| 8,998,412 B2 | 4/2015 | Makihira |
| 9,016,862 B2 | 4/2015 | Carnevale |
| 9,025,160 B2 | 5/2015 | Moore et al. |
| 9,025,847 B2 | 5/2015 | Kitamura et al. |
| 9,033,504 B2 | 5/2015 | Everett et al. |
| 9,033,510 B2 | 5/2015 | Narasimha-Iyer et al. |
| 9,044,164 B2 | 6/2015 | Hacker et al. |
| 9,055,891 B2 | 6/2015 | Suehira et al. |
| 9,060,689 B2 | 6/2015 | Tearney et al. |
| 9,084,562 B2 | 7/2015 | Kakuma |
| 9,095,281 B2 | 8/2015 | Sharma et al. |
| 9,119,562 B2 | 9/2015 | Naba |
| 9,138,141 B2 | 9/2015 | Makihira et al. |
| 9,144,378 B2 | 9/2015 | Suehira |
| 9,149,182 B2 | 10/2015 | Walsh et al. |
| 9,161,690 B2 | 10/2015 | Tomatsu et al. |
| 9,163,929 B2 | 10/2015 | Lim et al. |
| 9,163,930 B2 | 10/2015 | Buckland et al. |
| 9,167,964 B2 | 10/2015 | Everett et al. |
| 9,171,367 B2 | 10/2015 | Iwase et al. |
| 9,176,319 B2 | 11/2015 | Bouma et al. |
| 9,178,330 B2 | 11/2015 | Oh et al. |
| 9,192,294 B2 | 11/2015 | Sharma et al. |
| 9,200,888 B2 | 12/2015 | Jaillon et al. |
| 9,217,707 B2 | 12/2015 | Bajraszewski et al. |
| 9,226,653 B2 | 1/2016 | Torii et al. |
| 9,226,660 B2 | 1/2016 | Boer et al. |
| 9,241,626 B2 | 1/2016 | Narasimha-Iyer et al. |
| 9,243,885 B2 | 1/2016 | Johnson et al. |

(56) References Cited

U.S. PATENT DOCUMENTS

| | | |
|---|---|---|
| 9,259,151 B2 | 2/2016 | Murase |
| 9,267,783 B1 | 2/2016 | Sharma et al. |
| 9,273,950 B2 | 3/2016 | Yazdanfar et al. |
| 9,291,446 B2 | 3/2016 | Schneider et al. |
| 9,310,182 B2 | 4/2016 | Goldberg et al. |
| 9,339,186 B2 | 5/2016 | Somani et al. |
| 9,354,038 B2 | 5/2016 | Yasuno et al. |
| 9,373,933 B2 | 6/2016 | Njegovec et al. |
| 9,375,158 B2 | 6/2016 | Vakoc et al. |
| 9,377,293 B2 | 6/2016 | Hauger et al. |
| 9,380,935 B2 | 7/2016 | Iwase et al. |
| 9,408,532 B2 | 8/2016 | Makihira |
| 9,427,147 B2 | 8/2016 | Lujan et al. |
| 9,427,150 B2 | 8/2016 | Muto et al. |
| 9,433,353 B2 | 9/2016 | Hanebuchi |
| 9,468,374 B2 | 10/2016 | Makihira |
| 9,492,077 B2 | 11/2016 | Ebersbach et al. |
| 9,492,079 B2 | 11/2016 | Walsh et al. |
| 9,526,412 B2 | 12/2016 | Yang et al. |
| 9,526,415 B2 | 12/2016 | Fukuma et al. |
| 9,526,425 B2 | 12/2016 | Feldman et al. |
| 9,532,713 B2 | 1/2017 | Levecq et al. |
| 9,545,199 B2 | 1/2017 | Wang et al. |
| 9,584,098 B2 | 2/2017 | Yamanari et al. |
| 9,612,105 B2 | 4/2017 | Kemp |
| 9,615,736 B2 | 4/2017 | Yamashita |
| 9,649,024 B2 | 5/2017 | Hacker et al. |
| 9,649,025 B2 | 5/2017 | Jeglorz et al. |
| 9,696,132 B2 | 7/2017 | Jayaraman et al. |
| 9,702,686 B2 | 7/2017 | Hattersley |
| 9,778,018 B2 | 10/2017 | Schmoll et al. |
| 9,778,020 B2 | 10/2017 | Tumlinson et al. |
| 9,784,559 B2 | 10/2017 | Huber et al. |
| 9,812,846 B2 | 11/2017 | Yun et al. |
| 9,915,520 B2 | 3/2018 | Cable et al. |
| 9,948,061 B2 | 4/2018 | Njegovec et al. |
| 9,977,184 B1 | 5/2018 | Wong et al. |
| 9,993,153 B2 | 6/2018 | Chong |
| 10,045,692 B2 | 8/2018 | Tumlinson et al. |
| 2006/0131488 A1 | 6/2006 | Thingbo et al. |
| 2007/0076217 A1 | 4/2007 | Baker et al. |
| 2007/0183643 A1* | 8/2007 | Jayaraman ............ A61B 3/102 382/131 |
| 2007/0230856 A1 | 10/2007 | Yamazaki |
| 2008/0181263 A1 | 7/2008 | Bouma et al. |
| 2008/0296480 A1 | 12/2008 | Haber et al. |
| 2010/0110376 A1 | 5/2010 | Everett et al. |
| 2010/0110377 A1 | 5/2010 | Maloca et al. |
| 2011/0299034 A1* | 12/2011 | Walsh ................. A61B 3/102 351/206 |
| 2012/0092616 A1 | 4/2012 | Peyman |
| 2012/0300216 A1 | 11/2012 | Johnson et al. |
| 2012/0327365 A1 | 12/2012 | Makihira |
| 2013/0010259 A1 | 1/2013 | Carnevale |
| 2013/0010302 A1 | 1/2013 | Sharma et al. |
| 2013/0250241 A1 | 9/2013 | Everett et al. |
| 2014/0028997 A1 | 1/2014 | Cable et al. |
| 2014/0121508 A1 | 5/2014 | Latimer et al. |
| 2014/0125987 A1 | 5/2014 | Flanders |
| 2014/0218745 A1 | 8/2014 | Hattersley |
| 2014/0268050 A1* | 9/2014 | Jayaraman ........ G01B 9/02004 351/206 |
| 2014/0285812 A1 | 9/2014 | Levitz |
| 2014/0307078 A1 | 10/2014 | Charles et al. |
| 2014/0307753 A1 | 10/2014 | Minneman et al. |
| 2014/0340689 A1 | 11/2014 | Namati et al. |
| 2015/0010031 A1* | 1/2015 | Makino ............... H01S 5/18311 372/45.01 |
| 2015/0055089 A1 | 2/2015 | Aono et al. |
| 2015/0062532 A1 | 3/2015 | Sharma et al. |
| 2015/0109579 A1 | 4/2015 | Orlowski et al. |
| 2015/0110376 A1* | 4/2015 | Gessner ............. A61B 3/102 382/131 |
| 2015/0216412 A1 | 8/2015 | Hillmann et al. |
| 2015/0327761 A1 | 11/2015 | Narasimha-Iyer et al. |
| 2015/0327762 A1 | 11/2015 | Isogai et al. |
| 2016/0000368 A1 | 1/2016 | Wang et al. |
| 2016/0007857 A1 | 1/2016 | Wang et al. |
| 2016/0025478 A1 | 1/2016 | Johnson et al. |
| 2016/0040977 A1 | 2/2016 | An et al. |
| 2016/0040978 A1 | 2/2016 | Boppart et al. |
| 2016/0081545 A1 | 3/2016 | Hauger et al. |
| 2016/0106310 A1 | 4/2016 | Moriguchi |
| 2016/0106312 A1 | 4/2016 | Moriguchi |
| 2016/0106314 A1 | 4/2016 | Everett et al. |
| 2016/0166143 A1 | 6/2016 | Goto |
| 2016/0206190 A1 | 7/2016 | Reisman et al. |
| 2016/0242638 A1 | 8/2016 | Durbin et al. |
| 2016/0252340 A1 | 9/2016 | Hollenbeck et al. |
| 2016/0321828 A1 | 11/2016 | Tachikawa |
| 2016/0338589 A1 | 11/2016 | Carrasco-Zevallos et al. |
| 2016/0367129 A1 | 12/2016 | Coelho et al. |
| 2016/0367132 A1 | 12/2016 | Yun et al. |
| 2017/0020387 A1 | 1/2017 | Fingler et al. |
| 2017/0049318 A1 | 2/2017 | Walsh et al. |
| 2017/0055829 A1 | 3/2017 | Tan et al. |
| 2017/0065169 A1 | 3/2017 | Fukasawa et al. |
| 2017/0102223 A1 | 4/2017 | Izatt et al. |
| 2017/0105618 A1 | 4/2017 | Schmoll et al. |
| 2017/0205223 A1 | 7/2017 | Cable et al. |
| 2017/0227350 A1 | 8/2017 | Sarunic et al. |
| 2017/0231489 A1 | 8/2017 | Fujimori |
| 2017/0241763 A1 | 8/2017 | Wang et al. |
| 2017/0268987 A1 | 9/2017 | Swanson |
| 2017/0276471 A1 | 9/2017 | Jiang et al. |
| 2017/0280993 A1 | 10/2017 | Fukuhara et al. |
| 2017/0311795 A1 | 11/2017 | Sumiya et al. |
| 2018/0031363 A1 | 2/2018 | Johnson et al. |
| 2018/0051978 A1 | 2/2018 | Flanders et al. |
| 2018/0125354 A1 | 5/2018 | Pulaski et al. |
| 2018/0135962 A1 | 5/2018 | Murata et al. |
| 2018/0156598 A1 | 6/2018 | Cable et al. |
| 2018/0157924 A1 | 6/2018 | Hogan |
| 2018/0168445 A1 | 6/2018 | Horn |
| 2018/0206716 A1 | 7/2018 | Chong |

FOREIGN PATENT DOCUMENTS

| | | |
|---|---|---|
| WO | 2016073840 A1 | 5/2016 |
| WO | 2016115387 A1 | 7/2016 |
| WO | 2016125474 A1 | 8/2016 |
| WO | 2016127140 A1 | 8/2016 |
| WO | 2016148569 A1 | 9/2016 |
| WO | 2016178298 A1 | 11/2016 |
| WO | 2016179431 A1 | 11/2016 |
| WO | 2016196463 A1 | 12/2016 |
| WO | 2016203245 A1 | 12/2016 |
| WO | 2017002379 A1 | 1/2017 |
| WO | 2017025583 A1 | 2/2017 |
| WO | 2017046225 A1 | 3/2017 |
| WO | 2017048832 A1 | 3/2017 |
| WO | 2017165793 A1 | 9/2017 |
| WO | 2017176301 A1 | 10/2017 |
| WO | 2017206929 A1 | 12/2017 |
| WO | 2017216242 A1 | 12/2017 |
| WO | 2018086173 A1 | 5/2018 |
| WO | 2018089682 A1 | 5/2018 |
| WO | 2018105549 A1 | 6/2018 |
| WO | 2018116128 A1 | 6/2018 |
| WO | 2018119077 A1 | 6/2018 |

OTHER PUBLICATIONS

Orr. Notal Vision—Home-Based Optical Coherence Tomograph (OCT). Slide deck (11 pgs.) (Nov. 9, 2017).
PCT/US2017/067603 International Search Report and Written Opinion dated Mar. 5, 2018.

* cited by examiner

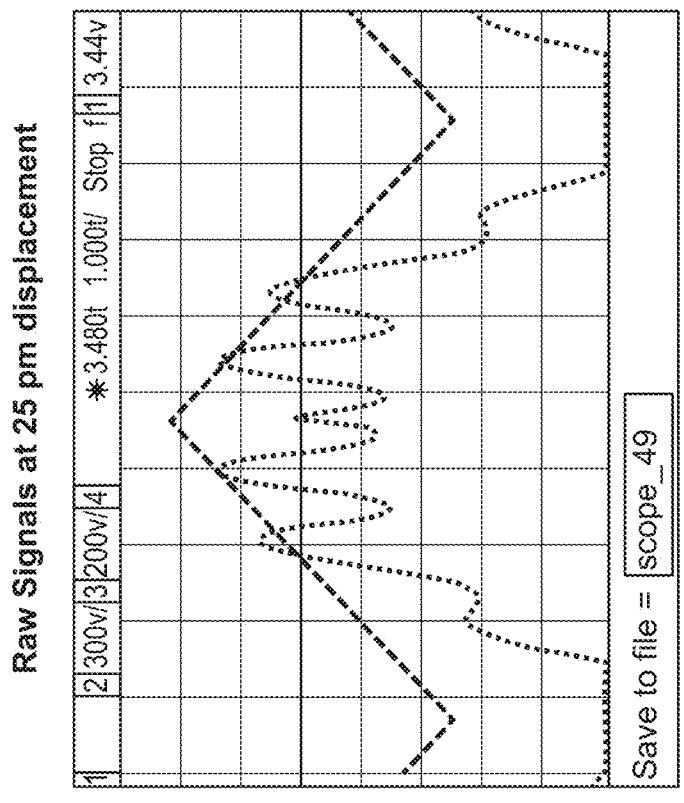
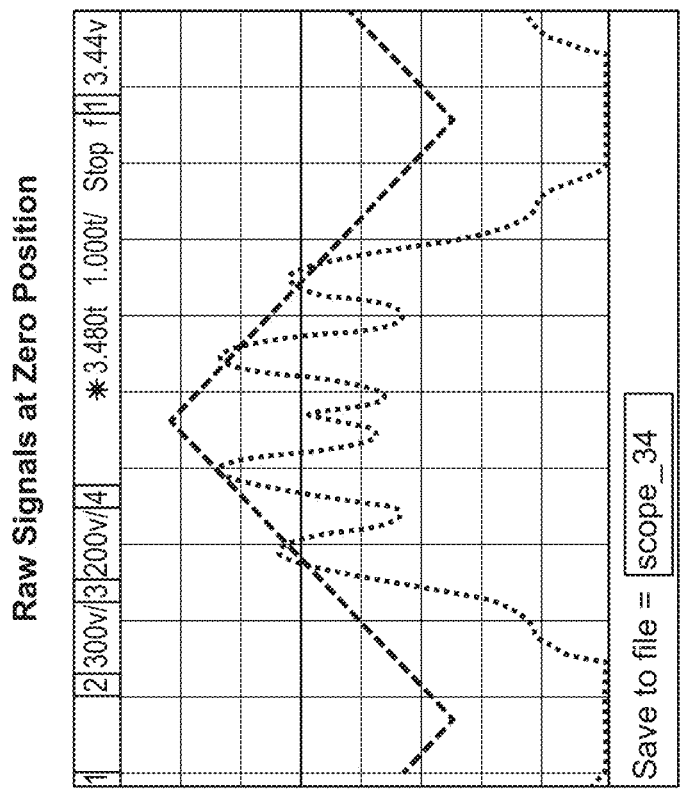
FIG. 16

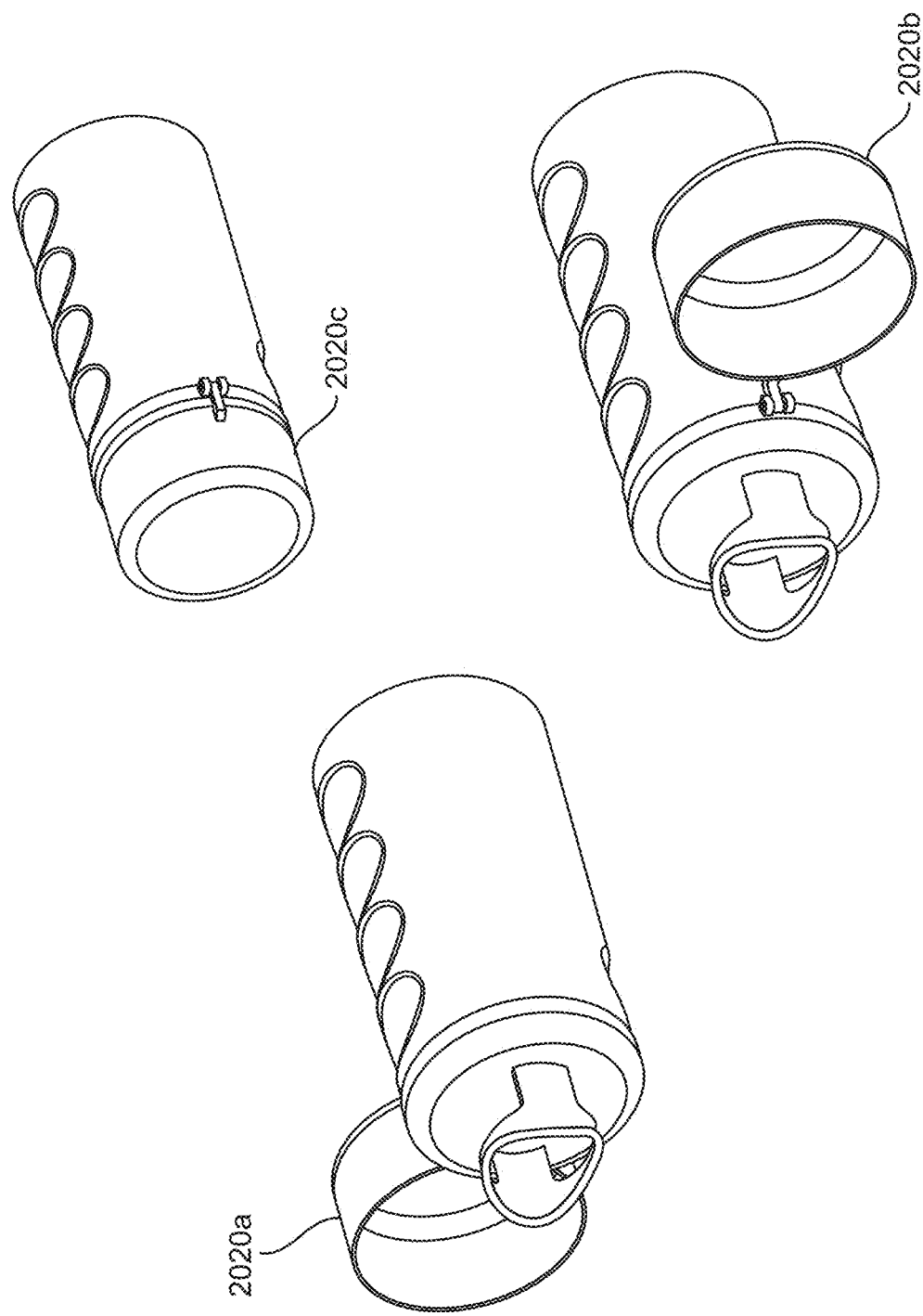

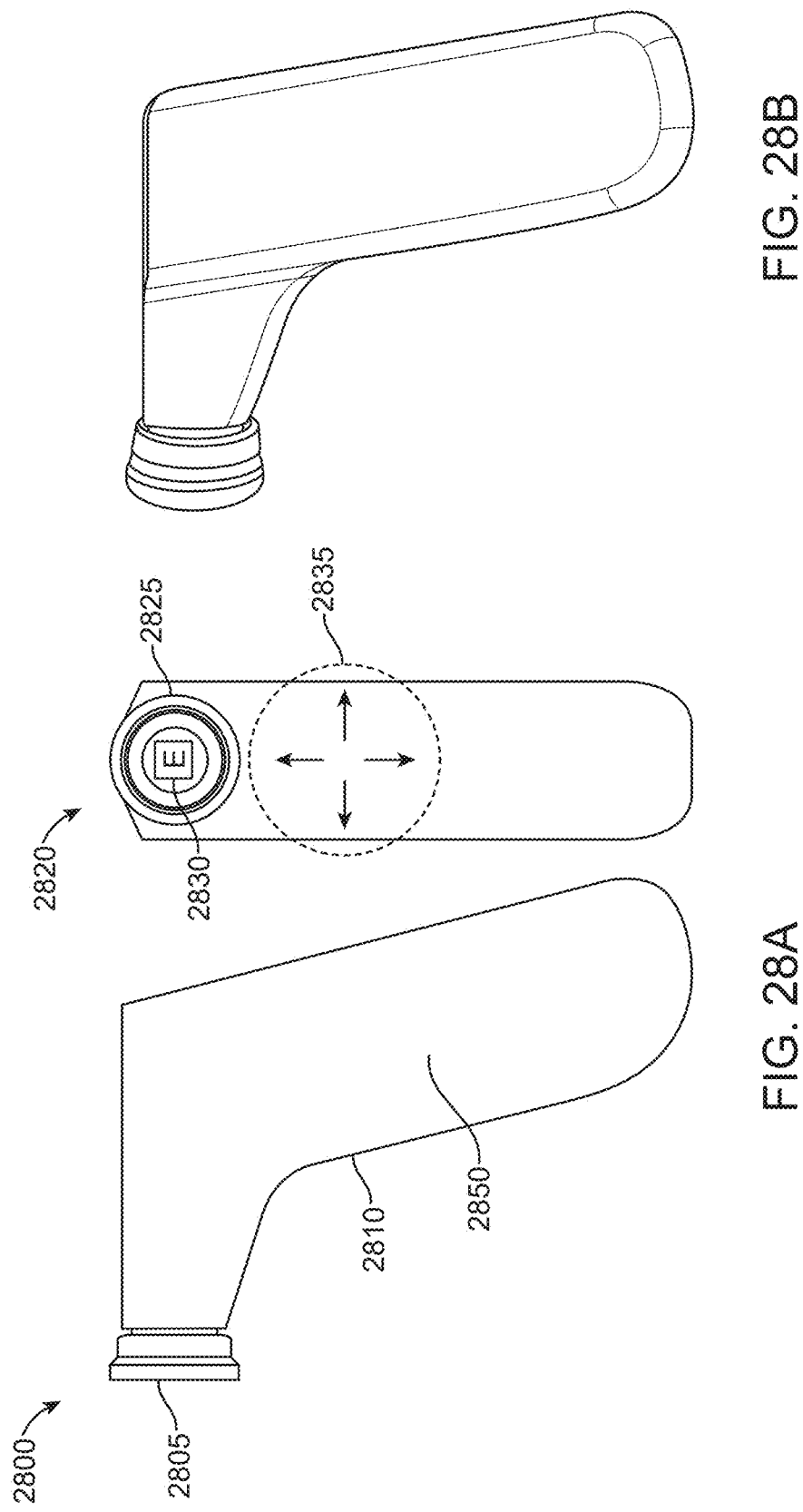

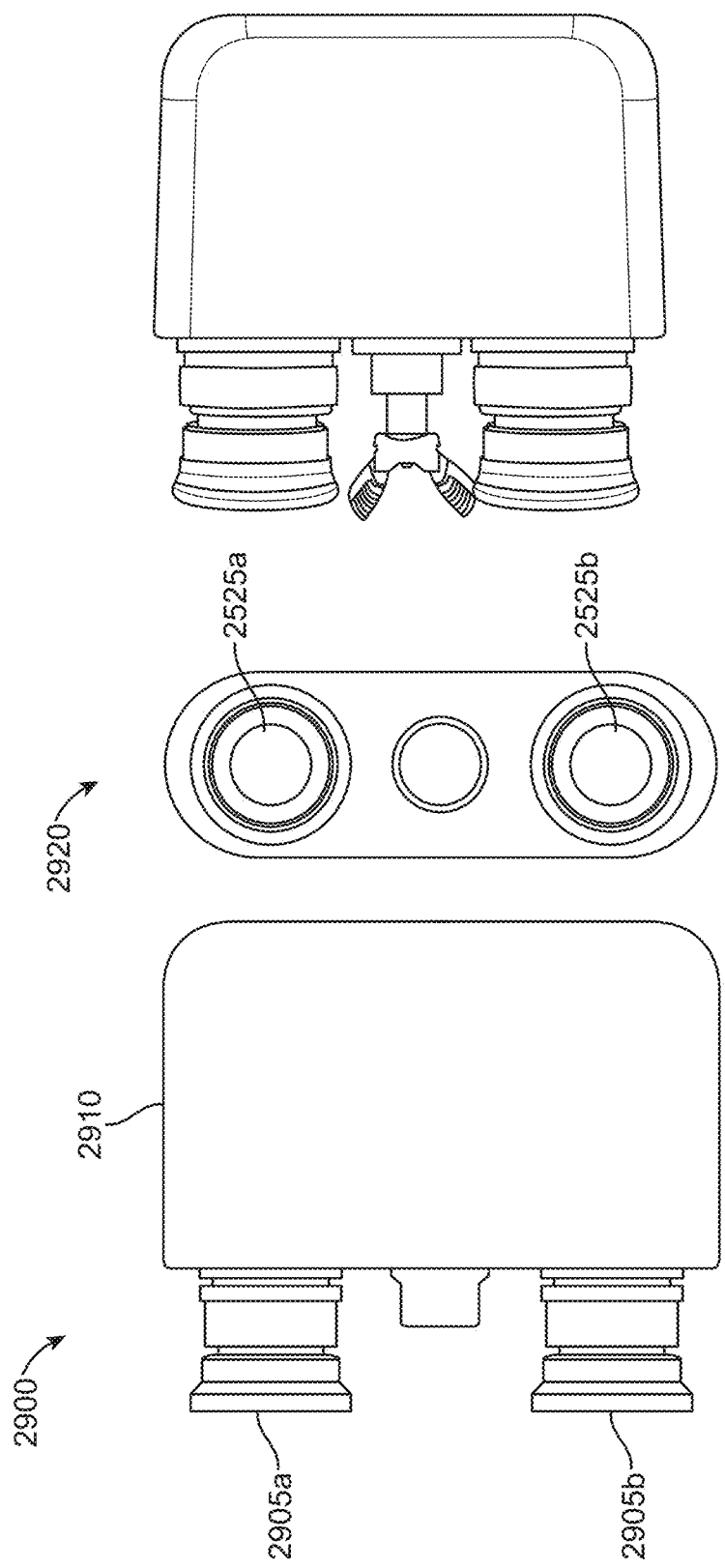

MINIATURIZED MOBILE, LOW COST OPTICAL COHERENCE TOMOGRAPHY SYSTEM FOR HOME BASED OPHTHALMIC APPLICATIONS

CROSS-REFERENCE

The present application is a continuation of International Application No. PCT/US17/67603, entitled "Miniaturized Mobile, Low Cost Optical Coherence Tomography System for Home Based Ophthalmic applications," filed Dec. 20, 2017; and claims priority to U.S. Provisional Application No. 62/437,486, entitled "Miniaturized Mobile, Low Cost Optical Coherence Tomography System for Home Based Ophthalmic Applications," filed Dec. 21, 2016; U.S. Provisional Application No. 62/539,382, entitled "Miniaturized Mobile, Low Cost Optical Coherence Tomography System for Home Based Ophthalmic Applications," filed Jul. 31, 2017; U.S. Provisional Application No. 62/546,935, entitled "Miniaturized Mobile, Low Cost Optical Coherence Tomography System for Home Based Ophthalmic Applications," filed Aug. 17, 2017; and U.S. Provisional Application No. 62/547,314, entitled "Miniaturized Mobile, Low Cost Optical Coherence Tomography System for Home Based Ophthalmic Applications," filed Aug. 18, 2017, which applications are incorporated herein by reference in their entireties for all purposes.

BACKGROUND

The eye is critical for vision, and people need to see. The eye has a cornea and lens that refract light and form an image on the retina. The retina generates electrical signals in response to the image formed thereon, and these electrical signals are transmitted to the brain via the optic nerve. The fovea and macula of the retina have an increased density of cones in relation to other areas of the retina and provide crisp, sharp vision. Unfortunately, diseases of the retina can adversely affect vision even though other parts of the eye, such as the cornea and lens are healthy.

Retinal thickness can be used to diagnose and monitor the health of the retina. Many patients who have been diagnosed with retinal vascular diseases and other diseases or conditions have an elevated retinal thickness and take or are treated with medications. Macular edema is an example of elevated retinal thickness which is often related to other diseases such as diabetes. Macular edema can be related to other diseases such as age related macular degeneration, uveitis, blockage of retinal vasculature, and glaucoma, for example. It would be helpful to know quickly if a medication is not working or requires re-administration so that treatment can be modified accordingly and vision preserved. One approach used to measure the thickness of the retina is optical coherence tomography (OCT).

Unfortunately, many prior OCT systems are overly complex and expensive and not well-suited to monitoring retinal thickness regularly, such as on a weekly or daily basis. The prior standard of eye care involves a visit to a health care provider who measures retinal thickness, but such visits require scheduling and appointments and can become expensive, especially if conducted on a weekly or daily basis. Many of the prior OCT systems are not well-suited for in-home monitoring or mobile health care. Such prior systems typically weigh more than a person can easily carry and are not-well suited to travel with the patient. In addition, the prior OCT systems are more complex than would be ideal, and not well-suited for everyday use and hazards such as being dropped. The prior cost of an OCT system may exceed what a typical patient can afford. Furthermore, use of a prior OCT system may require a trained operator. For the above reasons, in-home monitoring of retinal thickness has not been adopted as the prior standard of care and prior care of patients with retinal disease can be less than ideal in many instances.

In light of the above, it would be helpful to have improved OCT systems and methods to measure thickness of the retina. Ideally, such systems would be compact, handheld, provide in-home monitoring, allow the patient to measure himself or herself, and be robust enough to be dropped while still measuring the retina reliably.

SUMMARY

The compact optical coherence tomography (OCT) system and methods disclosed herein allow in-home and mobile monitoring of retinal thickness. Although specific reference is made to measuring retinal thickness, the compact OCT system and methods disclosed herein will find application in many fields, such as microscopy, metrology, aerospace, astronomy, telecommunications, medicine, pharmaceuticals, dermatology, dentistry, and cardiology.

The compact OCT system comprises a plurality of components arranged to provide a decreased optical path and weight. In many embodiments, the compact OCT system is configured to measure changes in retinal thickness that are less than a resolution value of the OCT system, which allows the size, cost and complexity to be decreased significantly. The system comprises sufficient repeatability and reproducibility to accurately detect changes in retinal thickness smaller than the system axial resolution value. The compact OCT system is capable of scanning the wavelength range and acquiring OCT data with sufficient speed in order to decrease errors associated with movement of the system in relation to the eye. In many embodiments, the compact OCT system is calibrated for a specific patient with a clinical reference system having a higher resolution than the compact OCT system, and the compact OCT system is calibrated to the specific patient based on the retinal thickness measured with the clinical reference system. In some cases, the compact OCT system comprises a calibration kit or fixture, which allows the system to be tested to ensure that the repeatability and reproducibility remain within acceptable tolerances.

In some instances, the compact OCT system is configured to be held in the hand of user for the patient to measure himself or herself. Alternatively, the compact OCT system may be configured to be mounted to a table stand or to the head of the user. In some embodiments, the compact OCT system comprises a visible target for the patient to align himself or herself with the compact spectrometer while the patient holds the measurement components of the system with his hand. The compact OCT system comprises a housing to contain the measurement components, and the housing is sized, in some instances, such that the user can readily grasp the housing and lift the measurement components within the housing and align the OCT system with his eye. The compactness and decreased mass of the OCT system allows the system to be easily held in the hand of the patient and transported with the patient. In many embodiments, the tomography system comprises a maximum dimension across within a range from about 80 mm to about 160 mm, and a mass within a range from about 100 grams to about 500 grams. In many embodiments, the OCT system is configured without internal moving parts in order to increase the reliability of the system. The compact OCT system is optionally configured to be dropped from a distance of about one foot, and provide a change in measurement repeatability and accuracy of retinal thickness of no more than about 25 μm, for example.

In some embodiments, the compact OCT system comprises a light source configured to emit a plurality of wavelengths, a detector, optical elements arranged to generate an optical interference signal on the detector, and circuitry coupled to the detector and light source. In some embodiments, the light source comprises a light source configured to emit a light beam of varying wavelength in order to sweep the wavelength over a range of wavelengths. In some instances, the wavelengths are swept over a range from about 3 nm to 10 nm in order to measure the thickness of the retina. This range can provide decreased system complexity and cost with sufficient axial resolution, repeatability, and reproducibility to determine changes in retinal thickness by 25 μm or less, although longer wavelength sweeps can be used. In some embodiments, the sweeping range of the OCT system within a range from 3 nm to 10 nm allows detection of retinal thickness larger than about 150 μm and changes in retinal thickness as small as 25 μm, for example, with the compact OCT system, although longer wavelength sweeps can be used. The circuitry is configured, in some embodiments, to drive the light source with a waveform having a characteristic period and sweeping frequency, such as a saw tooth waveform. In some instances, the circuitry is coupled to the detector to measure frequencies of an interference signal from the light returned from eye to determine retinal thickness of the eye, although the thickness of other objects can be measured. In some embodiments, the circuitry is configured to drive the light source over a maximum rated current threshold for a portion of the waveform and below the maximum rated current threshold for another portion of the waveform, in which the light source emits light during both portions of the waveform. This overdriving of the light source within a portion of the waveform allows for an extended wavelength range of the light source and increased measurement range with decreased complexity, size, and weight of the OCT system.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 16 shows oscilloscope signals for two different configurations of the optical setup.

FIG. 20B shows a handheld OCT system adapted to measure a right eye or a left eye.

FIG. 28A and FIG. 28B show a configuration for a handheld monocular OCT system, in accordance with some embodiments;

FIG. 29A, FIG. 29B, and FIG. 29C show a configuration for an exemplary handheld binocular OCT system, in accordance with some embodiments;

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The compact OCT system disclosed herein is well-suited for use with many prior clinical tests, such as retinal thickness measurements. In some cases, the OCT system is used by the patient, or by a health care provider. In many instances the patient can align himself with the system, although another user can align the patient with the system and take the measurement. In some embodiments, the OCT system is integrated with prior software and systems to provide additional information to healthcare providers, and can provide alerts in response to changes in retinal thickness. The alerts are optionally sent to the patient, caregiver, and health care providers when corrective action should be taken such as a change in medication, dosage, or a reminder to take medication.

As used herein, the term "retinal thickness (RT)" refers to a thickness of the retina between layers used to evaluate the thickness of a retina of a patient. The RT may correspond to a thickness of the retina between an anterior surface of the retina and external limiting membrane, for example.

As used herein, the term "retinal layer thickness (RLT)" refers to the thickness of one or more optically detectable layers of the retina. The optically detectable layers of the retina may comprise a thickness of the retina extending between the external limiting membrane and the retinal pigment epithelium, for example.

As used herein, the term "high resolution" refers to a measurement system capable of optically resolving structures that are smaller in at least one linear dimension than structures that can be a resolved by a measurement system of lower resolution.

Figure 1:
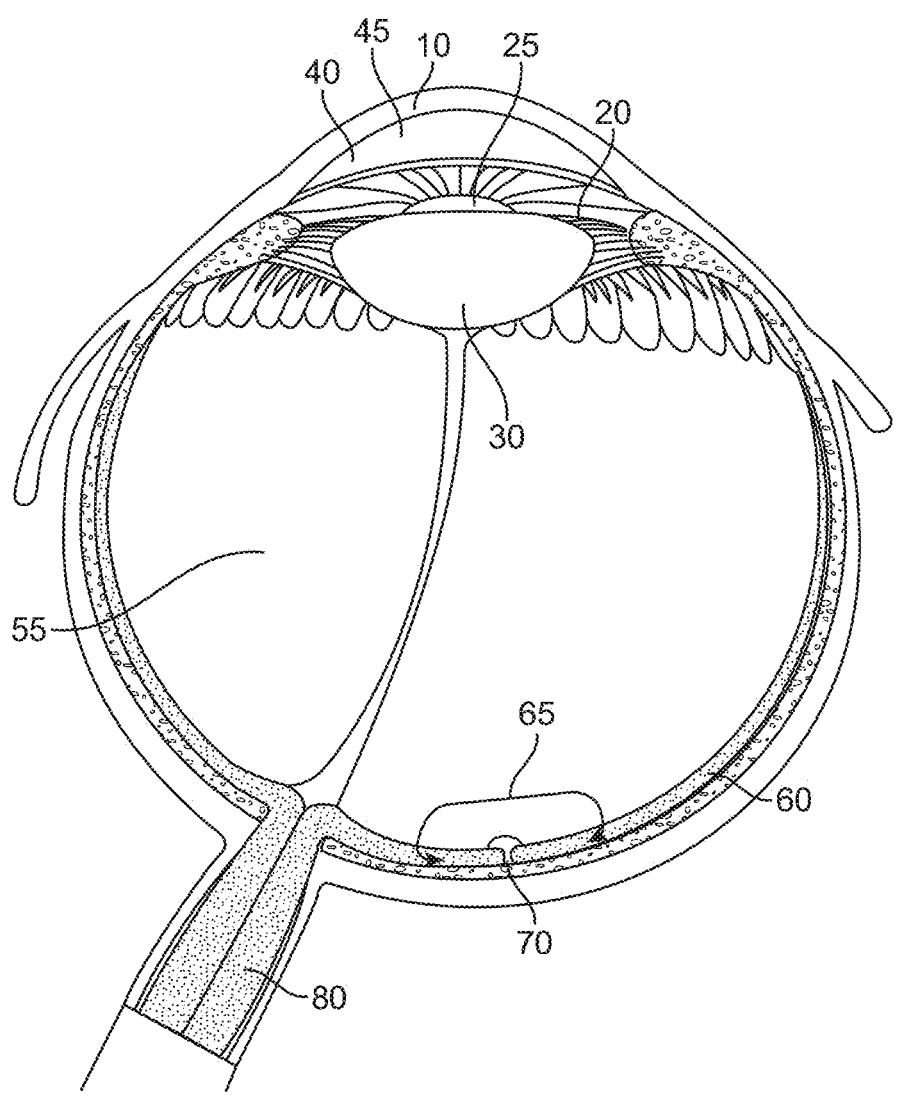
FIG. 1 shows a simplified diagram of the human eye.

FIG. 1 shows a simplified diagram of the human eye. Light enters the eye through the cornea 10. The iris 20 controls the amount of light allowed to pass by varying the size of the pupil 25 that allows light to proceed to the lens 30. The anterior chamber 40 contains aqueous humor 45 which determines the intraocular pressure (IOP). The lens 30 focuses light for imaging. The focal properties of the lens are controlled by muscles which reshape the lens. Focused light passes through the vitreous chamber 50, which is filled with vitreous humor 55. The vitreous humor maintains the overall shape and structure of the eye. Light then falls upon the retina 60, which has photosensitive regions. In particular, the macula 65 is the area of the retina responsible for receiving light in the center of the visual plane. Within the macula, the fovea 70 is the area of the retina most sensitive to light. Light falling on the retina generates electrical signals which are passed to the optic nerve 80 and then to the brain for processing.

Several disorders give rise to reduced optical performance of the eye. In some cases, the intraocular pressure (IOP) is either too high or too low. This is caused, for instance, by too high or too low of a production rate of aqueous humor in the anterior chamber. In other cases, the retina is too thin or too thick. This arises, for instance, due to the buildup of fluid in the retina. Diseases related to an abnormal retinal thickness (RT) include glaucoma and macular edema, for example. In some cases, a healthy range of RT is from 175 μm thick to 225 μm thick. In general, abnormalities in either the IOP or the RT are indicative of the presence of many ophthalmological diseases. Additionally, the IOP or the RT vary in response to ophthalmological treatments or other procedures. Therefore, it is desirable to have a means to measure the IOP and/or RT for diagnosis of ophthalmological diseases and to assess the effectiveness of treatments for a given patient. In some cases, it is desirable to measure the thickness of one or more retinal layers, for example the thickness of a plurality of layers.

The systems and methods disclosed herein relate to the use of optical coherence tomography (OCT) to measure the RT or RLT at multiple points in time. For instance, a patient measures their RT or RLT at multiple time points to track the progression of an ophthalmological disease such as glaucoma or macular edema over time. As another example, a patient measures their RT or RLT at multiple time points to track their response to a pharmaceutical or other treatment. In some cases, the system produces an alert when one or more recent measurements of the RT or RLT deviate significantly from previous measurements. In some cases, the system alerts the patient or the patient's physician of the change. In some instances, this information is be used to schedule a follow-up appointment between the patient and physician to, for instance, attempt a treatment of an ophthalmological illness, discontinue a prescribed treatment, or conduct additional testing.

Figure 2:
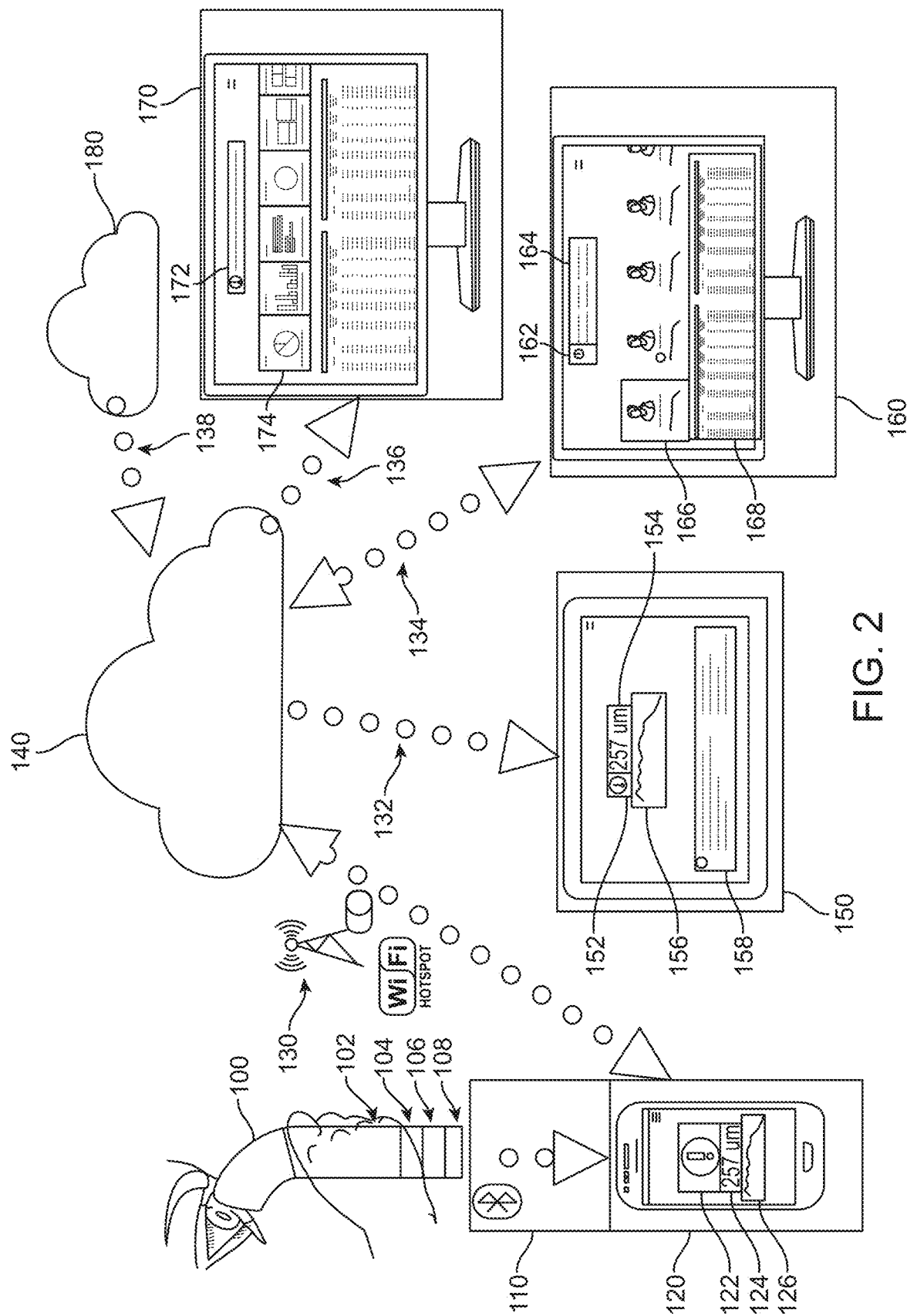
FIG. 2 shows a schematic of a system allowing a patient to measure retinal thickness (RT) at multiple time points and to communicate the results, in accordance with some embodiments.

FIG. 2 shows a schematic of a system allowing a patient to measure RT or RLT at multiple time points and to communicate the results, in accordance with some embodiments. The patient looks into a handheld OCT device 100 to obtain a measurement of the RT or RLT. In some embodiments, the handheld OCT device comprises optics 102, electronics 104 to control and communicate with the optics, a battery 106, and a transmitter 108. In some instances, the transmitter is a wired transmitter. In some cases, the transmitter is a wireless transmitter. In some cases, the handheld OCT device communicates the results via a wireless communication channel 110 to a mobile patient device 120 on the patient's smartphone or other portable electronic device. In some cases, the wireless communication is via Bluetooth communication. In some embodiments, the wireless communication is via Wi-Fi communication. In other embodiments, the wireless communication is via any other wireless communication known to one having skill in the art.

In some cases, the results are fully processed measurements of the RT. In some cases, all processing of the OCT data is performed on the handheld OCT device. For instance, in some embodiments, the handheld OCT device includes hardware or software elements that allow the OCT optical waveforms to be converted into electronic representations. In some cases, the handheld OCT device further includes hardware or software elements that allow processing of the electronic representations to extract, for instance, a measurement of the RT.

In some cases, the results are electronic representations of the raw optical waveforms obtained from the OCT measurement. For instance, in some embodiments, the handheld OCT device includes hardware or software elements that allow the OCT optical waveforms to be converted into electronic representations. In some cases, these electronic representations are then passed to the mobile patient device for further processing to extract, for instance, a measurement of the RT.

In some cases, the patient receives results and analysis of the RT or RLT measurement on the patient mobile app. In some embodiments, the results include an alert 122 alerting the patient that the results of the measurement fall outside of a normal or healthy range. In some cases, the results also include a display of the measured value 124. For instance, in some cases a measurement of the RT or RLT produces a result of 257 μm. In some instances, this result falls outside of a normal or healthy range. This causes the system to produce an alert and to display the measured value of 257 μm on the patient mobile app. In some embodiments, the results also include a chart 126 showing a history of the patient's RT or RLT over multiple points in time.

In some instances, the patient mobile device communicates the results of the measurement via a communication means 130 to a cloud-based or other network-based storage and communications system 140. In some embodiments, the communication means is a wired communication means. In some embodiments, the communication means is a wireless communication means. In some cases, the wireless communication is via Wi-Fi communication. In other cases, the wireless communication is via a cellular network. In still other cases, the wireless communication is via any other wireless communication known to one having skill in the art. In specific embodiments, the wireless communication means is configured to allow transmission to or reception from the cloud-based or other network-based storage and communications system.

Once stored in the cloud, the results are then transmitted to other devices, in specific embodiments. In some cases, the results are transmitted via a first communication channel 132 to a patient device 150 on the patient's computer, tablet, or other electronic device. In some embodiments, the results are transmitted via a second communication channel 134 to a physician device 160 on the patient's physician's computer, tablet, or other electronic device. In some instances, the results are transmitted via a third communication channel 136 to an analytics device 170 on another user's computer, tablet, or other electronic device. In some embodiments, the results are transmitted via a fourth communication channel 138 to a patient administration system or hospital administration system 180. In some cases, each of the devices has appropriate software instructions to perform the associate function as described herein.

In specific embodiments, the first communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is via any other wired or wireless communication known to one having skill in the art. In some embodiments, the first communication channel is configured to allow transmission to or reception from the cloud-based or other network-based storage and communications system. In some cases, the first communication channel is configured to only allow reception from the cloud-based or other network-based storage and communications system.

In some cases, the second communication channel is a wired communication channel or a wireless communication channel. In some instances, the communication is via Ethernet. In specific embodiments, the communication is via a local area network (LAN) or wide area network (WAN). In other embodiments, the communication is via Wi-Fi. In still other embodiments, the communication is via any other wired or wireless communication known to one having skill in the art. In some cases, the second communication channel is configured to allow transmission to or reception from the cloud-based or other network-based storage and communications system. In some embodiments, the second communication channel is configured to only allow reception from the cloud-based or other network-based storage and communications system.

In specific cases, the third communication channel is a wired communication channel or a wireless communication channel. In some instances, the communication is via Ethernet. In other instances, the communication is via a local area network (LAN) or wide area network (WAN). In still other instances, the communication is via Wi-Fi. In yet other instances, the communication is via any other wired or wireless communication known to one having skill in the art. In some embodiments, the third communication channel is configured to allow transmission to or reception from the cloud-based or other network-based storage and communications system. In some cases, the third communication channel is configured to only allow reception from the cloud-based or other network-based storage and communications system.

In some embodiments, the fourth communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is any other wired or wireless communication known to one having skill in the art. In some instances, the fourth communication channel is configured to allow transmission to or reception from the cloud-based or other network-based storage and communications system. In other cases, the fourth communication channel is configured to only allow reception from the cloud-based or other network-based storage and communications system.

A determination of the RT or RLT can be performed at many locations. For instance, a determination of the RT or RLT is performed on the handheld OCT device. In some cases, a determination of the RT or RLT is performed at a location near to the handheld OCT device, such as by a smartphone or other portable electronic device. In some embodiments, a determination of the RT or RLT is performed on the cloud-based storage and communications system. In some instances, he handheld OCT device is configured to compress measurement data and transmit the compressed measurement data to the cloud-based storage and communications system.

In some embodiments, the patient receives results and analysis of the RT or RLT measurement on the patient device 150. In some instances, the results include an alert 152 alerting the patient that the results of the measurement fall outside of a normal or healthy range. In some cases, the results also include a display of the measured value 154. For instance, in some cases, a measurement of the RT or RLT produces a result of 257 µm. This result falls outside of a normal or healthy range. In some cases, this causes the system to produce an alert and to display the measured value of 257 µm on the patient app. In specific cases, the results also include a chart 156 showing a history of the patient's RT or RLT over multiple points in time. In some cases, the patient device also displays instructions 158 for the patient to follow. In some instances, the instructions instruct the patient to visit their physician. In some embodiments, the instructions include the patient's name, date of most recent RT or RLT measurement, and next scheduled visit to their physician. In other cases, the instructions include more information. In still other cases, the instructions include less information.

In some embodiments, the patient's physician receives the results and analysis of the RT or RLT measurement on the physician device 160. In some instances, the results include an alert 162 alerting the physician that the results of the measurement fall outside of a normal or healthy range. In some cases, the results also include an alert 164 informing the physician that the patient's measurement falls outside of a normal or healthy range. In some embodiments, the alert includes a suggestion that the physician call the patient to schedule an appointment or to provide medical assistance. In some embodiments, the results also include a display 166 showing the most recent measurements and historical measurements for each of the physician's patients. For instance, in some instances, a measurement of the RT or RLT produces a result of 257 µm. This result falls outside of a normal or healthy range. In some cases, this causes the system to produce an alert and to display the measured value of 257 µm on the physician app. In specific cases, the physician device also displays contact and historical information 168 for each of the physician's patients.

In some embodiments, the other user receives results and analysis of the RT or RLT measurement on the analytics device 170. In some instances, the other user is a researcher investigating the efficacy of a new form of treatment. In other cases, the other user is an auditor monitoring the outcomes of a particular physician or care facility. To protect the patient's privacy, in some cases the analytics device is restricted to receive only a subset of a given patient's information. For instance, the subset is restricted so as not to include any personally identifying information about a given patient. In some cases, the results include an alert 172 alerting that a large number of abnormal or unhealthy measurements have been obtained in a specific period of time. In some cases, the results include one or more graphical representations 174 of the measurements across a population of patients.

In some cases, the results and analysis on the analytics device comprise disease information such as a physician-confirmed diagnosis. In some cases, the results and analysis comprise anonymized patient data such as age, gender, genetic information, information about the patient's environment, smoking history, other diseases suffered by the patient, etc. In some cases, the results and analysis comprise anonymized treatment plans for the patient, such as a list of prescribed medications, treatment history, etc. In some cases, the results and analysis comprise measurement results, such as the results of an RT or RLT measurement, a visual function test, or the patient's compliance with a course of treatment. In some cases, the results and analysis comprise data from an electronic medical record. In some cases, the results and analysis comprise diagnostic information from visits to a patient's medical provider, such as the results of an OCT scan acquired by the patient's medical provider.

In some embodiments, the patient's clinical, hospital, or other health provider receives results and analysis of the RT or RLT measurement on the patient administration system or hospital administration system 180. In some cases, this system contains the patient's electronic medical record. In some cases, the results and analysis provide the patient's health provider with data allowing the provider to update the treatment plan for the patient. In some instances, the results and analysis allow the provider to decide to call the patient in for an early office visit. In some instances, the results and analysis allow the provider to decide to postpone an office visit.

In some embodiments, one or more of the patient device, physician device, and analytics device includes a software app comprising instructions to perform the functions of the patient device, physician device, or analytics device, respectively, as described herein.

Figure 3A:
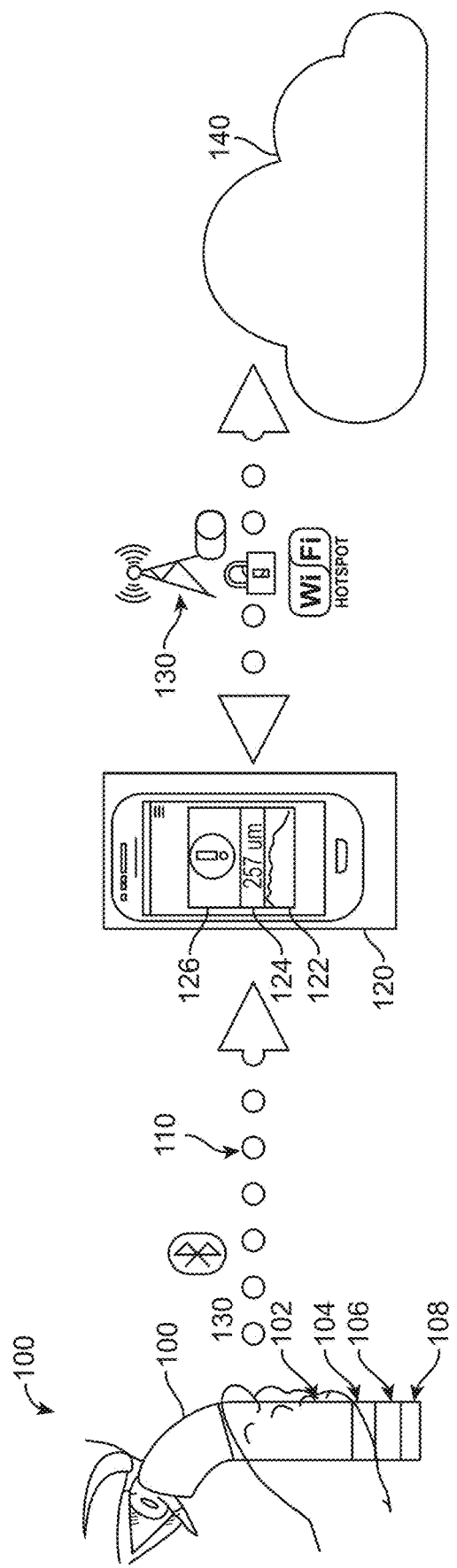
FIG. 3A shows a handheld optical coherence tomography (OCT) device utilizing Bluetooth communication, in accordance with some embodiments.

FIG. 3A shows a handheld OCT device utilizing short-range wireless communication, in accordance with some embodiments. In some embodiments, the handheld OCT device 100 comprises optics 102, electronics to control and communicate with the optics 104, a battery 106, and a wireless transmitter 108. In some cases, the wireless transmitter is a Bluetooth transmitter. In some instances, the results from one or more RT or RLT measurements are stored on the handheld OCT device until an authorized user, such as the patient or another person designated by the patient, opens the patient mobile device on a smartphone or other portable electronic device. Once opened, the patient mobile device establishes wireless communication with the handheld OCT device. In some cases, the communication is via a Bluetooth wireless communication channel 110. In some instances, the handheld OCT device communicates the results via the Bluetooth channel to a mobile patient device 120 on the patient's smartphone or other portable electronic device.

In some instances, the results include an alert 122 alerting the patient that the results of the measurement fall outside of a normal or healthy range. In specific embodiments, the results also include a display of the measured value 124. For instance, a measurement of the RT or RLT produces a result of 257 μm in some cases. This result falls outside of a normal or healthy range. In some cases, this causes the system to produce an alert and to display the measured value of 257 μm on the patient mobile app. In specific embodiments, the results also include a chart 126 showing a history of the patient's RT or RLT over multiple points in time.

In some cases, the patient mobile device communicates the results of the measurement via a wireless communication means 130 to a cloud-based or other network-based storage and communications system 140. In some instances, the wireless communication is via Wi-Fi communication. In other cases, the Wi-Fi communication is via a secure Wi-Fi channel. In still other cases, the wireless communication is via a cellular network. In specific embodiments, the cellular network is a secure cellular network. In other embodiments, the transmitted information is encrypted. In some cases, the communication channel is configured to allow transmission to or reception from the cloud-based or other network-based storage and communications system. In some cases, data is stored on the smartphone or other portable electronic device until the smartphone or other portable electronic device connects to a Wi-Fi or cellular network.

In some cases, the patient mobile device has a feature which notifies the patient or another person designated by the patient when too much time has elapsed since the patient mobile device was last opened. For instance, in some cases this notification occurs because the patient has not acquired measurements of the RT or RLT as recently as required by measuring schedule set by their physician or other healthcare provider. In other cases, the notification occurs because the handheld OCT device has been storing the results of too many measurements and needs to transmit the data to the patient's smartphone. In specific embodiments, the patient mobile device communicates with the cloud-based or other network-based storage and communications system to display a complete set of patient data.

Figure 3B:
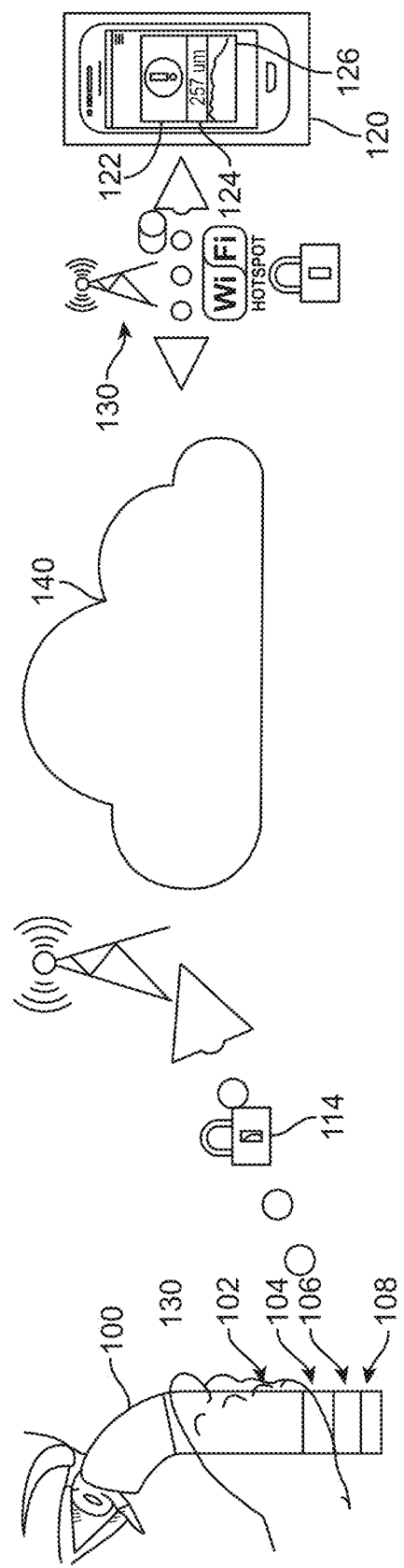
FIG. 3B shows a handheld OCT device utilizing the Global System for Mobile Communications (GSM), in accordance with some embodiments.

FIG. 3B shows a handheld OCT device capable of communicating directly with a cloud-based storage and communication system without reliance on a user device such as a smartphone, in accordance with some embodiments. In some embodiments, the handheld OCT device 100 comprises optics 102, electronics to control and communicate with the optics 104, a battery 106, and a wireless transmitter 108. In some cases, the wireless transmitter is a GSM transmitter. In some instances, the results from one or more RT or RLT measurements are stored on the handheld OCT device. In some cases, the GSM transmitter establishes wireless communication with a cloud-based or other network-based storage and communications system 140 via a wireless communication channel 114. In specific cases, the wireless communication is via a GSM wireless communication channel. In other embodiments, the system utilizes third generation (3G) or fourth generation (4G) mobile communications standards. In such cases, the wireless communication is via a 3G or 4G communication channel.

In specific embodiments, the patient mobile device 120 receives the results of the measurement via a wireless communication means 130 from the cloud-based or other network-based storage and communications system 140. In some cases, the wireless communication is via Wi-Fi communication. In some cases, the Wi-Fi communication is via a secure Wi-Fi channel. In other cases, the wireless communication is via a cellular network. In some cases, the cellular network is a secure cellular network. In specific instances, the transmitted information is encrypted. In some embodiments, the communication channel is configured to allow transmission to or reception from the cloud-based or other network-based storage and communications system.

Once obtained from the cloud-based or other network-based storage and communications system, the results of the RT or RLT measurement are viewed in the patient mobile app, in some instances. In some cases, the results include an alert 122 alerting the patient that the results of the measurement fall outside of a normal or healthy range. In some instances, the results also include a display of the measured value 124. For instance, in some cases a measurement of the RT or RLT produces a result of 257 μm. This result falls outside of a normal or healthy range. In specific embodiments, this causes the system to produce an alert and to display the measured value of 257 µm on the patient mobile app. In some embodiments, the results also include a chart 126 showing a history of the patient's RT or RLT over multiple points in time.

In some cases, the patient mobile device has a feature which notifies the patient or another person designated by the patient when too much time has elapsed since the patient mobile device was last opened. For instance, in some cases this notification occurs because the patient has not acquired measurements of the RT or RLT as recently as required by measuring schedule set by their physician or other healthcare provider. In other cases, the notification occurs because the handheld OCT device has been storing the results of too many measurements and needs to transmit the data to the patient's smartphone. In specific embodiments, the patient mobile device communicates with the cloud-based or other network-based storage and communications system to display a complete set of patient data.

In some cases, the handheld OCT device comprises both a short-range transmitter and a GSM, 3G, or 4G transmitter. In some instances, the short-range transmitter is a Bluetooth transmitter. In some cases, the handheld OCT device communicates directly with the patient mobile device on a smartphone or other portable electronic device through the Bluetooth wireless communication channel. In some embodiments, the handheld OCT also communicates with the cloud-based or other network-based storage and communications system through the GSM, 3G, or 4G wireless communication channel. In specific cases, the cloud-based system then communicates with the patient mobile device through a Wi-Fi, cellular, or other wireless communication channel. Alternatively, the Bluetooth transmitter is built into a docking station. In some instances, this allows for the use of older devices for patients who lack a smartphone. In some cases, the docking station also includes a means for charging the battery of the handheld OCT device.

In some cases, the handheld OCT device of FIGS. 3A and 3B is configured to be held in close proximity to the eye. For instance, in specific embodiments, the device is configured to be held in front of the eye with the detector at a distance of no more than 200 mm from the eye. In other embodiments, the devices are configured to be held in front of the eye with the detector at a distance of no more than 150 mm, no more than 100 mm, or no more than 50 mm from the eye. In specific instances, the handheld OCT devices further comprise housing to support the light source, optical elements, detector, and circuitry. In some cases, the housing is configured to be held in a hand of a user. In some cases, the user holds the devices in front of the eye to direct the light beam into the eye. In some instances, the devices include a sensor to measure which eye is being measured. For instance, in specific embodiments, the devices include an accelerometer or gyroscope to determine which eye is measured in response to an orientation of the housing. The devices optionally include an occlusion structure coupled to the housing and the sensor that determines which eye is measured. The occlusion structure occludes one eye while the other eye is measured. In some cases, the devices include a viewing target to align the light beams with a portion of the retina. For instance, in specific embodiments, the devices include a viewing target to align the light beams with a fovea of the eye. In some cases, the viewing target is a light beam. In some cases, the viewing target is a light emitting diode. In other cases, the viewing target is a vertical cavity surface emitting laser (VCSEL). In still further cases, the viewing target is any viewing target known to one having skill in the art.

The optical components described herein are capable of being miniaturized so as to provide the handheld OCT device with a reduced physical size and mass, as described herein, as will be appreciated by one of ordinary skill in the art.

In many embodiments, the handheld OCT devices of FIGS. 3A and 3B are small enough and light enough to be easily manipulated with one hand by a user. For instance, in many embodiments, the device has a mass within a range from about 100 grams to about 500 grams. In many embodiments, the device has a mass within a range from about 200 grams to about 400 grams. In many embodiments, the device has a mass within a range from about 250 grams to about 350 grams. In specific embodiments, the device has a maximum distance across within a range from about 80 mm to about 160 mm. In specific embodiments, the device has a maximum distance across within a range from about 100 mm to about 140 mm. In specific embodiments, the device has a width within a range from about 110 mm to about 130 mm. In some embodiments, the maximum distance across comprises a length. In some embodiments, the device has a width less than its length. In specific embodiments, the device has a width within a range from about 40 mm to about 80 mm. In specific embodiments, the device has a width within a range from about 50 mm to about 70 mm. In specific embodiments, the device has a width within a range from about 55 mm to about 65 mm.

Figure 4:
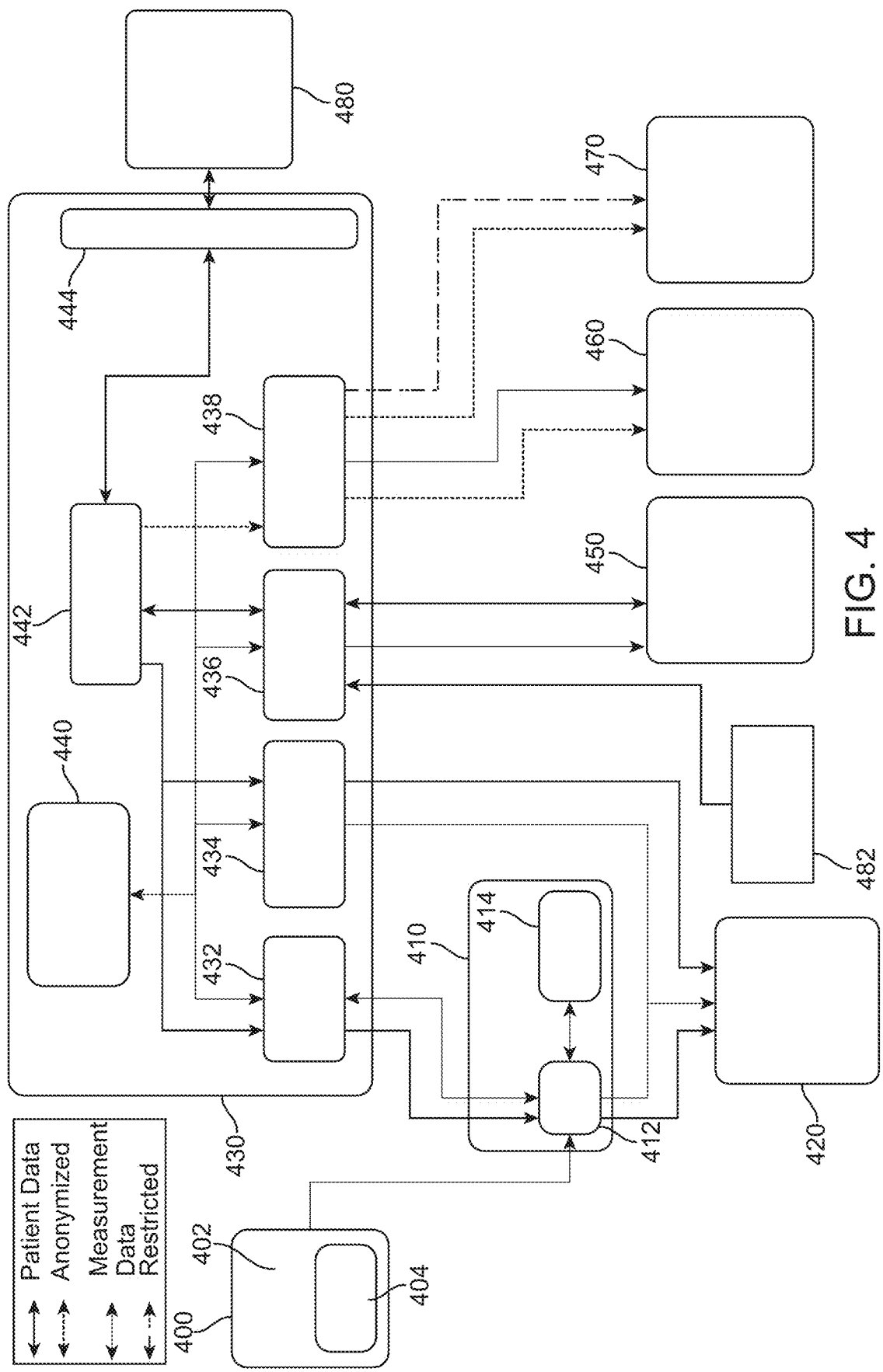
FIG. 4 shows a diagram of the flow of information in the handheld OCT system, in accordance with some embodiments.

FIG. 4 shows a diagram of the flow of information in the handheld OCT system, in accordance with some embodiments. In some cases, the handheld OCT device 400 further comprises a subsystem 402 for measuring RT or RLT and a device storage system 404. In some embodiments, the device storage system comprises any form of volatile or non-volatile memory, including but not limited to Flash memory or random access memory (RAM). In some instances, the subsystem for measuring RT or RLT is communicatively coupled to the device storage system. In some cases, the handheld OCT device transmits measurement data to a smartphone or any other computing device 410. For example, in some cases the smartphone or another handheld device further comprises a smartphone storage system 414 and run a smartphone app 412.

In some cases, the computing device sends patient data and measurement data to a patient device 420. In some embodiments, the smartphone device is communicatively coupled to a cloud-based or other network-based storage and communications system 430. In some instances, the cloud-based or other network-based storage system further comprises any of a mobile application programming interface (API) 432, a patient device 434, a physician device 436, an analytics device 438, a measurement and treatment storage system 440, a patient data storage system 442, and an API 444 interfacing with a patient administration system or a hospital administration system.

In some cases, the mobile API is communicatively couple to the smartphone app. In some embodiments, the mobile API is configured to send and receive measurement information (e.g. measurements of the RT) to and from the smartphone app. In some instances, the mobile API is configured to send patient data (e.g. identifying information or demographic information) to the smartphone device but not to receive this information from the smartphone app. In some cases, this configuration is designed to reduce the likelihood of compromising patient data. In some embodiments, the mobile API is configured to send measurement data and patient data to the patient device and to receive measurement data and patient data from the patient app. In some instances, the patient device is further configured to send measurement data and patient data to the patient and to receive measurement data and patient data from the patient.

In some cases, the mobile API is configured to send measurement data and patient data to the physician device and to receive measurement data and patient data from the physician app. In other cases, the mobile API is configured to send measurement data to the physician device and to receive measurement data and from the physician device but require patient data to first pass through a patient data storage system. In such a case, the patient data storage system is configured to send patient data to the physician device and receive patient data from the physician app. In some embodiments, the patient data storage system is configured to send patient data to the API interfacing with a patient administration system or a hospital administration system and to receive patient data from the API interfacing with a patient administration system or a hospital administration system. In some instances, the API interfacing with a patient administration system or a hospital administration system is configured to send patient data to a patient administration system or hospital administration system 480 and to receive patient data from the patient administration system or hospital administration system. In some cases, the physician device is further configured to send measurement data and patient data to a physician 450 and to receive measurement data and patient data from the physician.

In some cases, the mobile API is configured to send measurement data to the analytics apps and to receive measurement data from the analytics app. In some embodiments, the analytics device is configured to send measurement data to the manufacturer or developer of the handheld OCT system 460. In some instances, the analytics device is configured to send anonymized patient data to the manufacturer or developer of the handheld OCT system. In some cases, the analytics device is configured to send a subset of the measurement data to other parties 470. In some embodiments, the analytics device is configured to send anonymized patient data to other parties 470.

In some embodiments, the cloud-based or other network-based storage and communications system further comprise a measurement and treatment storage system. In some instances, the measurement and treatment storage system is configured to send measurement data to any of the mobile API, the patient app, the physician app, and the analytics app. In some cases, the measurement and treatment storage system is configured to receive measurement data from any of the mobile API, the patient app, the physician app, and the analytics app.

In addition to the patient administration system or hospital information system, in some cases the cloud-based or other network-based storage and communications system is communicatively coupled to a local patient administration system 482. In some embodiments, the local patient administration system is configured to send patient data to the physician app.

The handheld OCT device may utilize any method for optical coherence tomography. In some cases, the handheld OCT device utilizes time domain OCT. In some embodiments, the handheld OCT device utilizes frequency domain OCT. In some instances, the handheld OCT device utilizes spatially encoded frequency domain OCT. In some cases, the handheld OCT device utilizes time encoded frequency domain OCT, also known as swept source OCT (SS-OCT).

Figure 5:
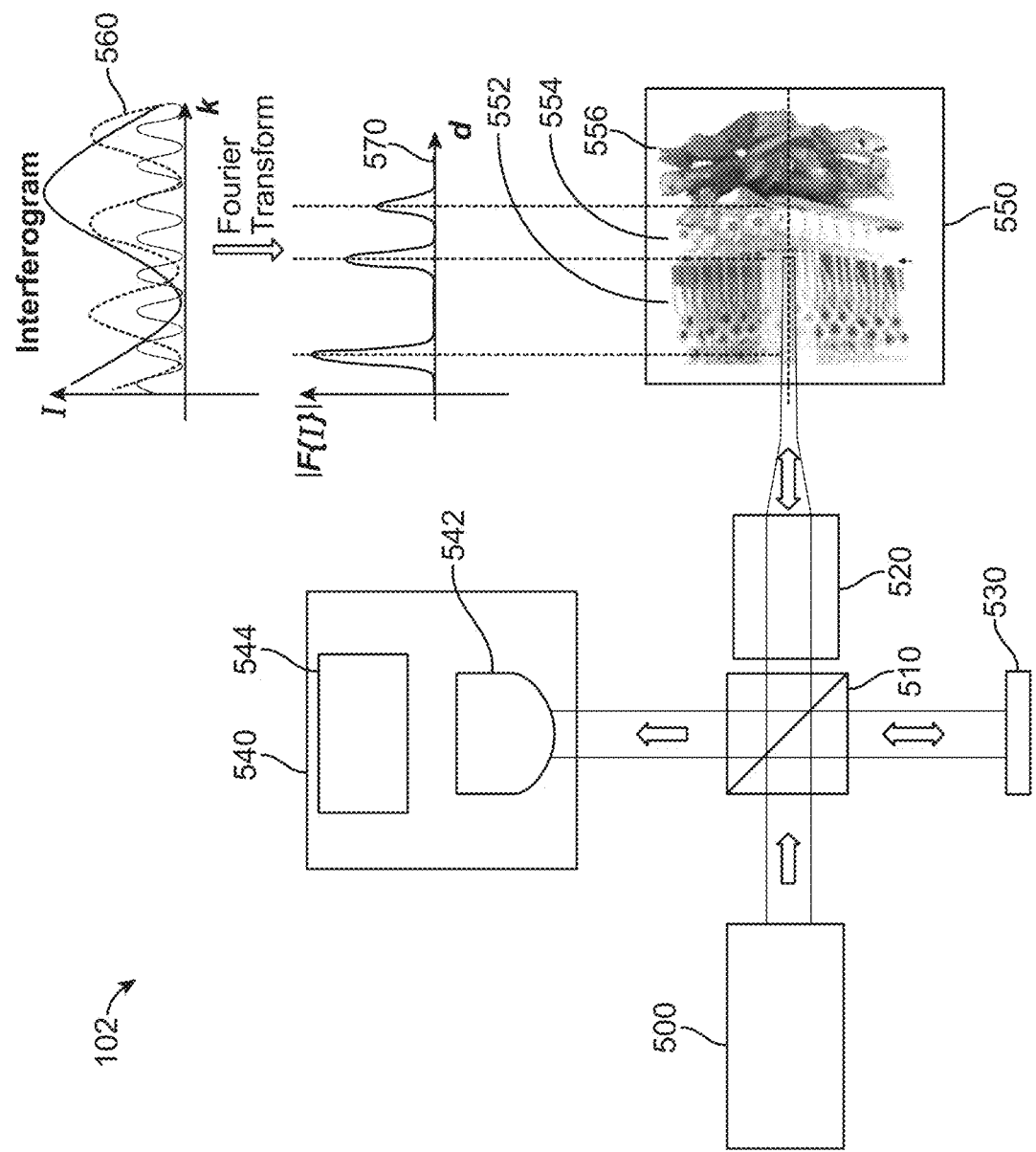
FIG. 5 shows a schematic for a swept source optical coherence tomography (SS-OCT) device, in accordance with some embodiments.

FIG. 5 shows a schematic for the optics of a swept source optical coherence tomography (SS-OCT) device, in accordance with some embodiments. In some cases, the optics 102 comprises a light source 500, a beamsplitter 510, front-end optics 520, a reference mirror 530, and a processing unit 540. In some embodiments, the processing unit further comprises a photodetector 542 and a signal processing module 544. Light from the light source impinges upon the beamsplitter. A portion of the light is directed along a reference arm to a reference mirror and a portion of the light is directed to the front-end optics and then to the sample 550. In some instances, the sample comprises an eye. In some cases, the sample comprises a retina. In some embodiments, the retina comprises a number of layers of tissue. In some instances, the layers of tissue comprise a layer of light-sensitive rod and cone cells 552, the retinal pigment epithelium (RPE) 554, and the choroid 556. In other instances, the layers of tissue comprise other layers of the retina, such as the nerve fiber layer, the ganglion cell layer, the inner plexiform layer, the inner nuclear layer, the outer plexiform layer, the outer nuclear layer, the inner limiting membrane, the external limiting membrane, and/or Bruch's membrane. Light is reflected back to the device at each boundary of each of the layers. Light reflected from each boundary interferes with light reflected from the reference mirror and with light reflected from any other boundary. The interference signal is detected at the photodetector. In some instances, light is reflected from the posterior surface of the layer of rod and cone cells, the anterior surface of the layer of rod and cone cells, the posterior surface of the inner limiting membrane, the anterior surface of the inner limiting membrane, the posterior surface of the choroid, and/or the anterior surface of the choroid. Light may be reflected from any surface of any other layer, such as the nerve fiber layer, the ganglion cell layer, the inner plexiform layer, the inner nuclear layer, the outer plexiform layer, the outer nuclear layer, the external limiting membrane, and/or the retinal pigment epithelium. In some cases, a RLT corresponds to a thickness of any of these retinal layers, or a thickness between any two such layers.

This process is repeated over the range of wavelengths emitted by the light source. The amplitude of the interference signal varies with wavelength and attains a maximum value when the light reflected from a boundary and the light reflected from the reference mirror are in phase or when the light reflected from a boundary is in phase with light reflected from another boundary. This condition is attained at one or more particular wavelengths of light for each boundary and is characterized by one or more maxima in the interference signal. At other wavelengths, the interference signal displays partial constructive interference or destructive interference. The interference signals at all wavelengths are compiled to form an interferogram 560. The interferogram is subjected to a signal analysis procedure. In some cases, the interferogram is subjected to a frequency analysis procedure, such as a fast Fourier transform (FFT), to form a spectrum 570. The spectrum comprises peaks corresponding to the interference signals associated with the thickness of various retinal layers. In some embodiments, the SS-OCT utilizes a light source with a relatively long coherence length (typically greater than a few millimeters). In some instances, the amplitude of the interference signal decreases as the distance between two retinal layers increases. In some cases, the position of a peak is indicative of the thickness of each layer of the tissue.

In some cases, the light source comprises a laser source. In some embodiments, the laser source produces laser light having a wavelength that may be tuned. In some instances, the laser source is scanned over a range of wavelengths in order to obtain an OCT signal. In some cases, the laser source is capable of being scanned rapidly to allow rapid attainment of the OCT signal. In some cases, the laser source comprises a vertical cavity surface emitting laser (VCSEL) laser. In some embodiments, the VCSEL is tuned by varying the electrical current provided to the VCSEL. In some instances, the VCSEL is scanned continuously across a range of wavelengths by continuously varying the electrical current. In some cases, the VCSEL is periodically scanned across a range of wavelengths by periodically varying the electrical current. In some embodiments, the VCSEL is provided with a sinusoidally varying electrical current to produce a sinusoidally varying wavelength.

In some embodiments, the VCSEL is a commercially available VCSEL. In some instances, the VCSEL is a VCSEL modified from a commercially available VCSEL based on the teachings described herein. In some cases, the VCSEL is a VCSEL obtained from manufacturers such as Phillips Photonics, Frankfurt Laser Company, Hamamatsu Corporation, New Focus, Power Technology, Avago Technologies, Masimo Semiconductor, Finisar, Oclaro, or any other manufacturer known to one having skill in the art.

In some instances, the VCSEL has a maximum recommended current for continuous use or for pulsed use. In some cases, the maximum continuous current rating limits the range of wavelengths over which the VCSEL may be swept. For instance, the VCSEL may be limited to a continuous operating current no more than 1 mA, 2 mA, 3 mA, 4 mA, 5 mA, 6 mA, 7 mA, 8 mA, 9 mA, or 10 mA. In some embodiments, the wavelength emitted by the VCSEL varies linearly with the operating current with a proportionality constant of 0.3 nm/mA. In some cases, this limits the range of wavelengths over which the VCSEL may be swept to 0.3 nm, 0.6 nm, 0.9 nm, 1.2 nm, 1.5 nm, 1.8 nm, 2.1 nm, 2.4 nm, 2.7 nm, or 3.0 nm. In some embodiments, this limits the attainable axial resolution of the VCSEL-based SS-OCT device. Assuming a Gaussian spectrum from the light source, the attainable axial resolution is determined according to:

$$\delta z = \frac{2\ln 2 \lambda_0^2}{\pi \Delta \lambda} \quad (1)$$

Here, $\delta z$ is the attainable axial resolution, $\lambda_0$ is the central emission wavelength of the VCSEL, and $\Delta \lambda$ is the range of wavelengths over which the VCSEL operates.

Thus, in some cases, the limited operating range of the VCSEL limits the attainable axial resolution. In some embodiments, for a VCSEL with a central operating wavelength of 850 nm, the attainable axial resolution is no better than 1062 μm, 531 μm, 354 μm, 266 μm, 213 μm, 177 μm, 152 μm, 133 μm, 118 μm, or 106 μm for operating ranges of 0.3 nm, 0.6 nm, 0.9 nm, 1.2 nm, 1.5 nm, 1.8 nm, 2.1 nm, 2.4 nm, 2.7 nm, and 3.0 nm, respectively. In some instances, the VCSEL emits no more than 0.01 mW, 0.025 mW, 0.05 mW, 0.1 mW, 0.25 mW, 0.5 mW 1 mW, 2.5 mW, 5 mW, 10 mW, 25 mW, 50 mW, 100 mW, 250 mW, 500 mW, 1 W, 2.5 W, 5 W, 10 W, 25 W, 50 W, or 100 W of optical power.

Table 1 shows axial resolution for the corresponding wavelength range of the swept source for a central operating wavelength of 850 nm.

| Wavelength Range (nm) | Axial Resolution (μm) |
|---|---|
| 0.3 | 1062.7 |
| 0.6 | 531.4 |
| 0.9 | 354.2 |
| 1.2 | 265.7 |
| 1.5 | 212.5 |
| 1.8 | 177.1 |
| 2.1 | 151.8 |
| 2.4 | 132.8 |
| 2.7 | 118.1 |
| 3.0 | 106.3 |
| 4.0 | 79.7 |
| 5.0 | 63.8 |
| 6.0 | 53.1 |
| 7.0 | 45.5 |
| 8.0 | 39.9 |
| 9.0 | 35.4 |
| 10.0 | 31.9 |

Although Table 1 makes reference to a central wavelength of 850 nm, a person of ordinary skill in the art can construct a compact OCT system operating at a different central wavelength with similar sweep ranges and similar resolutions in accordance with the disclosure provided herein. Also, a person of ordinary skill in the art can readily correct the above values in accordance with the index of refraction of the retina, which is generally between about 1.3 and 1.4.

In some cases, additional VSCELs are used to extend the swept wavelength range as described herein.

In some cases, the limited operating range of the VCSEL also limits the ability to extract information from the OCT signal due to a limited phase shift imparted by a limited optical path difference (OPD). The phase shift between light reflected from a first interface and light reflected from a second interface is given by:

$$\Delta \Phi = \frac{4\pi}{\lambda_0^2} n \Delta z \Delta \lambda \quad (2)$$

Here, $\Delta \Phi$ is the phase shift, $\lambda_0$ is the central emission wavelength of the VCSEL, n is the index of refraction of the medium between the first and second reflecting interfaces, $\Delta z$ is the distance between the first and second reflecting interfaces, $n\Delta z$ is the OPD, and $\Delta \lambda$ is the range of wavelengths over which the VCSEL operates.

In some cases, it is useful to extract frequency information from the interference signal arising from the interaction of light reflected from the first interface and light reflected from the second interface. In order to extract this information, it may be helpful to attain two signal periods of the interferogram. This corresponds to a phase shift of $4\pi$. Thus, a VCSEL should operate over a minimum range of wavelengths $\Delta \lambda_{min}$ given by:

$$\Delta \lambda_{min} = \frac{\lambda_0^2}{n \Delta z} \quad (3)$$

Thus, in some cases, the limited operating range of the VCSEL limits the ability to attain sufficient phase shifts to extract frequency information from an interference signal in some cases, for example. In some embodiments, for a VCSEL with a central operating wavelength of 850 nm, forming interference patterns between reflecting interfaces separated by 150 am in a medium with an index of refraction of 1.3, similar to a retina, a minimum range of wavelengths is 3.7 nm. In some instances, this range of wavelengths is greater than the range of wavelengths that is typically emitted by a VCSEL operated within its maximum recommended current for continuous use. Thus, in some cases, it is be helpful to extend the range of wavelengths emitted by the VCSEL in order to produce a sufficient phase shift.

The light source need not be a VCSEL. In some cases, the light source is doped fiber amplifier utilizing amplified spontaneous emission (ASE). In some cases, the light source is a superluminescent diode (SLD). Additionally, in some embodiments, the light source comprises multiple light sources.

In some cases, the front-end optics comprise optical elements such as lenses. In some embodiments, the front-end optics comprise any reflective, refractive, or diffractive elements. In some instances, the front-end optics comprise more than one reflective, refractive, or diffractive elements. In some cases, the front-end optics comprise electro-optic, magneto-optic, acousto-optic, or mechano-optic devices. In some embodiments, the front-end optics comprise any optical elements known to one having skill in the art.

In some embodiments, the front end optics comprise a scanning optical element to allow the light source to be moved to different locations on the retina. In some instances, this allows multiple measurements to be conducted to determine a RT or RLT at different locations on the retina. In some cases, determining a RT or RLT at different locations on the retina further allows the location of the fovea to be ascertained. In some embodiments, the scanning optical element is selected from the group consisting of a mirror, a plurality of mirrors, a gimbal, a lens, a galvanometer, an acousto-optic modulator, an electro-optic modulator, a translating optical element, an optical element translating transverse to the light beam, a deformable mirror and an xy translation stage. In some instances, the scanning optical element comprises any scanning optical element as is known to one having skill in the art.

In some instances, the device further comprises a scanning optical element as described herein.

Figure 6A:
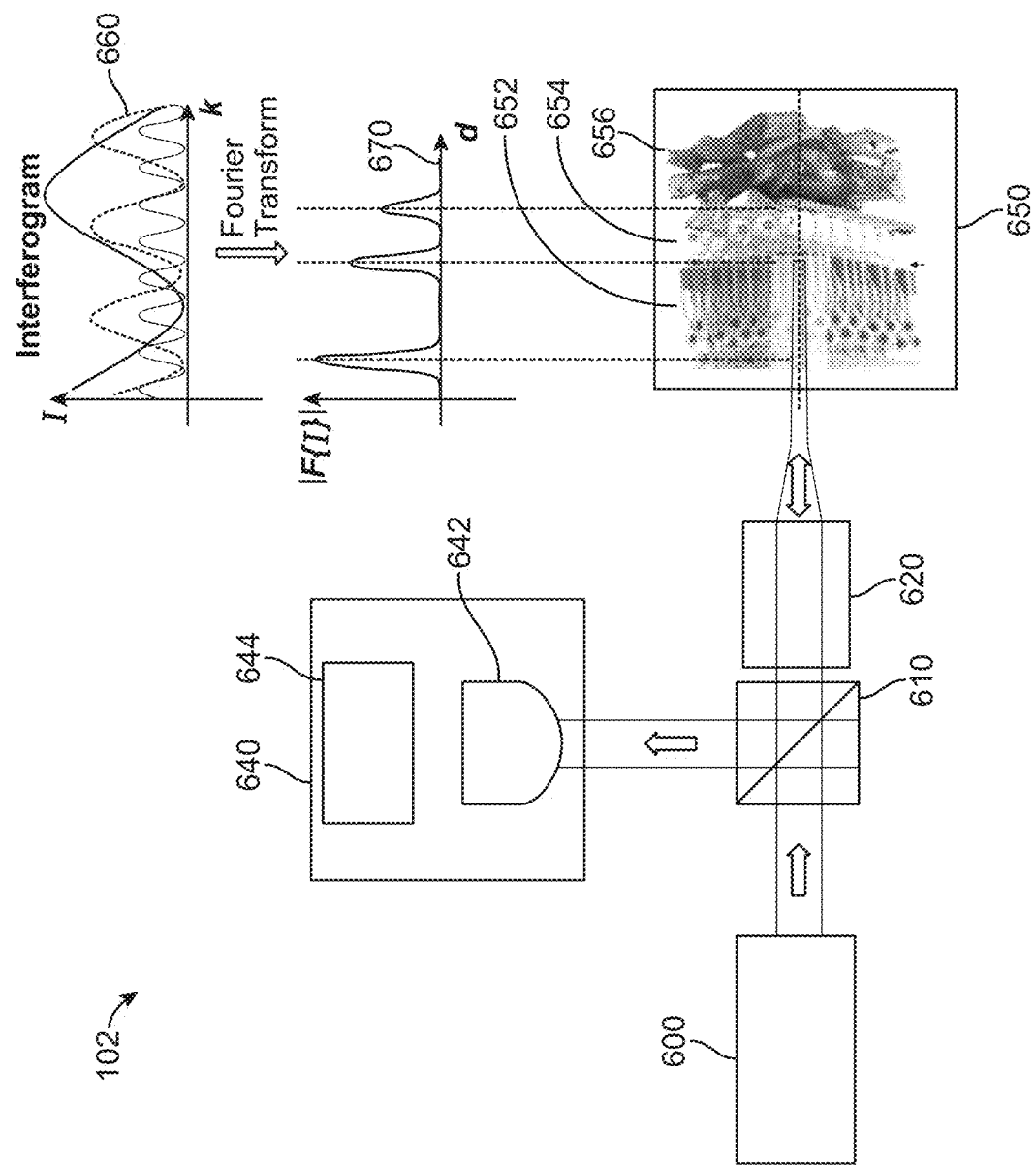
FIG. 6A shows a schematic for a SS-OCT device lacking a reference mirror, in accordance with some embodiments.

FIG. 6A shows a schematic for the optics of a swept source optical coherence tomography (SS-OCT) device lacking a reference mirror, in accordance with some embodiments. In some cases, the optics 102 comprise a VCSEL or other light source 600, a beamsplitter 610, front-end optics 620, and a processing unit 640. In some embodiments, the processing unit further comprises a photodetector 642 and a signal processing module 644. Light from the broadband source impinges upon the beamsplitter. Light is directed to the front-end optics and then to the sample 650. Light is reflected back to the device at each boundary of each layer. Light reflected from a boundary of one layer interferes with light reflected from a boundary of another layer. The interference signal is detected at the photodetector.

This process is repeated over the range of wavelengths emitted by the light source. The amplitude of the interference signal varies with wavelength and attains a maximum value when the light reflected from a boundary is in phase with light reflected from another boundary. This condition is attained at one or more particular wavelengths of light for each boundary and is characterized by one or more maxima in the interference signal. At other wavelengths, the interference signal displays partial constructive interference or destructive interference. The interference signals at all wavelengths are compiled to form an interferogram. The interferogram is subjected to a signal analysis procedure. In some cases, the interferogram is subjected to a frequency analysis procedure, such as a fast Fourier transform (FFT), to form a spectrum. The spectrum comprises peaks corresponding to the wavelengths associated with an interference maximum for each boundary. In some embodiments, the SS-OCT utilizes a light source with a relatively long coherence length (typically greater than a few millimeters). In some instances, the amplitude of the interference signal decreases as the distance between two retinal layers increases. In some cases, the position of a peak is indicative of the thickness of each layer of the tissue.

In some cases, the light source comprises a laser source. In some embodiments, the laser source produces laser light having a wavelength that may be tuned. In some instances, the laser source is scanned over a range of wavelengths in order to obtain an OCT signal. In some cases, the laser source is capable of being scanned rapidly to allow rapid attainment of the OCT signal. In some embodiments, the laser source comprises a vertical cavity surface emitting laser (VCSEL) laser. In some instances, the VCSEL is tuned by varying the electrical current provided to the VCSEL. In some cases, the VCSEL is scanned continuously across a range of wavelengths by continuously varying the electrical current. In some embodiments, the VCSEL is periodically scanned across a range of wavelengths by periodically varying the electrical current. For instance, the VCSEL may be provided with a sinusoidally varying electrical current to produce a sinusoidally varying wavelength.

In some embodiments, the front-end optics comprise optical elements such as lenses. In some instances, the front-end optics comprise any reflective, refractive, or diffractive elements. In some cases, the front-end optics comprise more than one reflective, refractive, or diffractive elements. In some embodiments, the front-end optics comprise electro-optic, magneto-optic, acousto-optic, or mechano-optic devices. The front-end optics may comprise any optical elements known to one having skill in the art.

Figure 6B:
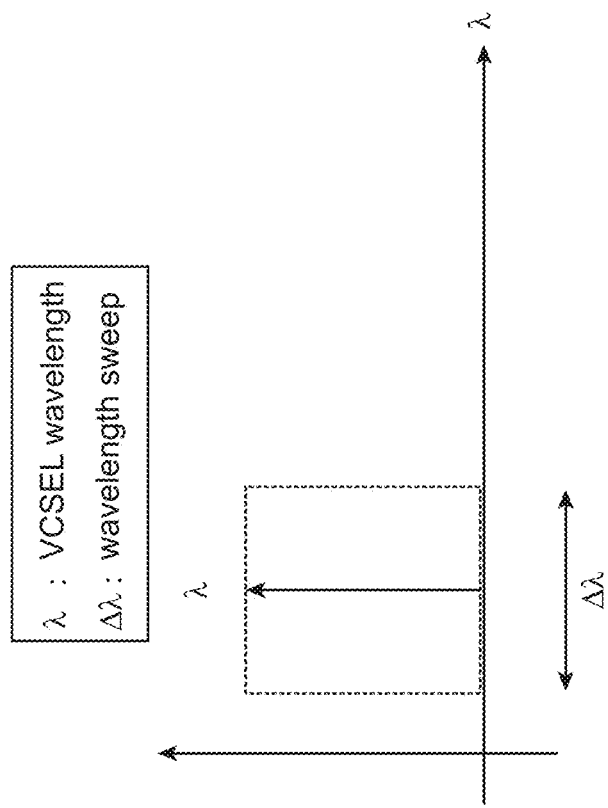
FIG. 6B shows the wavelength range over which the vertical cavity surface emitting laser (VCSEL) operates in the SS-OCT device lacking a reference mirror, in accordance with some embodiments.

FIG. 6B shows the wavelength range over which the VCSEL operates in the swept source optical coherence tomography (SS-OCT) device lacking a reference mirror, in accordance with some embodiments. In some cases, the VCSEL has a maximum recommended current for continuous use. In some embodiments, the maximum continuous current rating limits the range of wavelengths over which the VCSEL may be swept. In some instances, the VCSEL is limited to a continuous operating current no more than 1 mA, 2 mA, 3 mA, 4 mA, 5 mA, 6 mA, 7 mA, 8 mA, 9 mA, or 10 mA. In some cases, the wavelength emitted by the VCSEL varies linearly with the operating current with a proportionality constant of 0.3 nm/mA. In some embodiments, this limits the range of wavelengths over which the VCSEL may be swept to 0.3 nm, 0.6 nm, 0.9 nm, 1.2 nm, 1.5 nm, 1.8 nm, 2.1 nm, 2.4 nm, 2.7 nm, or 3.0 nm. In some instances, this limits the attainable axial resolution of the VCSEL-based SS-OCT device.

Thus, in some cases, the limited operating range of the VCSEL limits the attainable axial resolution. For instance, for a VCSEL with a central operating wavelength of 850 nm, the attainable axial resolution is no better than 1062 µm, 531 µm, 354 µm, 266 µm, 213 µm, 177 µm, 152 µm, 133 µm, 118 µm, or 106 µm for operating ranges of 0.3 nm, 0.6 nm, 0.9 nm, 1.2 nm, 1.5 nm, 1.8 nm, 2.1 nm, 2.4 nm, 2.7 nm, and 3.0 nm, respectively. In some embodiments, the VCSEL emits no more than 0.01 mW, 0.025 mW, 0.05 mW, 0.1 mW, 0.25 mW, 0.5 mW 1 mW, 2.5 mW, 5 mW, 10 mW, 25 mW, 50 mW, 100 mW, 250 mW, 500 mW, 1 W, 2.5 W, 5 W, 10 W, 25 W, 50 W, or 100 W of optical power.

The light source need not be a VCSEL. In some cases, the light source is a doped fiber amplifier utilizing amplified spontaneous emission (ASE). In some cases, the light source is a superluminescent diode (SLD). Additionally, in some embodiments, the light source comprises multiple light sources.

Regardless of whether the SS-OCT device utilizes a reference mirror or not, the limited frequency range of the VCSEL causes the SS-OCT device to have an attainable axial resolution value less than about 100 μm.

Figure 7A:
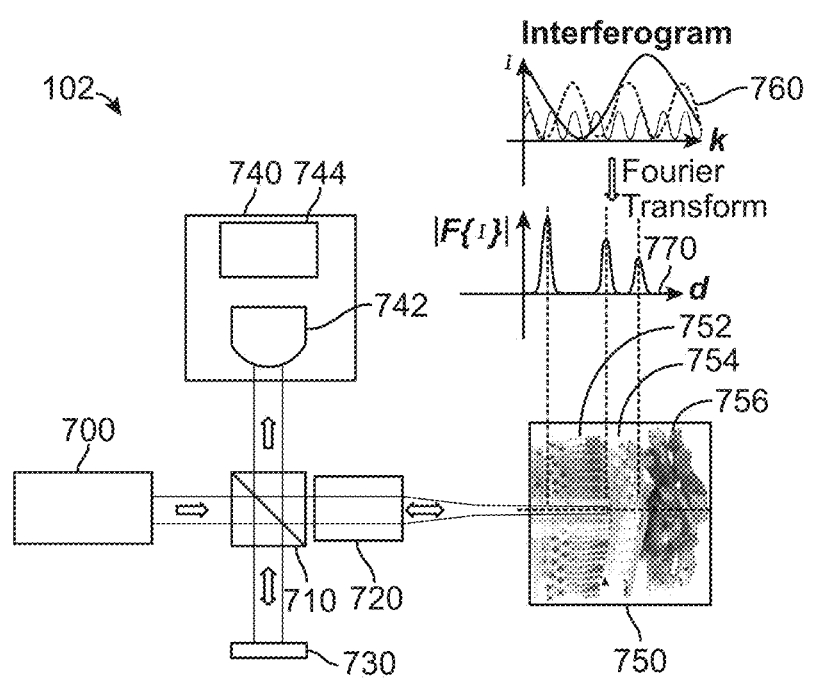
FIG. 7A shows a schematic for a SS-OCT device utilizing an external cavity, in accordance with some embodiments.

FIG. 7A shows a schematic for the optics of a swept source optical coherence tomography (SS-OCT) device utilizing a reference mirror, in accordance with some embodiments. In some cases, the optics 102 comprise a VCSEL or other light source 700, a beamsplitter 710, front-end optics 720, a reference mirror 730, and a processing unit 740. In some embodiments, the processing unit further comprises a photodetector 742 and a signal processing module 744. Light from the light source impinges upon the beamsplitter. A portion of the light is directed along a reference arm to a reference mirror and a portion of the light is directed to the front-end optics and then to the sample 750. Light is reflected back to the device at each boundary of each layer. Light reflected from each boundary interferes with light reflected from the reference mirror and with light reflected from any other boundary. The interference signal is detected at the photodetector.

This process is repeated over the range of wavelengths emitted by the light source. The amplitude of the interference signal varies with wavelength and attains a maximum value when the light reflected from a boundary and the light reflected from the reference mirror are in phase or when the light reflected from a boundary is in phase with light reflected from another boundary. This condition is attained at one or more particular wavelengths of light for each boundary and is characterized by one or more maxima in the interference signal. At other wavelengths, the interference signal displays partial constructive interference or destructive interference. The interference signals at all wavelengths are compiled to form an interferogram. The interferogram is subjected to a signal analysis procedure. In some cases, the interferogram is subjected to a frequency analysis procedure, such as a fast Fourier transform (FFT), to form a spectrum. The spectrum comprises peaks corresponding to the wavelengths associated with an interference maximum for each boundary. In some cases, the SS-OCT utilizes a light source with a relatively long coherence length (typically greater than a few millimeters). In some embodiments, the amplitude of the interference signal decreases as the distance between two retinal layers increases. In some instances, the position of a peak is indicative of the thickness of each layer of the tissue. The reference mirror allows longer optical path lengths for the light traveling to the sample. In some cases, this has the effect of shifting the frequency at which the maximum interference signal is attained to a higher frequency. In some embodiments, this shift to higher frequency allows for detection of the OCT signal in a manner that is more robust to noise.

In some cases, the light source comprises a laser source. In some embodiments, the laser source produces laser light having a wavelength that may be tuned. In some instances, the laser source is scanned over a range of wavelengths in order to obtain an OCT signal. In some cases, the laser source is capable of being scanned rapidly to allow rapid attainment of the OCT signal. In some embodiments, the laser source comprises a vertical cavity surface emitting laser (VCSEL) laser. In some instances, the VCSEL is tuned by varying the electrical current provided to the VCSEL. In some cases, the VCSEL is scanned continuously across a range of wavelengths by continuously varying the electrical current. In some embodiments, the VCSEL is periodically scanned across a range of wavelengths by periodically varying the electrical current. For instance, the VCSEL may be provided with a sinusoidally varying electrical current to produce a sinusoidally varying wavelength.

In some embodiments, the front-end optics comprise optical elements such as lenses. In some instances, the front-end optics comprise any reflective, refractive, or diffractive elements. In some cases, the front-end optics comprise more than one reflective, refractive, or diffractive elements. In some embodiments, the front-end optics comprise electro-optic, magneto-optic, acousto-optic, or mechano-optic devices. The front-end optics may comprise any optical elements known to one having skill in the art.

In some cases, the front end optics comprise a scanning optical element as described herein.

Figure 7B:
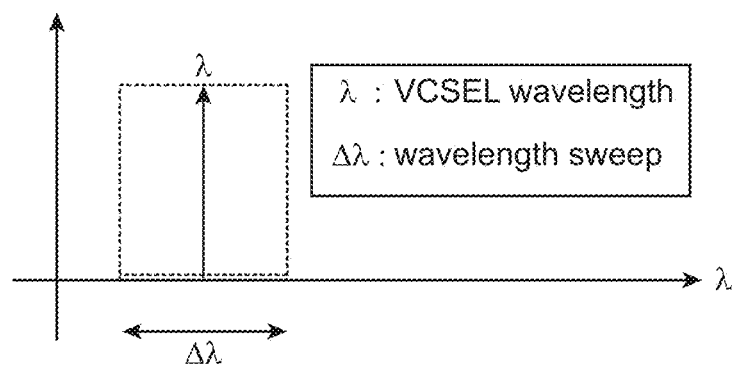
FIG. 7B shows the wavelength range over which the VCSEL operates in the SS-OCT device lacking a reference mirror, in accordance with some embodiments.

FIG. 7B shows the wavelength range over which the VCSEL operates in the swept source optical coherence tomography (SS-OCT) device lacking a reference mirror, in accordance with some embodiments. The light source emits light with a central wavelength λ. The central wavelength is varied over a range of wavelengths Δλ.

Figure 7C:
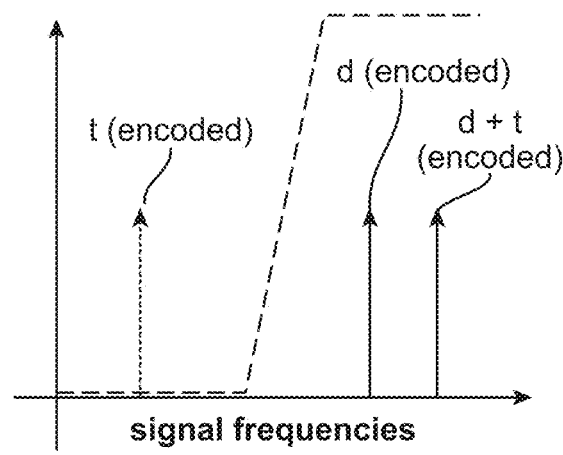
FIG. 7C shows how the use of an external cavity mirror may shift the OCT peaks to a higher optical frequency compared to the frequency of the OCT peak in the absence of the external cavity mirror.

FIG. 7C shows how a reference mirror may shift the OCT peaks to a higher optical frequency compared to the frequency of the OCT peak in the absence of the reference mirror. In the absence of the reference mirror, the OCT peak of a given sample is obtained at a relatively low frequency, indicated by t(encoded). This frequency correspond to the optical path difference in the sample. The present of the reference mirror has the effect that each boundary of a sample interferes with the reference mirror. For a sample with two boundaries, this effect gives rise to two relatively high frequency components in the OCT signal, denoted as d(encoded) and d+t(encoded) in FIG. 7C. The difference between these two frequencies corresponds to the distance between the boundaries of the sample. For a retina or retinal layer, the different thus corresponds to a RT or RLT, respectively.

In some cases, the VCSEL has a maximum recommended current for continuous use. In some embodiments, the maximum continuous current rating limits the range of wavelengths over which the VCSEL may be swept. In some instances, the VCSEL is limited to a continuous operating current no more than 1 mA, 2 mA, 3 mA, 4 mA, 5 mA, 6 mA, 7 mA, 8 mA, 9 mA, or 10 mA. In some cases, the wavelength emitted by the VCSEL varies linearly with the operating current with a proportionality constant of 0.3 nm/mA. In some embodiments, this current limit limits the range of wavelengths over which the VCSEL may be swept. In some instances, the VCSEL is swept over a range defined by any two of the following numbers: 0.3 nm, 0.6 nm, 0.9 nm, 1.2 nm, 1.5 nm, 1.8 nm, 2.1 nm, 2.4 nm, 2.7 nm, or 3.0 nm. In some cases, this sweeping range limit limits the attainable axial resolution of the VCSEL-based SS-OCT device. In some embodiments, the sweep range is increased by driving the current beyond the maximum current rating, as described herein.

Thus, in some cases, the limited operating range of the VCSEL limits the attainable axial resolution. In some embodiments, for a VCSEL with a central operating wavelength of 850 nm, the attainable axial resolution is no better than 1062 μm, 531 μm, 354 μm, 266 μm, 213 μm, 177 m, 152 μm, 133 μm, 118 μm, or 106 μm for operating ranges of 0.3 nm, 0.6 nm, 0.9 nm, 1.2 nm, 1.5 nm, 1.8 nm, 2.1 nm, 2.4 nm, 2.7 nm, and 3.0 nm, respectively. In some instances, the VCSEL emits no more than 0.01 mW, 0.025 mW, 0.05 mW, 0.1 mW, 0.25 mW, 0.5 mW 1 mW, 2.5 mW, 5 mW, 10 mW, 25 mW, 50 mW, 100 mW, 250 mW, 500 mW, 1 W, 2.5 W, 5 W, 10 W, 25 W, 50 W, or 100 W of optical power.

The light source need not be a VCSEL. In some cases, the light source is a doped fiber amplifier utilizing amplified spontaneous emission (ASE). In some cases, the light source is a superluminescent diode (SLD). Additionally, in some embodiments, the light source comprises multiple light sources.

In some cases, the limited attainable axial resolution is improved by utilizing two or more VCSELs or other light sources in the SS-OCT system. In some embodiments, each of the two or more VCSELs or other light sources has an emission spectrum which is distinct from the emission spectra of each of the other VCSELs or other light sources. In some cases, the emission spectra of the two or more VCSELs partially overlap. In some cases, the emission spectra of the two or more VCSELs do not overlap. In this manner, in some embodiments, the two or more VCSELs or other light sources combine to produce a wider range of emission wavelengths for the SS-OCT measurement. In some instances, this enhances the attainable axial resolution of the SS-OCT measurement.

Figure 8A:
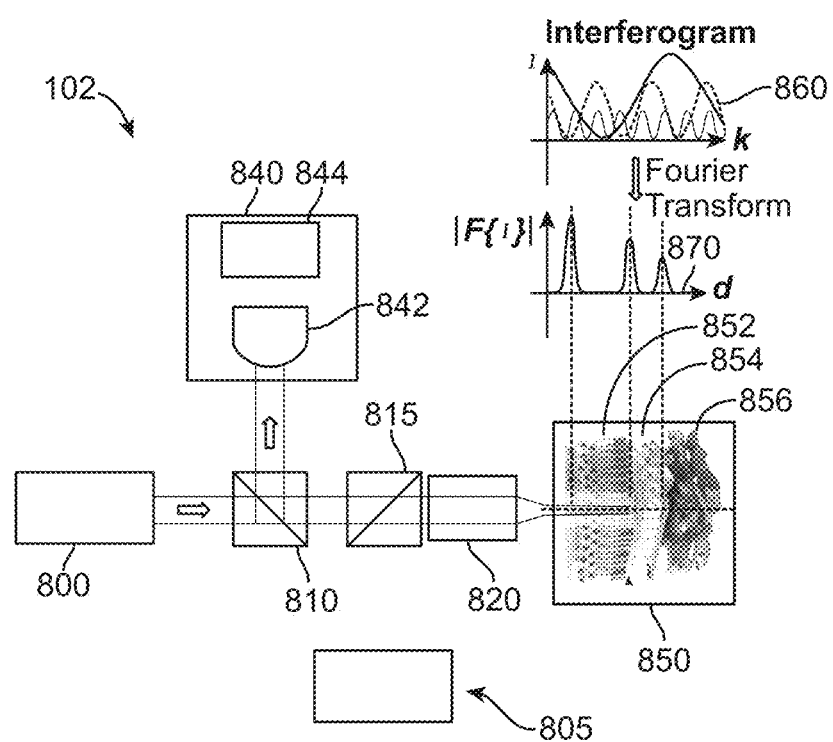
FIG. 8A shows a schematic for a SS-OCT device utilizing two VCSELs and lacking a reference mirror at a first particular point in time, in accordance with some embodiments.

FIG. 8A shows the optics of a swept source optical coherence tomography (SS-OCT) device utilizing two VCSELs and lacking a reference mirror at a first particular point in time, in accordance with some embodiments. In some cases, the optics 102 comprise a first VCSEL or other light source 800, a second VCSEL or other light source 805, a first beamsplitter 810, a second beamsplitter 815, front-end optics 820 as described herein, and a processing unit 840. In some embodiments, the processing unit further comprises a photodetector 842 and a signal processing module 844. Light from the first source impinges upon the beamsplitter. The light is then directed to the front-end optics and then to the sample 850. In some instances, at a first particular point in time, the first VCSEL or other light source is on (sending laser light to the sample) while the second VCSEL or other light source is off (not sending laser light to the sample). Light is reflected back to the device at each boundary of each layer. Light reflected from a boundary of a first layer interferes with light reflected from a back boundary of a second layer. The interference signal is detected at the photodetector.

Figure 8B:
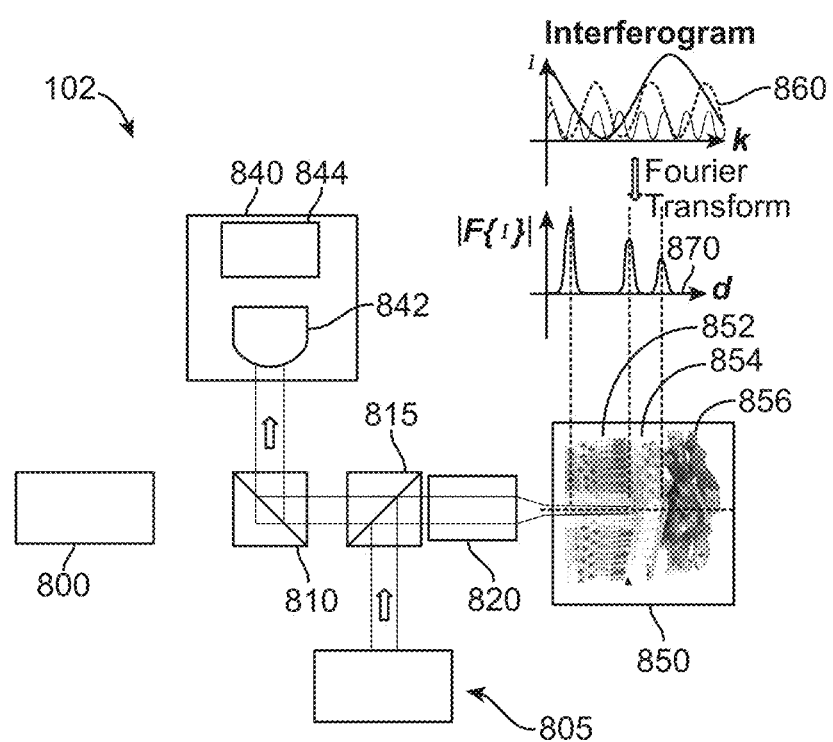
FIG. 8B shows a schematic for a SS-OCT device utilizing two VCSELs and lacking a reference mirror at second particular point in time, in accordance with some embodiments.

FIG. 8B shows a schematic for a swept source optical coherence tomography (SS-OCT) device utilizing two VCSELs and lacking a reference mirror at second particular point in time, in accordance with some embodiments. In some instances, at a second particular point in time, the first VCSEL or other light source is off (not sending laser light to the sample) while the second VCSEL or other light source is on (sending laser light to the sample). Light is reflected back to the device at each boundary of each layer. Light reflected from a boundary of a first layer interferes with light reflected from a boundary of a second layer. The interference signal is detected at the photodetector.

This process is repeated over the entire range of wavelengths emitted by the first and second light sources. The amplitude of the interference signal varies with wavelength and attains a maximum value when the light reflected from a boundary and the light reflected from the reference mirror are in phase or when the light reflected from a boundary is in phase with light reflected from another boundary. This condition is attained at one or more particular wavelengths of light for each boundary and is characterized by one or more maxima in the interference signal. At other wavelengths, the interference signal displays partial constructive interference or destructive interference. The interference signals at all wavelengths are compiled to form an interferogram. The interferogram is subjected to a signal analysis procedure. In some cases, the interferogram is subjected to a frequency analysis procedure, such as a fast Fourier transform (FFT), to form a spectrum. The spectrum comprises peaks corresponding to the wavelengths associated with an interference maximum for each boundary. In some cases, the SS-OCT utilizes light sources with a short coherence length (typically less than a few millimeters). In such a case, the amplitude of the interference signal decreases rapidly as the wavelength is moved away from the wavelength associated with the interference maximum. In some embodiments, this yields narrow peaks in the frequency spectrum. In some instances, the distances between peaks are indicative of the thickness of each layer of the tissue.

In some cases, the light sources comprise laser sources. In some embodiments, the laser sources produce laser light having a wavelength that may be tuned. In some instances, the laser sources are scanned over a range of wavelengths in order to obtain an OCT signal. In some cases, the laser sources are capable of being scanned rapidly to allow rapid attainment of the OCT signal. In some embodiments, the laser sources comprise vertical cavity surface emitting laser (VCSEL) lasers. In some instances, the VCSELs are tuned by varying the electrical current provided to the VCSELs. In some cases, the VCSELs are scanned continuously across a range of wavelengths by continuously varying the electrical current. In some embodiments, the VCSELs are periodically scanned across a range of wavelengths by periodically varying the electrical current. For instance, the VCSELs may be provided with a sinusoidally varying electrical current to produce a sinusoidally varying wavelength.

In some embodiments, the front-end optics comprise optical elements such as lenses. In some instances, the front-end optics comprise any reflective, refractive, or diffractive elements. In some cases, the front-end optics comprise more than one reflective, refractive, or diffractive elements. In some embodiments, the front-end optics comprise electro-optic, magneto-optic, acousto-optic, or mechano-optic devices. In some instances, the front-end optics comprise any optical elements known to one having skill in the art.

In some instances, the front end optics comprise a scanning optical element to allow the light source to be moved to different locations on the retina. In some cases, this allows multiple measurements to be conducted to determine a RT or RLT at different locations on the retina. In some embodiments, the scanning optical element comprises a galvanometer. In some instances, the scanning optical element comprises an acousto-optic modulator. In some cases, the scanning optical element comprises an electro-optic modulator. In some embodiments, the scanning optical element comprises an xy stage. The scanning optical element may comprise any scanning optical element as is known to one having skill in the art.

Figure 8C:
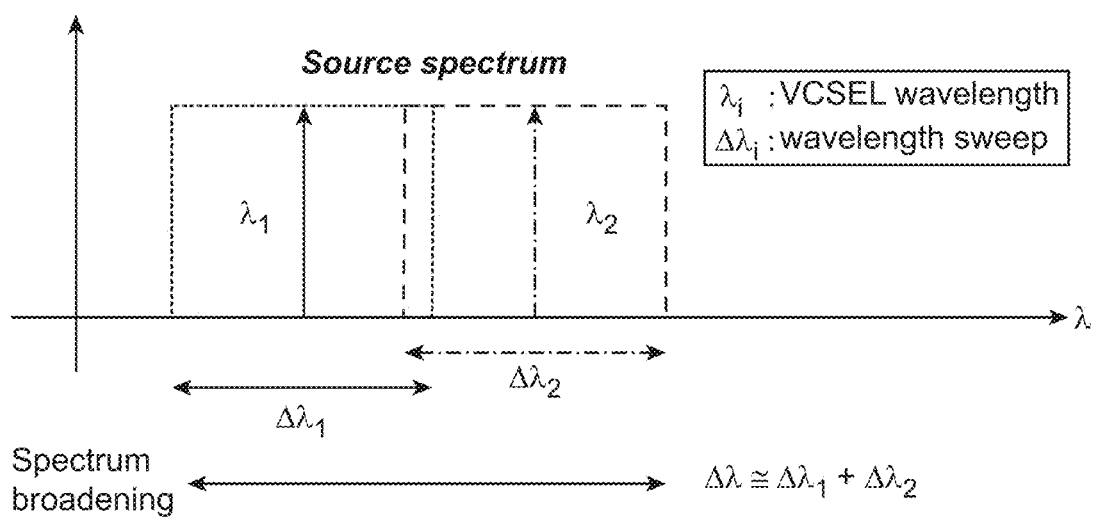
FIG. 8C shows the wavelength range over which the VCSELs operate in the SS-OCT device utilizing two VCSELs and lacking a reference mirror, in accordance with some embodiments.

FIG. 8C shows the wavelength range over which the VCSELs operate in the swept source optical coherence tomography (SS-OCT) device utilizing two VCSELs and lacking a reference mirror, in accordance with some embodiments.

The wavelength sweep may be coordinated between the two or more VCSELs or other light sources in a variety of manners. In one embodiment, the first VCSEL or other light source is swept over its entire wavelength range while the second VCSEL or other light source is off. The second VCSEL or other light source is then swept over its entire wavelength range while the first VCSEL or other light source is off. The wavelength sweep alternates between the two VCSELs or other light sources until the entire SS-OCT signal has been acquired. In some cases, the second VCSEL is configured to emit light having a wavelength within about 0.1 nm of the first VCSEL when the first VCSEL is turned off. In some embodiments, the VCSELs are swept at a rate between about 50 Hz and about 10 kHz. In some instances, the VCSELs are swept at a rate between about 1 kHz and about 5 kHz.

In another embodiment, the two or more VCSELs undergo their wavelength sweeps simultaneously and at the same rate. In such a setup it may be helpful to remove the temporal correlation between the OCT signals arising from the first VCSEL or other light source and the OCT signals arising from the second VCSEL or other light source. This may be accomplished, for instance, by modifying the optical setup of FIG. 8A to include a spectrometer in place of the photodetector, as will be readily understood be a person having skill in the art. In some cases, the sweep frequencies of the two VCSELs are substantially the same. In some embodiments, the sweep rates of the two VCSELs are within 5% of each other. In some instances, the sweep rates of the two VCSELs are within 1% of each other. In some cases, the VCSELs are swept at a rate between about 50 Hz and about 10 kHz. In some embodiments, the VCSELs are swept at a rate between about 1 kHz and about 5 kHz.

In another embodiment, the two or more VCSELs undergo their wavelength sweeps simultaneously but at different rates. For instance, the first VCSEL or other light source may be swept over its range of emission wavelengths at a first rate, so that it completes its wavelength sweep in a first amount of time. The second VCSEL or other light source is swept over its range of emission wavelengths at a second rate that is different from the first rate, so that it completes its wavelength sweep in a second amount of time that is different from the first amount of time. In this manner, the SS-OCT signals arising from the first VCSEL or other light source are encoded in time in a manner that is different from the temporal encoding of the SS-OCT signals arising from the second VCSEL or other light source. The SS-OCT signals arising from the first VCSEL or other light source are then distinguished from the SS-OCT signals arising from the second VCSEL or other light source through signal processing means. In some cases, the VCSELs are swept at a rate between about 50 Hz and about 10 kHz. In some embodiments, the VCSELs are swept at a rate between about 1 kHz and about 5 kHz.

In some embodiments, the system comprises 2, 3, 4, 5, 6, 7, 8, 9, 10, or more VCSELs or other light sources. In some instances, each VCSEL has a maximum recommended current for continuous use. In some cases, the maximum continuous operating current rating limits the range of wavelengths over which each VCSEL may be swept. For instance, each VCSEL may be limited to a continuous operating current no more than 1 mA, 2 mA, 3 mA, 4 mA, 5 mA, 6 mA, 7 mA, 8 mA, 9 mA, or 10 mA. In some cases, the wavelength emitted by each VCSEL varies linearly with the operating current with a proportionality constant of 0.3 nm/mA. In some embodiments, this limits the range of wavelengths over which each VCSEL may be swept to 0.3 nm, 0.6 nm, 0.9 nm, 1.2 nm, 1.5 nm, 1.8 nm, 2.1 nm, 2.4 nm, 2.7 nm, or 3.0 nm. In some instances, the combination of 2, 3, 4, 5, 6, 7, 8, 9, 10, or VCSELs or other light sources produces a total range of wavelengths of up to 30 nm or more. In some cases, the use of multiple VCSELs allows a swept wavelength range within the range of 5 nm to 10 nm, for example.

Thus, in some cases, the larger total operating range of the 2, 3, 4, 5, 6, 7, 8, 9, 10, or more VCSELs enhances the attainable axial resolution. In some embodiments, for a set of 2 VCSELs, each with a central operating wavelength of approximately 850 nm, the attainable axial resolution is 53 µm if each VCSEL has an operating range of 3.0 nm. With 3 VCSELs, the attainable axial resolution is 35 µm if each VCSEL has an operating range of 3.0 nm. With 4 VCSELs, the attainable axial resolution is 27 µm if each VCSEL has an operating range of 3.0 nm. In some cases, with greater and greater numbers of VCSELs, the attainable axial resolution is further enhanced. In some embodiments, each VCSEL emits no more than 0.01 mW, 0.025 mW, 0.05 mW, 0.1 mW, 0.25 mW, 0.5 mW 1 mW, 2.5 mW, 5 mW, 10 mW, 25 mW, 50 mW, 100 mW, 250 mW, 500 mW, 1 W, 2.5 W, 5 W, 10 W, 25 W, 50 W, or 100 W of optical power.

In some cases, the limited attainable axial resolution is also improved by providing the VCSEL or other light sources with a maximum electric current greater than that for which it is rated. A VCSEL is typically rated for a maximum electric current on the assumption that it will experience a high duty cycle. However, a VCSEL may be able to tolerate an electric current greater than the rated current for short periods of time. In a handheld SS-OCT device, a VCSEL may only be driven at an operating current outside of its rated range for a period required to obtain an OCT measurement. In some cases, the VCSEL is driven at an operating current outside of its rated range for less than one minute at a time. In some instances, the VCSEL is driven at an operating current outside of its rated range infrequently. For instance, in some cases, the VCSEL is driven at an operating current outside of its rated range once ever few hours. In some cases, the VCSEL is driven at an operating current outside of its rated range once every few days. In some embodiments, the VCSEL is turned off for periods in which it is not driven at an operating current outside of its rated range. In other embodiments, the VCSEL is driven at a lower operating current that is within its rated range for such periods. Thus, in some instances, a VCSEL is able to withstand being driven at a higher electric current than it is rated for under the operating conditions expected for a handheld SS-OCT device.

Figure 9:
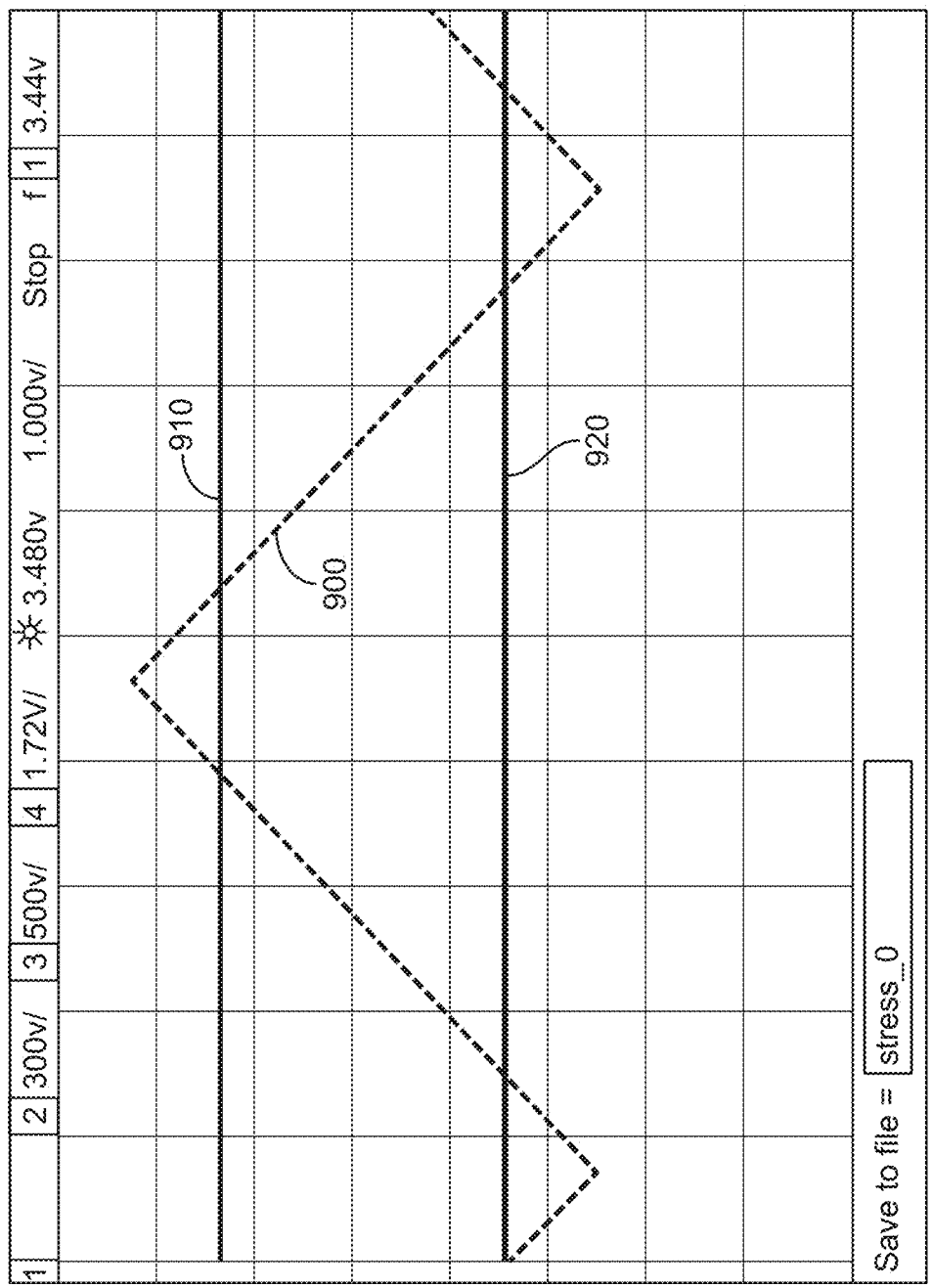
FIG. 9 shows the operation of a VCSEL beyond its maximum current rating, in accordance with some embodiments.

FIG. 9 shows the operation of a VCSEL beyond its maximum current rating. In some cases, the electric current supplied to the VCSEL is varied over time according to some waveform 900. The waveform may be triangular, sinusoidal, or any other waveform known to one having skill in the art. In some embodiments, the VCSEL has a recommended continuous electric current range specified by an upper current threshold 910 and/or a lower current threshold 920. At different time points in the waveform, the VCSEL is supplied with an electric current exceeding the upper current threshold or falling below the lower current threshold. In some cases, the maximum current exceeds the upper current threshold by more than 10%, more than 20%, more than 50%, more than 100%, more than 200%, more than 300%, more than 400%, or more than 500%. In some embodiments, the VCSEL is swept at a rate between about 50 Hz and about 10 kHz. In some instances, the VCSEL is swept at a rate between about 1 kHz and about 5 kHz.

In some cases, exceeding the maximum current allows the VCSEL to be driven beyond a specified maximum wavelength range directly related to its maximum recommend current for continuous use. In some cases, the VCSEL is driven beyond its specified wavelength range by at least about 1 nm. In some cases, the VCSEL is driven beyond its specified wavelength range by an amount within a range of 1 nm to 5 nm. In some embodiments, driving the VCSEL beyond its specified wavelength range allows a wavelength range within the range of 5 nm to 10 nm. In some instances, the VCSEL is driven beyond its maximum wavelength range for each of a plurality of measurements. To avoid overheating of the VCSEL, there may be a delay implemented between successive measurements. In some cases, the delay ranges from about 1 ms to about 100 ms. In some cases, the delay ranges from about 5 ms to about 20 ms.

In some cases, the limited attainable axial resolution afforded by a single VCSEL with a limited operating range does not present a problem for a technique that comprises measuring the thickness of a specific structure but not attempting to measure substructures within the structure. For instance, it may be of interest to attain a measurement of the RT or RLT without concern about imaging substructures within the retina. It may be of further interest to be concerned primarily with measured changes in the RT or RLT. In some cases, it is possible to obtain measurements of the RT or RLT with greater precision than may be expected from the attainable axial resolution.

Figure 10A:
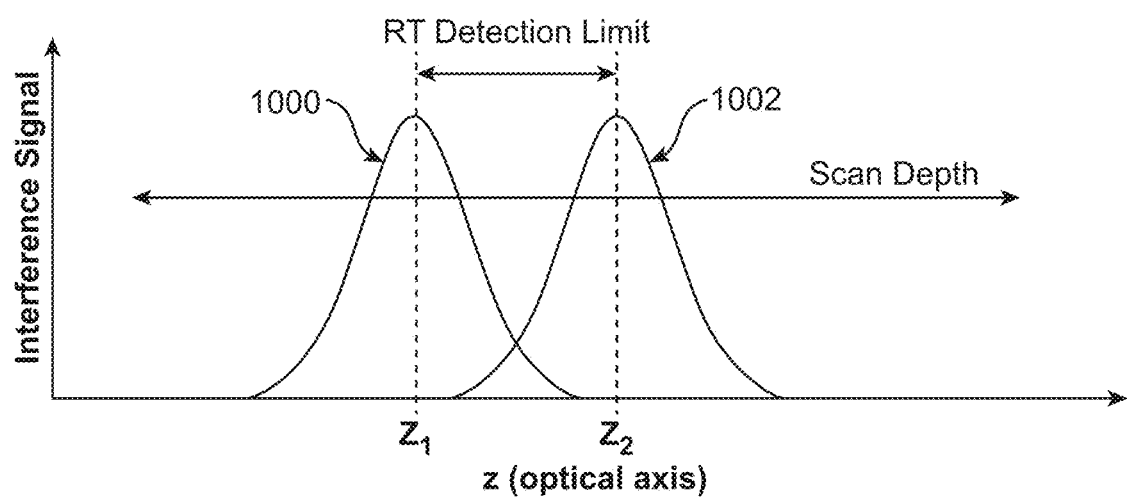
FIG. 10A shows a graphical representation of axial resolution.

FIG. 10A shows a graphical representation of axial resolution. An SS-OCT device used to measure RT or RLT produces a first interference signal 1000 associated with light reflected from a first boundary of a layer of tissue and a second interference signal 1002 associated with light reflected from a second boundary of a layer of tissue. The interference signals 1000 and 1002 are represented in the frequency domain. The first signal has a maximum at an optical path difference $\Delta z_1$. The second signal has a maximum at an optical path difference $\Delta z_2$. Each of the signal peaks has an associated width. The first and second interference signals may be said to be resolved if the two signals do not completely overlap and provide discernable peaks. A maximum overlap occurs when the two signals would no longer be distinguishable if they further overlapped. The distance between the first peak and the second peak at the point of maximum overlap is the axial resolution. The width is inversely related to the range of wavelengths over which the SS-OCT light source is swept. Thus, for SS-OCT devices utilizing a relatively narrow range of wavelengths, the axial resolution can be less than ideal.

For measurements of the RT, the axial resolution should be sufficient to distinguish a first interference signal associated with a first interfacial boundary of a layer of tissue and a second interference signal associated with a second interfacial boundary of the layer of tissue. Since a retina typically has a RT of greater than 150 µm, an SS-OCT device capable of measuring a RT can achieve an axial resolution value of less than about 150 µm.

Figure 10B:
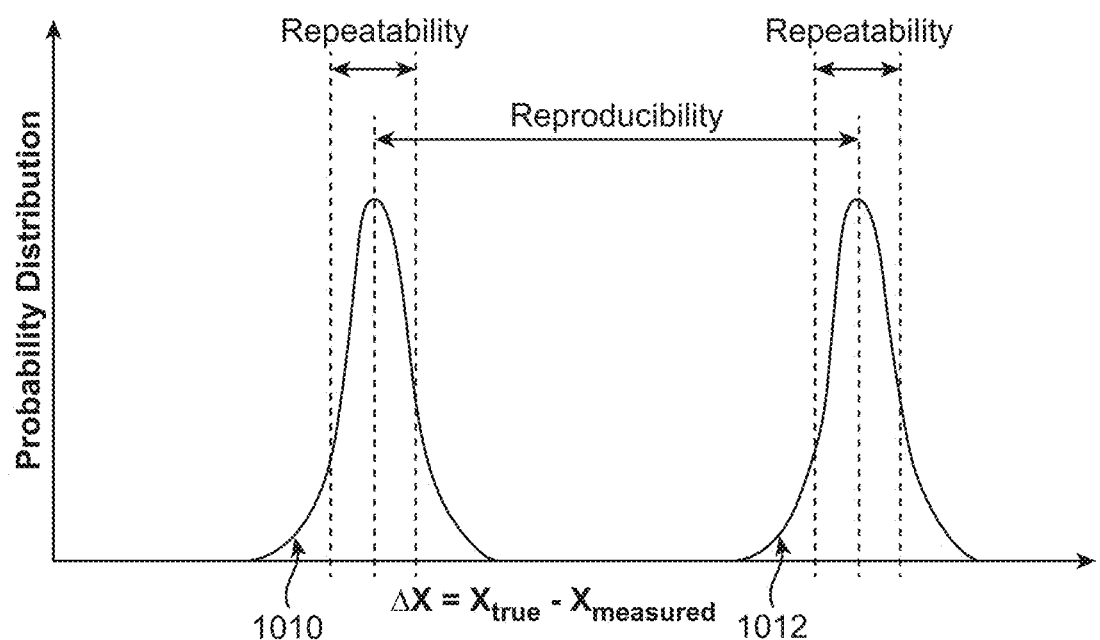
FIG. 10B shows a graphical representation of repeatability and reproducibility.

FIG. 10B shows a graphical representation of repeatability and reproducibility. Repeatability refers to the variation in measurements taken by a single instrument on the same item, under similar conditions, within a short period of time (e.g. within a minute, within an hour, or within a day). Reproducibility refers to the variation in measurements taken by a single instrument on the same sample, under similar conditions but over a longer period of time (e.g. after more than a day, more than a week, more than a month, more than 3 months, or more than 6 months). Repeatability may be quantitatively expressed as the full-width at half maximum (FWHM) value of the distribution of values obtained during repeated measurements by a single instrument, under similar conditions, within the relatively short period of time. Reproducibility may be quantitatively expressed as a difference between the central value of a first distribution of values obtained by a single instrument, under a first set of conditions, conducted within a first short period of time, and the central value of a second distribution of values obtained by the single instrument, under a second set of conditions, conducted within the second short period of time. For measurements of the RT, the combination of repeatability and reproducibility can be used to set tolerances for determining determines whether a change in the measured value of the RT or RLT is due to noise or due to an actual change in the thickness of the retina.

Figure 10C:
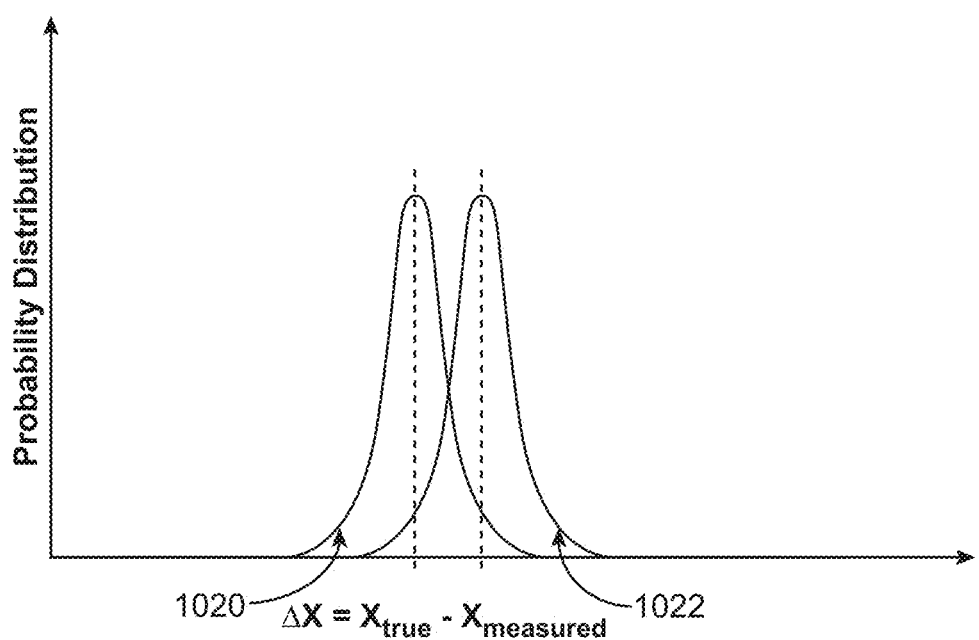
FIG. 10C shows a graphical representation of the repeatability and reproducibility associated with measurements of the RT of a retina that has not exhibited a change in RT.

FIG. 10C shows a graphical representation of the repeatability and reproducibility associated with measurements of the RT or RLT of a retina that has not exhibited a change in RT or RLT. At a first point in time, a measured value of the RT follows a distribution 1020 determined by the repeatability. At a later point in time, a measured value of the RT or RLT is obtained from a distribution 1022, as determined by the repeatability and reproducibility. For a retina which has not exhibited a change in RT or RLT, the two distributions 1020 and 1022 lie within close proximity of one another, such that $\Delta x$ is within the combined repeatability and reproducibility. If however, $\Delta x$ is greater than the combined repeatability and reproducibility an increase in retinal thickness is identified and reported to the patient and health care provider, for example with an alert, as explained more fully in FIG. 10D. In many embodiments, the compact OCT device has a combined repeatability and reproducibility of less than about 35 µm. In some embodiments, the SS-OCT device has a combined repeatability and reproducibility of less than m with a 95% confidence level.

Figure 10D:
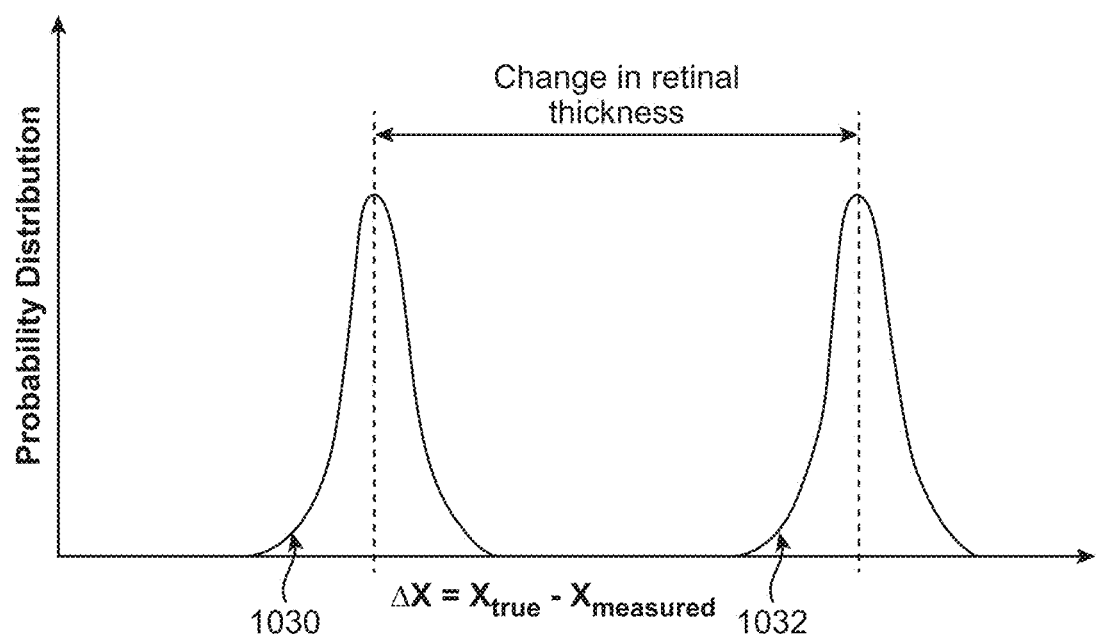
FIG. 10D shows a graphical representation of the repeatability and reproducibility associated with measurements of the RT of a retina that has exhibited a change in RT.

FIG. 10D shows a graphical representation of the repeatability and reproducibility associated with measurements of the RT or RLT of a retina that has exhibited a change in RT or RLT. At a first point in time, a RT or RLT is obtained within a first distribution 1030 determined by the repeatability. At a later point in time, the RT or RLT is obtained within a second distribution 1032, also determined by the repeatability. For a retina which has exhibited a change in RT or RLT, the two distributions 1030 and 1032 no longer lie within close proximity of one another. When the distance between the two distributions 1030 and 1032 exceeds the combination of the repeatability and reproducibility, it may be determined that the RT or RLT has changed. The distance between the two distributions can be determined by determining a difference between the respective means of the two distributions. The system can determine that a change in RT or RLT has occurred when the measured values are separated by more than the combination of the repeatability and reproducibility. For example, this would be approximately 35 µm for a reproducibility of 25 µm and a repeatability of 25 µm. Alternatively, with systematic errors or long-term drift, the combined error could be larger than 35 µm for a reproducibility of 25 µm and a repeatability of 25 µm. Therefore, the peaks of the distributions for a first RT measurement of 150 µm and a second RT measurement of 200 µm would be 50 µm apart. Although the first measurement and the second measurement are shown to have non-overlapping distributions, the methods and apparatuses described herein are capable of determining RT or RLT for partially overlapping distributions of measurements.

In some cases, a measured value of the RT or RLT obtained by the handheld OCT device is compared to a reference measurement. In some embodiments, the reference measurement is obtained from a measurement conducted by a clinical OCT device. In some instances, the reference measurement is obtained during a visit to a patient's health care provider. In some cases, the reference measurement is stored on the handheld OCT device, the patient device (such as a smartphone or other portable electronic device), or the cloud-based storage and communications system. In some embodiments, the reference measurement is used to adjust the measured value from the compact OCT device to account for any systematic errors in the measured value, for example.

Thus, when it is desired to attain measured changes in the RT or RLT, it may be possible to obtain a limit of detection which is substantially better than the attainable axial resolution for OCT imaging set by Equation 1. In some cases, the handheld OCT devices described herein attains a repeatability of approximately 25 µm. In some embodiments, the handheld OCT devices described herein is capable of detecting a change in RT or RLT of approximately 25 µm. In some cases, the handheld OCT devices described herein is capable of detecting a change in RT or RLT of in the range of 10 µm to 40 µm with a confidence better than 95%. In some cases, the handheld OCT devices described herein is capable of detecting a change in RT or RLT of in the range of 20 µm to 30 µm with a confidence better than 95%.

In many embodiments, the compact OCT system is calibrated for a specific patient with a high resolution clinical OCT reference system having a resolution value less than the compact OCT system. For example, the patient can visit an ophthalmologist and the retinal thickness measured with a high resolution ultrasound system at the physician's office. The compact OCT system can be calibrated to the specific patient based on the retinal thickness measured with the clinical reference system. This calibration of the compact OCT system based on the high resolution OCT system can be performed within a day of the high resolution ultrasound system measurement, preferably within about two hours of the clinical high resolution ultrasound measurement, and in many instances while the patient is at the clinic.

In some embodiments, the devices described herein are capable of continued operation after being dropped. In some instances, the devices described herein are capable of withstanding drops with a 95% survival rate during a drop test. In some cases, the drop test consists of dropping a device from 1 foot (0.305 m), 2 feet (0.610 m), 3 feet (0.914 m), and 4 feet (1.219 m). In some embodiments, the devices described herein are capable of continued operation with a change in repeatability of no more than 30 µm following the drop test. In some embodiments, the devices are capable of continued operation with a change in repeatability of no more than 20 m following the drop test. In some embodiments, the devices are capable of continued operation with a change in repeatability of no more than 15 µm following the drop test. In some embodiments, the devices are capable of continued operation with a change in repeatability of no more than 10 µm following the drop test. In some embodiments, the devices are capable of continued operation with a change in repeatability of no more than 5 µm following the drop test.

Figure 11:
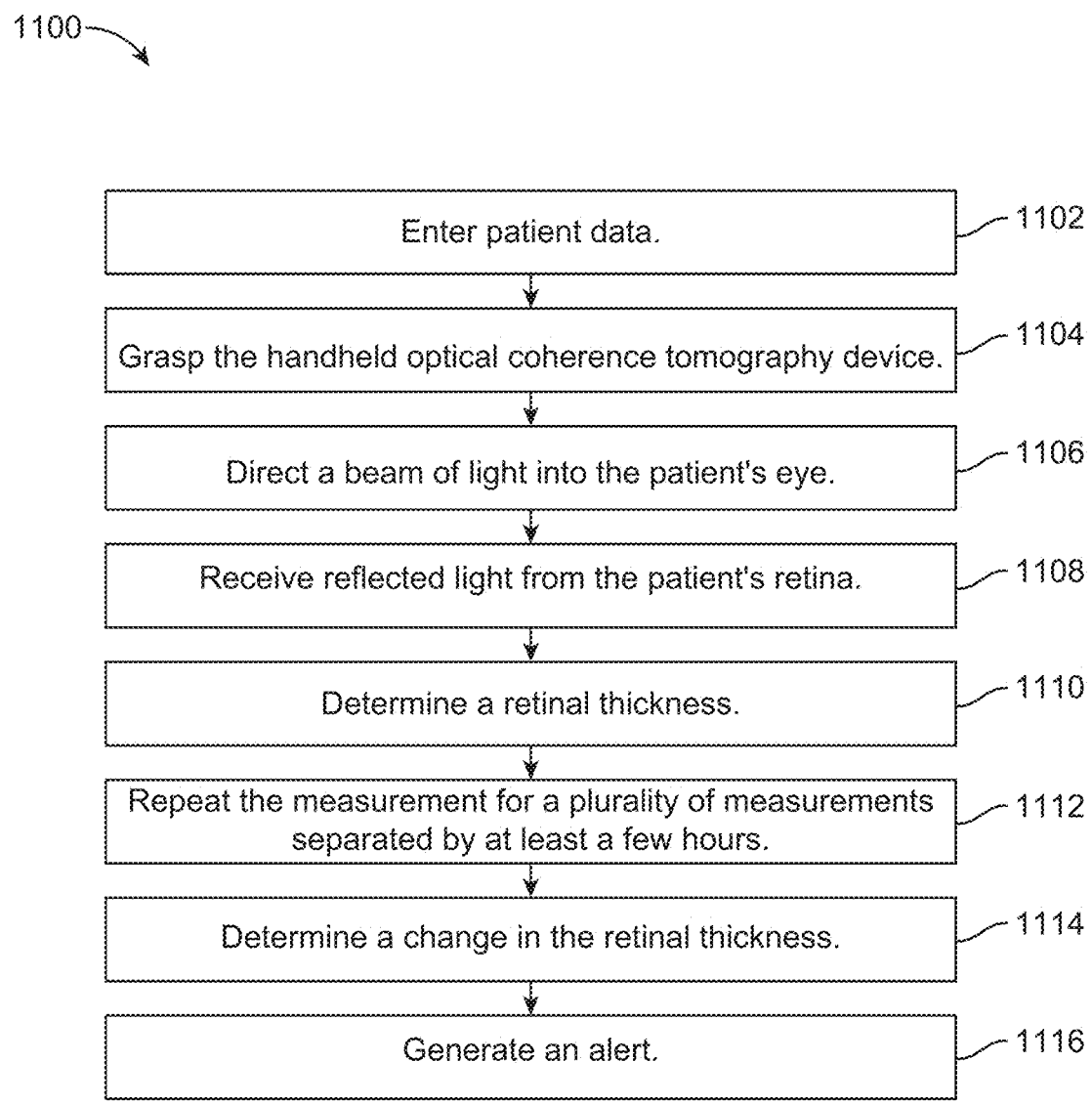
FIG. 11 is a flowchart of a method for conducting repeated measurements of a patient's RT over time and noting changes that may correspond to adverse outcomes.

FIG. 11 is a flowchart of a method for conducting repeated measurements of a patient's retinal thickness (RT) over time and noting changes that may correspond to undesirable outcomes. The method 1100 consists of entering patient data, grasping a handheld OCT device, directing a beam of light into the patient's eye, receiving reflected light from the patient's retina, determining a retinal thickness, repeating the measurement for a plurality of measurements separated by at least a few hours, determining a change in the RT, and generating an alert.

In step 1102, patient data is entered into the handheld OCT device described herein. In some cases, the patient data includes any of the patient's name, age, gender, height, weight, current ophthalmological issues, and current medical issues.

In step 1104, the patient grasps the handheld OCT device described herein. The patient looks into the handheld OCT device.

In step 1106, the handheld OCT device directs a beam of light into the patient's eye. The light is reflected from boundaries of the various layers of the patient's retina.

In step 1108, the handheld OCT receives light reflected from the various layers of the patient's retina. The reflected light forms an interference signal which is detected by a photodetector. In some cases, the interference signal is generated by the interference of the reflected light with light which has traversed the reference arms of the handheld OCT device. In some cases, the interference signal is generated by the interference between light reflected from two or more boundaries of the various layers of the retina. The handheld OCT device varies the wavelength of light directed to the eye and records an interference signal for each wavelength.

In step 1110, a patient's RT or RLT is determined. In some cases, the RT or RLT is determined by a mathematical analysis of the OCT signal. For instance, the RT or RLT may be determined from a fast Fourier transformation of the OCT signal. The RT or RLT may be determined from any other frequency analysis of the OCT signal. The RT or RLT may be determined by comparing the frequency content of the OCT signal to a calibration curve which maps RT or RLT to frequency. In some embodiments, the calibration curve is generic to all patients. In some instances, the calibration curve is specific to an individual patient.

In step 1112, the measurement is repeated for a plurality of measurements separated by at least a few hours. For each measurement, the steps 1102, 1104, 1106, 1108, and 1110 are repeated.

In step 1114, a change in the RT or RLT is determined. In some cases, the value of the RT or RLT determined in the most recent measurement is compared to any previous measurement. In some embodiments, the change in the value of the RT or RLT is recorded and tracked over the course of many measurements.

In step 1116, an alert is generated if the RT or RLT has changed significantly or if the RT or RLT falls outside of a normal or healthy range. In some cases, the alert comprises a notification displayed on the mobile patient device described herein. In some embodiments, the alert may comprise a notification sent to the patient's physician or other medical provider, as described herein.

In some cases, a first RT or RLT is measured with a handheld OCT device within 24 hours of a visit to an ophthalmologist. In some embodiments, a second RT or RLT is measured within a range from one day to twenty days after the first measurement. In some instances, the RT or RLT are measured each day for a plurality of days within a range from about 5 days to about 20 days. In some cases, the RT or RLT are measured more often than once per day. In some embodiments, the RT or RLT are measured for a period longer than 20 days. A change in RT or RLT is determined in response to the baseline thickness and the plurality of later thicknesses. In some cases, the change in RT or RLT is measured with a confidence interval of at least 90%, at least 95%, or at least 99%.

Figure 12:
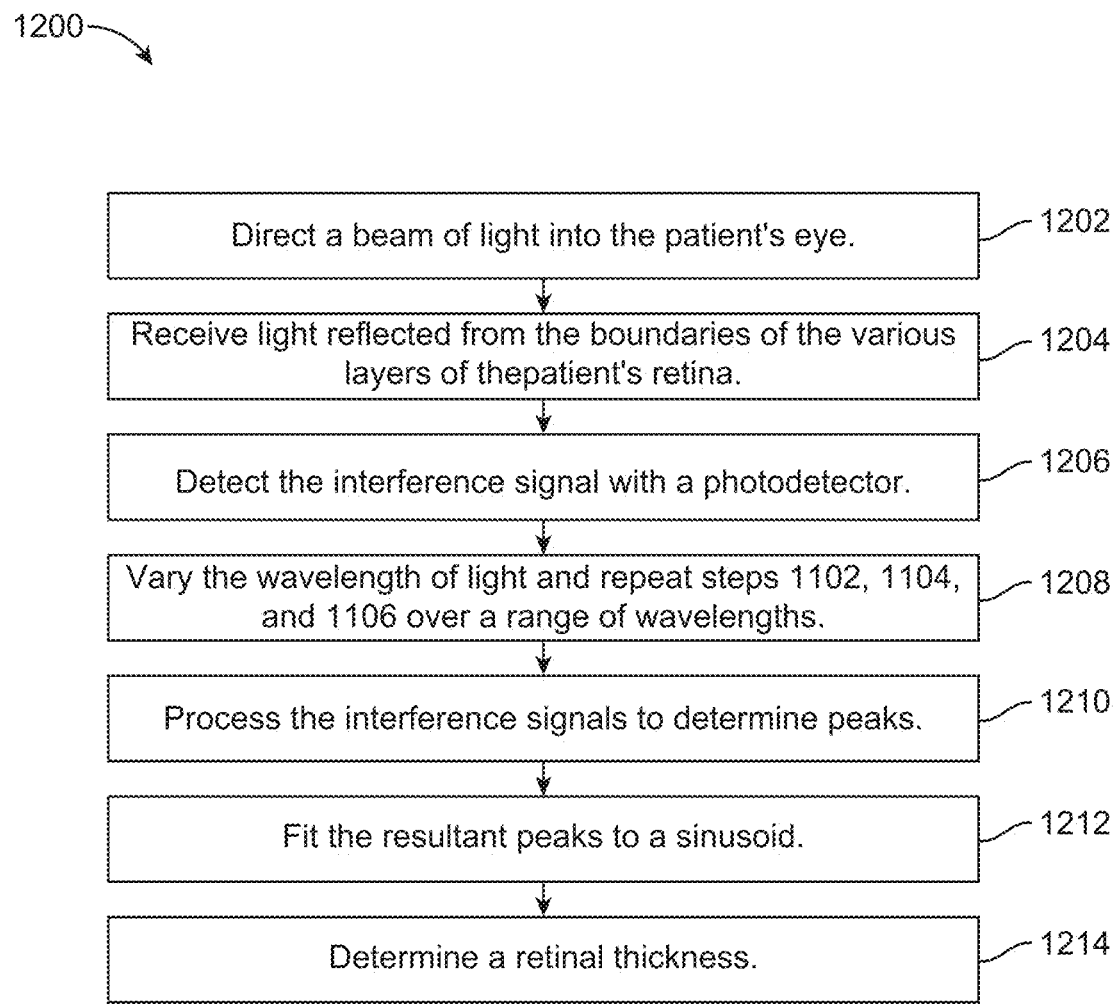
FIG. 12 shows a flowchart of a method for determining the RT from a measurement using the handheld OCT device.

FIG. 12 shows a flowchart of a method for determining the RT from a measurement using the handheld OCT device. The method 1200 comprises the steps of directing a light beam to the retina, generating an interference signal, capturing the interference pattern with a detector, varying the wavelength of the light directed to the retina, processing the interference signals to determine peaks, fitting the resultant peaks to a sinusoid, and determining a RT or RLT.

In step 1202, the handheld OCT device directs a beam of light into the patient's eye. The light is reflected from boundaries of the various layers of the patient's retina.

In step 1204, the handheld OCT receives light reflected from the boundaries of the various layers of the patient's retina. The reflected light forms an interference signal. In some cases, the interference signal is generated by the interference of the reflected light with light which has traversed the reference arms of the handheld OCT device. In some cases, the interference signal is generated by the interference between light reflected from two or more boundaries of the various layers of the retina.

In step 1206, the interference signal is detected by a photodetector.

In step 1208, the handheld OCT device varies the wavelength of light directed to the retina. For each wavelength, the steps 1202, 1204, and 1206 are repeated. An interference signal is recorded for each wavelength.

In step 1210, the interference signals are processed to determine peaks. In some cases, the peaks correspond to interference maxima between light reflected from the various layers of the retina and light which has traversed a reference arm of the handheld OCT device. In some cases, the peaks correspond to interference maxima between light reflected from the boundaries of the various layers of the retina and light which has traversed the reference arms of the handheld OCT device. In some cases, the peaks correspond to interference maxima between light reflected from two or more boundaries of the various layers of the retina.

In step 1212, the resultant peaks are fit to a sinusoid. In some cases, the fitting is via a non-linear least squares fitting. In some embodiments, the fitting is via any other fitting method known to one having skill in the art.

In step 1214, the RT or RLT is determined. In some cases, the RT or RLT is determined by extracting the frequency of the fitted sinusoid. In some embodiments, the RT or RLT is determined by comparing the frequency content of the OCT signal to a calibration curve which maps RT to frequency. In some instances, the calibration curve is generic to all patients. In some cases, the calibration curve is specific to an individual patient.

A person of ordinary skill in the art will recognize many variations, alterations and adaptations based on the disclosure provided herein. For example, the order of the steps of the methods 1100 and/or 1200 can be changed, some of the steps removed, some of the steps duplicated, and additional steps added as appropriate. The methods of 1100 and 1200 may be combined. Some of the steps may comprise substeps. Some of the steps may be automated and some of the steps may be manual. The processor as described herein may comprise one or more instructions to perform at least a portion of one or more steps of the methods 1100 and/or 1200.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 13:
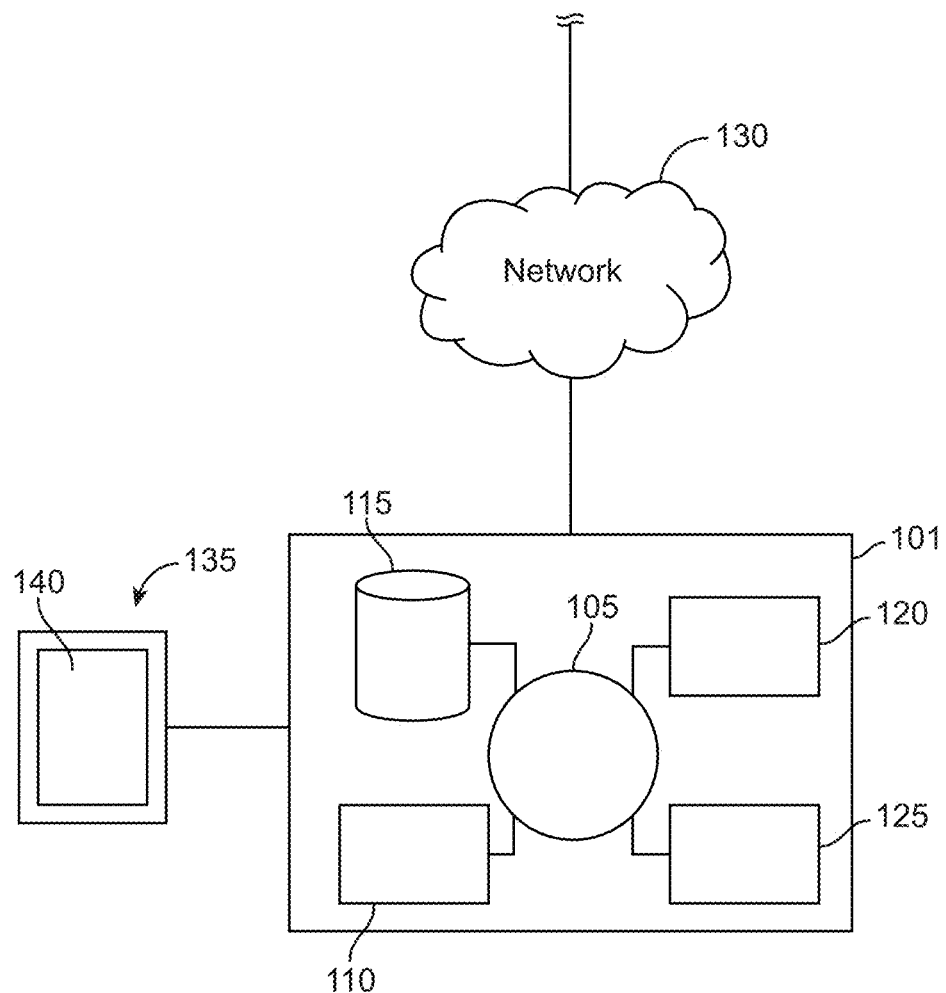
FIG. 13 shows an exemplary digital processing device programmed or otherwise configured to determine a RT or RLT.

Referring to FIG. 13, in a particular embodiment, an exemplary digital processing device 1301 is programmed or otherwise configured to determine a RT or RLT. The device 1301 can regulate various aspects of the RT or RLT determination of the present disclosure, such as, for example, performing processing steps. In this embodiment, the digital processing device 1301 includes a central processing unit (CPU, also "processor" and "computer processor" herein) 1305, which can be a single core or multi core processor, or a plurality of processors for parallel processing. The digital processing device 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The digital processing device 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the device 1301, can implement a peer-to-peer network, which may enable devices coupled to the device 1301 to behave as a client or a server.

Continuing to refer to FIG. 13, the CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and write back. The CPU 1305 can be part of a circuit, such as an integrated circuit. One or more other components of the device 1301 can be included in the circuit. In some cases, the circuit is an application specific integrated circuit (ASIC) or a field programmable gate array (FPGA).

Continuing to refer to FIG. 13, the storage unit 1315 can store files, such as drivers, libraries and saved programs. The storage unit 1315 can store user data, e.g., user preferences and user programs. The digital processing device 1301 in some cases can include one or more additional data storage units that are external, such as located on a remote server that is in communication through an intranet or the Internet.

Continuing to refer to FIG. 13, the digital processing device 1301 can communicate with one or more remote computer systems through the network 1330. For instance, the device 1301 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1301, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 105. In some situations, the electronic storage unit 1315 can be precluded, and machine-executable instructions are stored on memory 1310.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some embodiments, a computer program includes one or more executable complied applications.

Web Browser Plug-in

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB.NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple Safari®, Palm Blazer, PalmR WebOS® Browser, Mozilla Firefox® for mobile, Microsoft® Internet Explorer Mobile, Amazon Kindle Basic Web, Nokia® Browser, Opera Software® Opera Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Figure 20A:
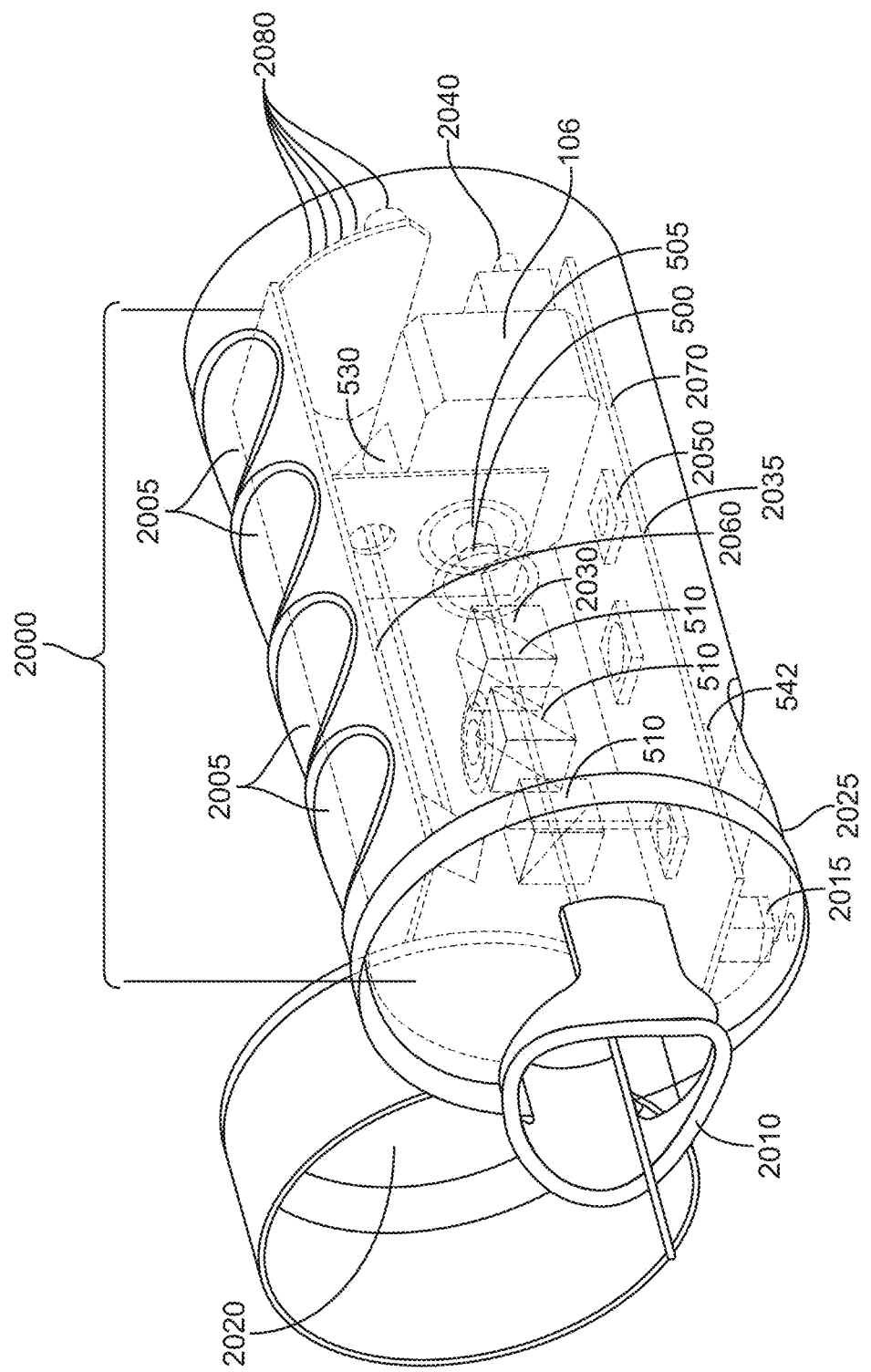
FIG. 20A shows a diagram of a handheld OCT system with an eye adapter.

FIG. 20A shows a diagram of a handheld OCT system with an eye adapter. In some cases, the system comprises a main body 2000. In some embodiments, the main body features a surface adapted to provide an ergonomic grip of the system. In some instances, the surface adapted to provide an ergonomic grip comprises one or more finger holds 2005. In some cases, the system further comprises a measurement end with an adapter 2010 configured to interface the orbital of a user's eye. In some embodiments, the system further comprises a detector which detects the orientation of the system and determines whether the user's left eye or right eye is being measured. In some instances, the system comprises a cap 2020. In some cases, the cap is utilized to cover an eye not being measured. For instance, when the left eye is being measured, the cap covers the right eye. When the right eye is being measured, the cap covers the left eye. In some embodiments, when neither eye is being measured, the cap is placed over the measurement end of the system in order to protect system components from damage.

In some cases, within the main body, the system comprises optics 104. In some embodiments, the system comprises a laser source 500. In some instances, the laser source directs laser light to a collimating lens 505. In some cases, the collimating lens shapes the laser source into a collimated beam of light. In some embodiments, the laser light is directed to a beamsplitter 2030. In some instances, the beamsplitter 2030 directs a portion of the laser light to an optical power meter 2035. In some cases, the optical power meter makes continuous measurements of the emitted laser power, allowing for correction of OCT signals based on the measured power or for the implementation of optical feedback techniques. In some embodiments, the portion of light that passes through the beamsplitter 2030 without being directed to the optical power meter impinges upon one or more beamsplitters 510. In some instances, the one or more beamsplitters 510 direct a portion of the light to a user's eye and another portion of the light to a reference mirror 530. In some cases, the reference mirror comprises a reference surface that is built into the main body of the system. In some embodiments, the system further comprises a detector 542 for detecting OCT signals.

In some embodiments, the system comprises a battery 106. In some instances, the battery is a rechargeable battery. In some cases, the battery is a lithium ion battery. In some embodiments, the battery is a nickel metal hydride battery. In some instances, the battery is a nickel cadmium battery. In some instances, the battery is operatively coupled to a charging device 2040. In some cases, the charging device is a connective charging device. The charging device may be any connective charging device as is known to one having skill in the art. In some cases, the charging device is an inductively coupled charging device. The charging device may be any inductively coupled charging device as is known to one having skill in the art.

In some instances, wireless communication circuitry and a processor as described herein are coupled to the battery to power the compact OCT system and acquire OCT data and transmit the data wirelessly.

In some cases, the system comprises additional components to allow proper operation of the system by a user. In some embodiments, the system comprises an orientation or motion sensor 2050. In some instances, the orientation or motion sensor comprises a gyroscope for measuring an orientation of the device to determine which eye is measured. In some cases, the orientation or motion sensor comprises an accelerometer for measuring a movement of the device. In some embodiments, the orientation or motion sensor comprises any orientation or motion sensor as is known to one having skill in the art. In some instances, the system comprises a visual fixation target 2060 that is viewed when the compact OCT system measures the retina. In some cases, the system comprises a mechanical feature 2070 for providing electrical safety. In some embodiments, the system comprises one or more status indicators 2080.

FIG. 20B shows a handheld OCT system adapted to measure a right eye or a left eye. When operated to provide a right eye measurement, the handheld OCT system 100 is operated in a configuration 2020a having the eye cap 2020 positioned to the left side of a measurement end of the handheld OCT system. When operated to provide a left eye measurement, the handheld OCT system is operated in a configuration 2020b having the eye cap to the right side of a measurement end of the handheld OCT system. When neither eye is being measured, the handheld OCT system is operated in a configuration 2020c having the eye cap positioned to cover the measurement end of the handheld OCT system. In this configuration, the eye cap provides protection of the internal components of the handheld OCT system when the system is not in use. The eye cap is transitioned from the configuration 2020a to the configuration 2020b by a 180 degree rotation of the eye cap. In some cases, the handheld OCT system comprises a switch that detects which eye is to be examined using the OCT system.

Figure 20C:
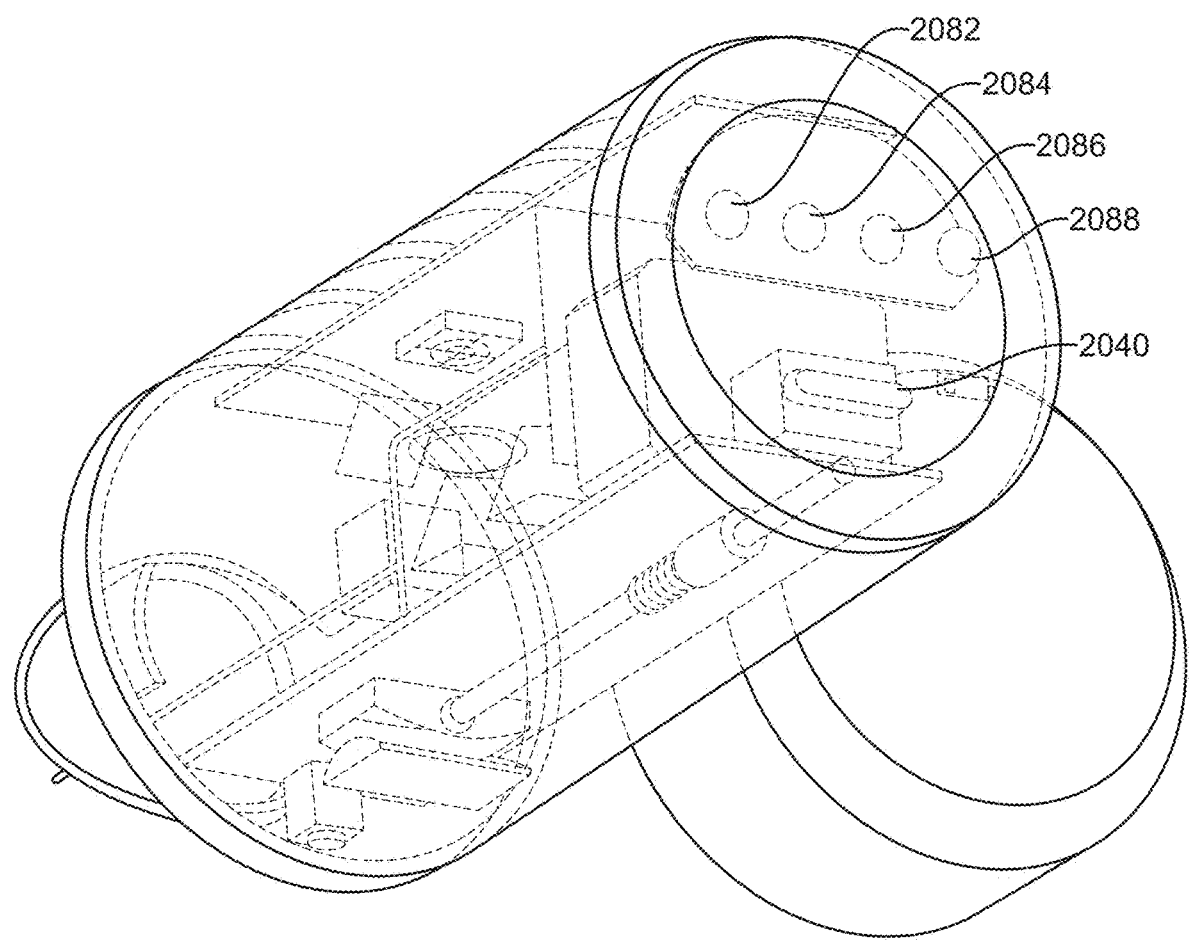
FIG. 20C shows a handheld OCT system with indicator lights and communications adapters.

FIG. 20C shows a handheld OCT system with indicator lights and power adapter. In some cases, the end of the handheld OCT device opposite the measurement end comprises one or more visual vindicators 2080. In some embodiments, the visual indicators comprise light sources. In some instances, the light sources are light emitting diodes (LEDs). In some cases, the visual indicators comprise a first visual indicator 2082 to indicate whether or not the handheld OCT device is in operation. In some embodiments, the visual indicators comprise a second visual indicator 2084 to indicate whether or not the handheld OCT device is utilizing battery power. In some instances, the visual indicators comprise a third visual indicator 2086 to indicate whether or not the handheld OCT device is utilizing an external power source. In some cases, the visual indicators comprise a fourth visual indicator 2088 to indicate whether or not the handheld OCT device is not suitable for use. In some embodiments, the end of the handheld OCT device opposite the measurement end comprises an adapter 2040 to receive electrical power.

Figure 20D:
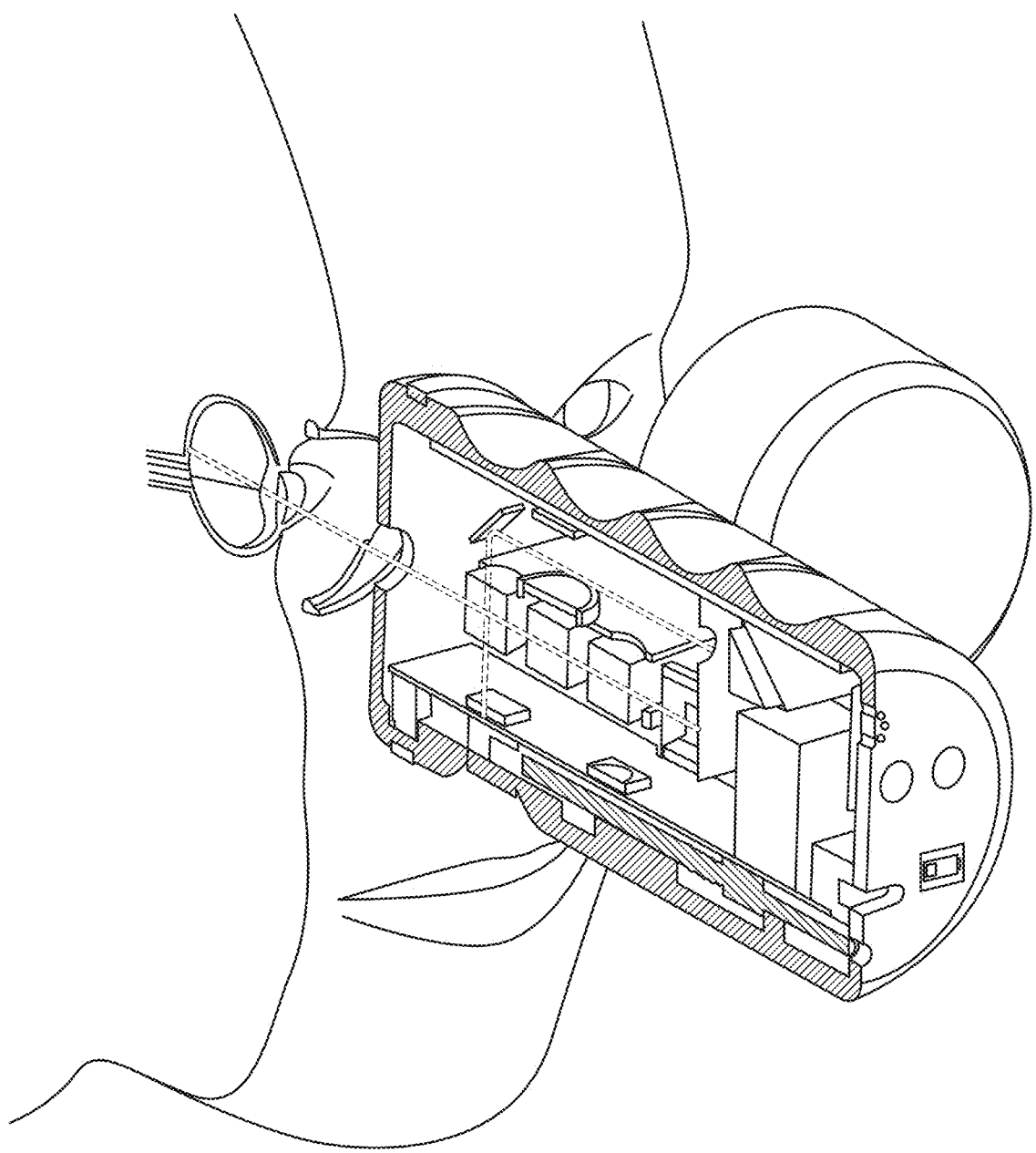
FIG. 20D shows a handheld OCT placed proximate to an eye to provide an OCT measurement.

FIG. 20D shows a handheld OCT placed proximate to an eye to provide an OCT measurement. In some cases, the measurement end of the handheld OCT system is shaped to conform to an eye socket. In some embodiments, the eye cap is positioned to cover the eye that is not being measured. In some instances, the handheld OCT system directs light into the eye in order to obtain an OCT measurement.

In some cases, the handheld OCT device is configured to obtain information sufficient to determine a single measurement of a RT or RLT in a period of time no more than that associated with motion of the eye relative to the device. In some embodiments, the motion of the eye relative to the device is due to motion of the user's hand while holding the device. In some cases, the motion of the eye relative to the device is due to motion of the eye. In some instances, the handheld OCT device is configured to obtain a measurement of a RT or RLT in a period of time no more than 100 ms, no more than 50 ms, or no more than 10 ms. In some cases, the handheld OCT device is configured to obtain a measurements of a RT or RLT in a period of time that lies within a range defined by any two of the preceding values.

Figure 21:
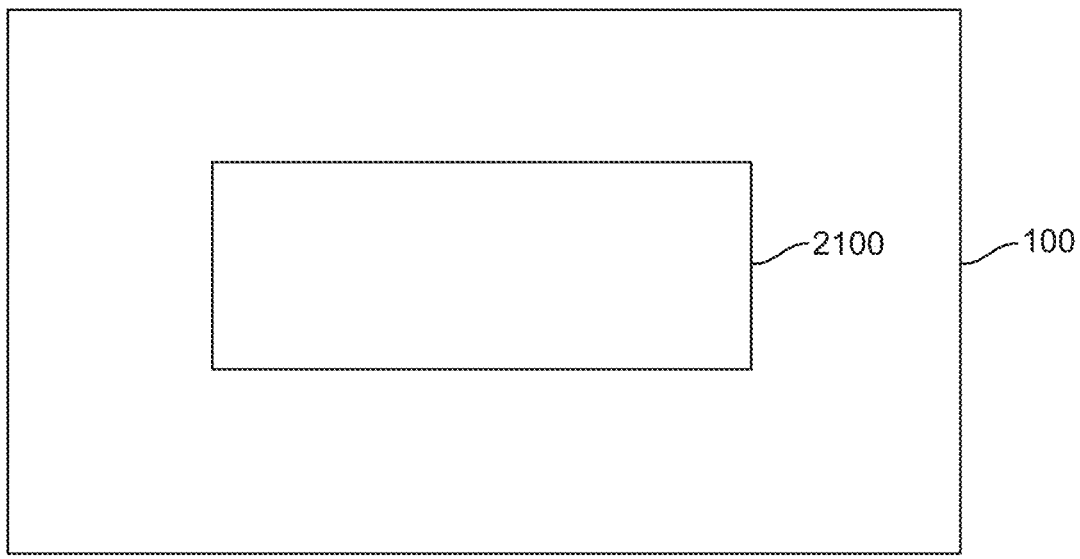
FIG. 21 shows a calibration kit for a handheld OCT device.

FIG. 21 shows a calibration kit for a handheld OCT device. In some cases, the handheld OCT device 100 comprises a calibration fixture 2100. In some embodiments, the calibration fixture is located on an inside surface of the cap 2020 of FIG. 20.

Figure 22:
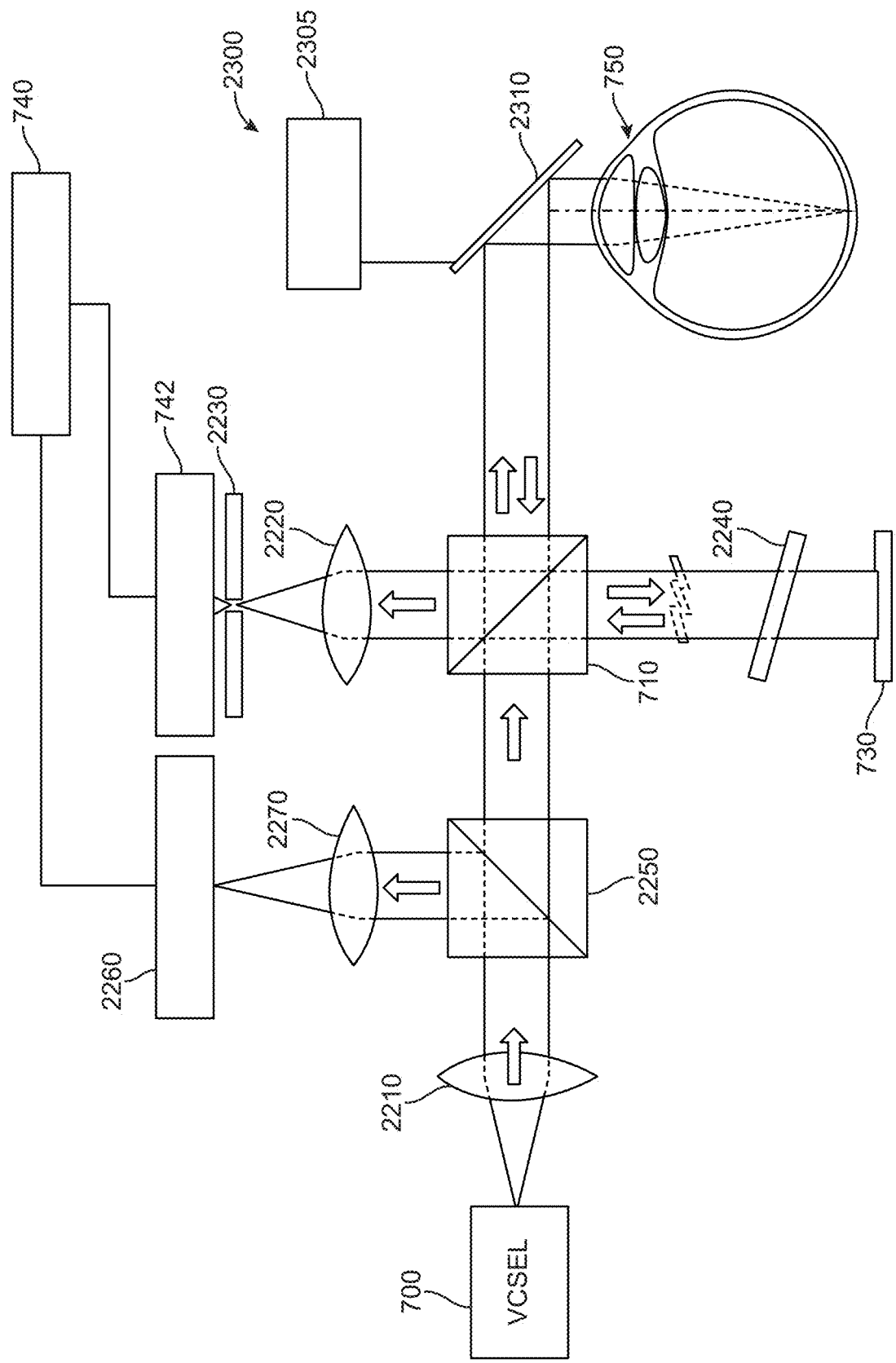
FIG. 22 shows a schematic for a SS-OCT device utilizing a scanning mechanism, in accordance with some embodiments.

FIG. 22 shows a schematic for the optics of a swept source optical coherence tomography (SS-OCT) device utilizing a scanning mechanism, in accordance with some embodiments. The optics 102 comprises a light source 700, a first beamsplitter 710, and a reference mirror 730 as described herein. The first processing unit 740 is coupled to a detector 742 to detect the swept source interference signal. The first processing unit may comprise a first photodetector 742 as described herein and a first signal processing unit 742, as described herein.

The optics may further comprise a collimating optical element 2210. The collimating optical element may comprise a collimating lens, for example. The collimating optical element may collimate light emitted from the light source prior to the interaction of the light with other optical elements. The optics may further comprise a lens 2220 that focuses an interference signal onto the photodetector 742. The optics may further comprise a pinhole 2230 through which light focused by the first lens is passed prior to detection by the first processing unit. The optics may further comprise a neutral density filter 2240 that reduces the intensity of light incident on the reference mirror.

The optics may further comprise a beamsplitter 2250. The beamsplitter may comprise any beamsplitter as described herein. The second beamsplitter may direct a portion of the light emitted by the light source to a second photodetector 2260, which may be similar to the first processing unit 740, or other circuitry configured to control the amount of energy emitted by the VCSEL. The second processing unit may comprise a second photodetector (not shown) and a second signal processing unit (not shown), which may be similar to the first photodetector and first signal processing unit. The second processing unit may detect fluctuations in the intensity of light emitted by the light source. The detected fluctuations in the intensity of light emitted by the light source may be utilized to correct the SS-OCT signal detected by the first processing unit for errors associated with fluctuations in the intensity of light emitted by the light source. The optics may further comprise a lens 2270 that focuses the portion of the light emitted by the light source onto the second photodetector 2260.

The light source 700 may be configured in many ways. For example, light source 700 may comprise a swept source VCSEL driven as described herein. Alternatively or in combination, the VCSEL may be cooled in order to increase the sweep range. For example, the VCSEL may be cooled with a chiller such as a thermo electric chiller in order to allow the VCSEL to be driven over a broader sweep range. The VCSEL may comprise a MEMS actuator coupled to a mirror in order to increase a range of swept wavelengths to about 20 nm or more. The VCSEL may be coupled to an external mirror and an actuator to change a position of the mirror in order to increase the range of swept wavelengths, for example. The VCSEL coupled to movable mirror may be swept over a range of wavelengths within a range from about 10 to 30 nm, or more.

Table 2 shows sweep ranges and resolutions that may be obtained for 10 to 30 nm of sweeping of the VCSEL of the compact SS-OCT system as described herein.

| Wavelength Range (nm) | Axial Resolution (μm) |
|---|---|
| 10 | 31.9 |
| 11 | 29.0 |
| 12 | 26.6 |
| 13 | 24.5 |
| 14 | 22.8 |
| 15 | 21.3 |
| 16 | 19.9 |
| 17 | 18.8 |
| 18 | 17.7 |
| 19 | 16.8 |
| 20 | 15.9 |
| 21 | 15.2 |
| 22 | 14.5 |
| 23 | 13.9 |
| 24 | 13.3 |
| 25 | 12.8 |
| 26 | 12.3 |
| 26 | 12.3 |
| 28 | 11.4 |
| 29 | 11.0 |
| 30 | 10.6 |

The light source 700 may be swept by an amount within a range defined by any two values in Table 1 and Table 2, for example over a range from 9 nm to 20 nm, so as to provide a corresponding resolution, for example a corresponding resolution within a range from 35.4 um to 15.9 um.

In some embodiments, the compact SS-OCT system further comprises a scanning mechanism 2300. The scanning mechanism 2300 may comprise an actuator 2305 and a mirror 2310, which is deflected by the actuator in order to scan the light beam on the eye. The actuator 2305 may comprise any actuator known to one of ordinary skill in the art, such as a microelectromechanical system (MEMS) actuator, a galvanometer, or a piezo electric crystal, for example. The scanning mechanism 2300 may be coupled to the control unit as described herein.

Figures 23A, 23B:
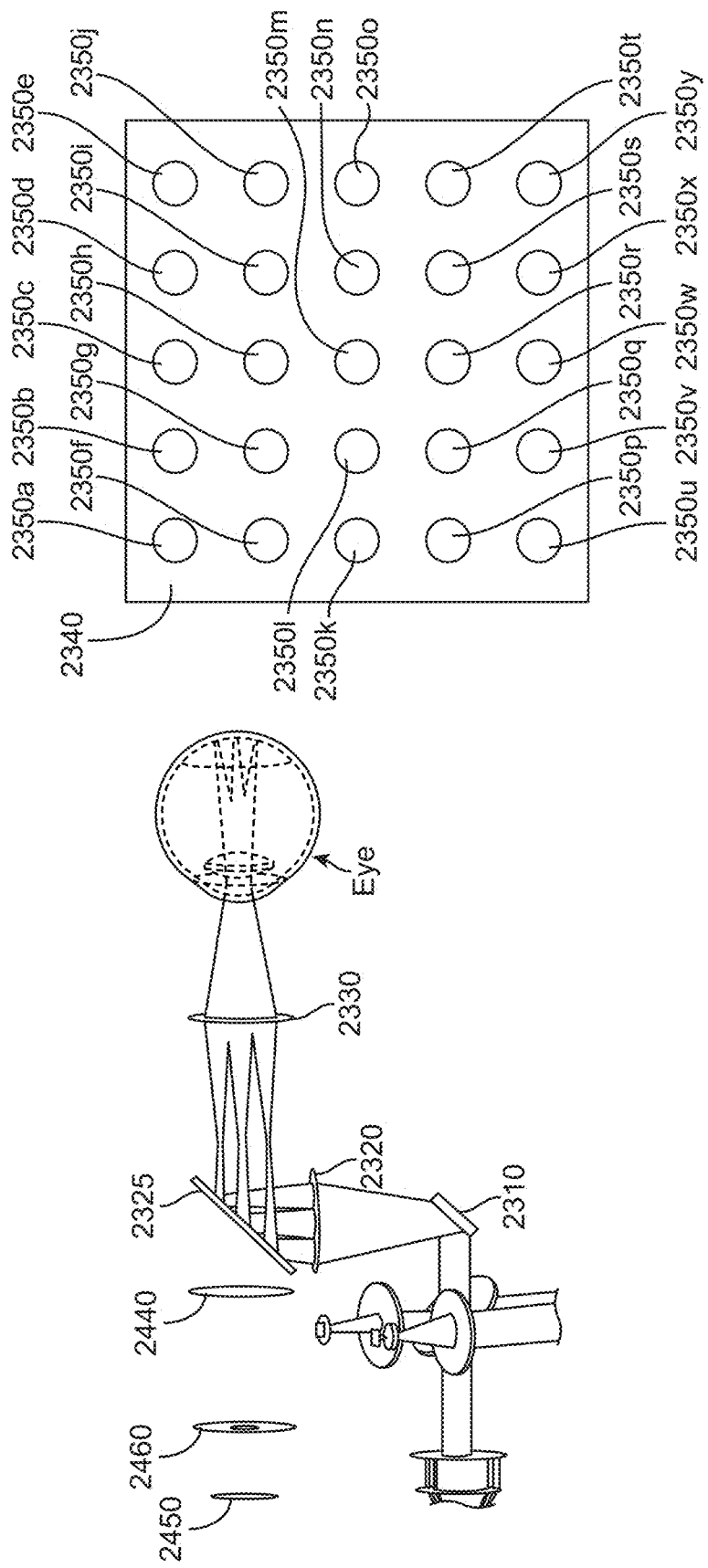
FIG. 23A shows a schematic for a scanning mechanism, in accordance with some embodiments.
FIG. 23B shows an array of retinal layer thickness measurement sites, in accordance with some embodiments.

FIG. 23A shows scanning mechanism 2300 optically coupled to an eye with the compact SS-OCT system, in accordance with some embodiments. The scanning mechanism 2300 may comprise a first scanning optical element, such as a mirror 2310, and a telescope system comprising a first telescope lens 2320 and a second telescope lens 2330. The telescope system may comprise a 4-f telescope system, for example. The telescope system may further comprise a mirror 2325 to deflect the scanned light beam toward the eye. The second telescope lens 2330 may comprise an aspheric lens.

In some embodiments, the mirror 2325 couples an optical path of a patient visualization system with the optical path of the scanned light beam. In some cases, the mirror 2325 comprises a shortpass mirror. The patient visualization system may comprise a lens 2440, an aperture 2460 and a lens 2450, is further described in FIG. 24.

The scanning optical element may comprise any type of scanning optical element known to one of ordinary skill in the art, such as mirror, a prism, a polygonal mirror, or a lens, for example. The scanning element may be a galvanometer. The scanning element may permit the measurement of a RT or RLT at more than one location on a retina by scanning the measurement beam across a plurality of locations on the retina.

FIG. 23B shows an array of retinal thickness (RT) or retinal layer thickness (RLT) measurement sites, in accordance with some embodiments. The scanning mechanism described herein may direct measurement light to a plurality of measurement locations 2350*a*, 2350*b*, 2350*c*, 2350*d*, 2350*e*, 2350*f*, 2350*g*, 2350*h*, 2350*i*, 2350*j*, 2350*k*, 23501, 2350*m*, 2350*n*, 2350*o*, 2350*p*, 2350*q*, 2350*r*, 2350*s*, 2350*t*, 2350*u*, 2350*v*, 2350*w*, 2350*x*, and 2350*y* on a retina 2340. Although 25 measurement locations are depicted, the scanning mechanism may direct the measurement light to 2 or more measurement locations, 5 or more measurement locations, 10 or more measurement locations, 20 or more measurement locations, 50 or more measurement locations, 100 or more measurement locations, 200 or more measurement locations, 500 or more measurement locations, or 1000 or more measurement locations. A measurement of a RT or RLT may be obtained at each of the measurement locations to obtain a plurality of RT or RLT measurements. The plurality of RT or RLT measurements may allow the construction of a spatial map of RT or RLT measurements. The plurality of RT or RLT measurements may span a first distance on the retina in a first direction and a second distance on the retina in a second direction transverse to the first direction. The first distance may comprise a length of less than 0.5 mm, less than 1.0 mm, less than 1.5 mm, less than 2.0 mm, less than 2.5 mm, less than 3.0 mm, less than 3.5 mm, less than 4.0 mm, less than 4.5 mm, or less than 5.0 mm. The second distance may comprise a length of less than 0.5 mm, less than 1.0 mm, less than 1.5 mm, less than 2.0 mm, less than 2.5 mm, less than 3.0 mm, less than 3.5 mm, less than 4.0 mm, less than 4.5 mm, or less than 5.0 mm.

Figure 24:
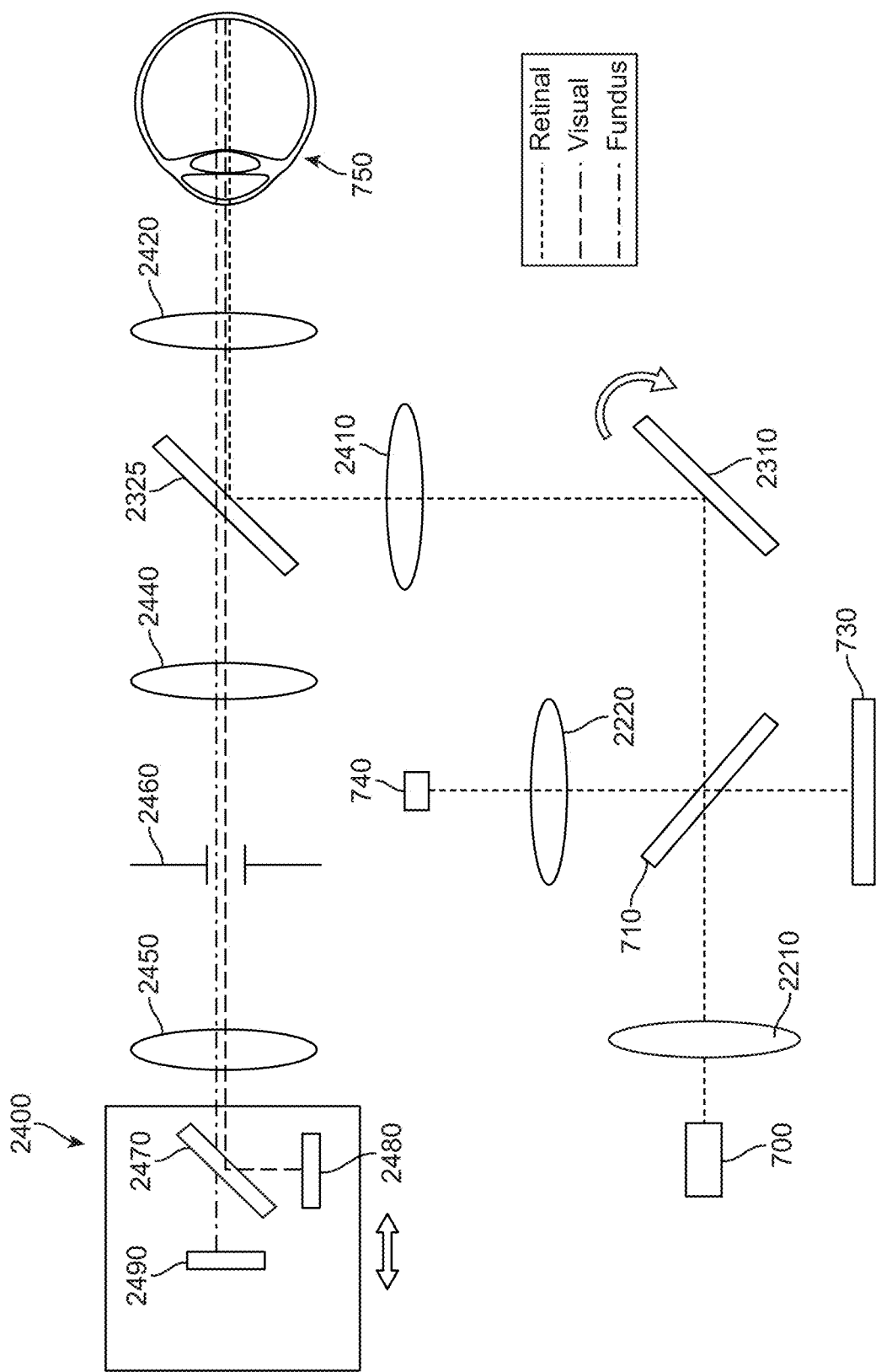
FIG. 24 shows a schematic for a SS-OCT device utilizing a scanning mechanism and one or more cameras, in accordance with some embodiments.

FIG. 24 shows a schematic for the optics of a compact swept source optical coherence tomography (SS-OCT) device comprising a patient visualization system 2400. The patient visualization system 2400 may comprise a camera to view the fundus and a display to measure patient visual acuity. The display to measure patient visual acuity may configured for the patient to fixate on a viewing target, for example by displaying a small object visible to the patient. The optics 102 may comprise a light source 700, a collimating optical element 2210, a first beamsplitter 710, a reference mirror 730, and a first lens 2200 coupled to photodetector 742 as described herein.

The optics may further comprise a scanning mechanism as described herein. The scanning mechanism may comprise a scanning optical element 2310 and a telescope system comprising a first telescope lens 2320 and a second telescope lens 2330. The optics may further comprise mirror 2435, such as a hot mirror. The hot mirror may be configured to reflect infrared light. The hot mirror may be configured to transmit visible light. The hot mirror may be configured to reflect OCT measurement light to an eye and to transmit visible light to the patient in order to display images shown on the display to the subject and to image the fundus with a detector.

The visual function measurement apparatus of the compact SS-OCT system may comprise a Badal lens and imaging system to compensate for the refraction of the patient. The lens 2450 may be coupled to an actuator to move the lens along the optical axis to correct for refractive error of the subject, in order to bring the image of the fundus into focus on the detector array and to bring the image on the display as seen by the subject into focus. The Badal lens may be configured to provide a virtual image seen by the patient with a constant viewing angle, and lens may provide a refractive error compensation that is linear with microdisplay displacement (e.g. +−5 diopter).

The visual function measurement apparatus presents one or more visual cues to a patient.

The compact SS-OCT system may further comprise one or more camera apparatuses, such as a fundus camera. The compact SS-OCT system may comprise a visual camera apparatus configured to measure an anterior portion of the eye, for example. The optics coupled to the fundus camera and visual display may further comprise a telescope comprising a first telescope lens 2440 and a second telescope lens 2450. The optics may further comprise an aperture 2460 comprising a stop. The stop may comprise a ring stop, for example. The optics may further comprise a second beamsplitter 2470. The second beamsplitter may direct a portion of incident from the eye light toward a detector array 2480 and a portion of incident light from a micro-display 2490 toward the eye for patient visualization. The detector array may be a charge coupled device (CCD). The detector array may be a complementary metal oxide semiconductor (CMOS) detector array, for example.

The visual camera apparatus may obtain images of an eye while the OCT system obtains RT or RLT measurements of the eye. The visual camera apparatus may obtain images of an eye before, during, or after the OCT system obtains RT or RLT measurements of the eye as described herein. The fundus camera apparatus may obtain images of a fundus of an eye while the OCT system obtains RT or RLT measurements of the eye. The fundus camera apparatus may obtain images of an eye before, during, or after the OCT system obtains RT or RLT measurements of the eye. The images of the fundus obtained by the fundus camera apparatus may be subjected to image processing to determine whether and by how much an OCT measurement location has moved between two consecutive measurements (such as due to voluntary or involuntary motion of the eye or due to voluntary or involuntary motion of the handheld OCT system). The scanning of the OCT beam may be adjusted in response to eye movements in order to compensate for eye movements.

Figure 25:
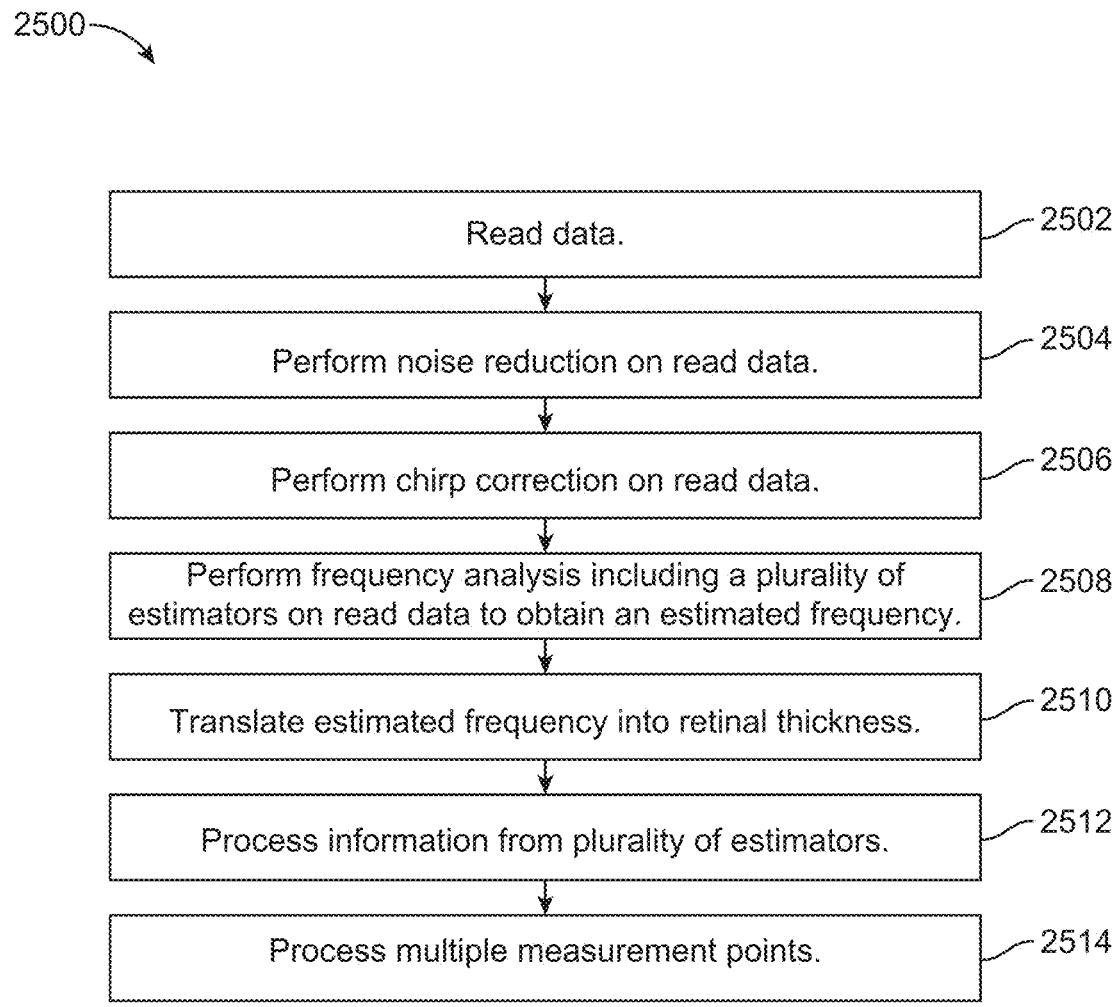
FIG. 25 shows a method for extracting a measurement of a retinal thickness (RT) or retinal layer thickness (RLT) from an OCT measurement, in accordance with some embodiments.

FIG. 25 shows a method 2500 for extracting a measurement of a retinal thickness (RT) or retinal layer thickness (RLT) from an OCT measurement, in accordance with some embodiments. The method 2500 comprises reading data, performing noise reduction on the read data, performing chirp correction on the read data, performing frequency analysis on the read data to obtain an estimated frequency, translating the estimated frequency into a retinal thickness, processing information from a plurality of estimators, and processing multiple measurement points.

In step 2502, OCT data obtained by the OCT measurement system is read to form read data. In some cases, the read data comprises OCT interference intensities.

In step 2504, noise reduction is performed on the read data.

In step 2506, chirp correction is performed on the read data. The chirp correction may comprise re-sampling the OCT signal in the time domain. Re-sampling the OCT signal may transform a linear time signal into a linear wave-vector signal. The re-sampling may compensate for phase instabilities arising due to non-linearities in the relationship between the wavelength of light emitted by a VCSEL or other light source and the drive current of the VCSEL or other light source, variations in temperature, aging of optical components, vibrations, or other environmental conditions. The re-sampling may be based on a phase measurement of the light source, such as the phase measurement methods as described herein. The re-sampling may be carried out during post-processing of an SS-OCT signal described herein.

The re-sampling may comprise first and second correction operations. In the first correction operation, the re-sampling may correct for an average non-linearity in the phase of light emitted by the VCSEL or other light source based on an average behavior of the light emitted by the light source over a period of time. In the second correction operation, the re-sampling may correct for deviations from the average behavior of the light source. The second correction operation may be based on a simultaneous acquisition of the phase signal and the SS-OCT signal and may therefore correct for variations associated with changes in temperature, humidity, aging of optical or electronics components, and other sources of drift of the SS-OCT signal.

In step 2508, frequency analysis is performed on the read data to obtain an estimated frequency. The frequency analysis may be performed using one or more estimators. The frequency may be performed using one, two, three, four, five, or more than five estimators. The estimators may utilize eigenspace techniques. The estimators may utilize eigen decomposition techniques. The estimators may utilize Pisarenko decomposition techniques. The estimators may utilize multiple signal classification (MUSIC) techniques. Each estimator of the one or more estimators may utilize a MUSIC technique with a unique filter. Each estimator may obtain an estimated frequency from the read OCT data.

In step 2510, one or more estimated frequencies are used to determine an estimated RT or RLT. A RT or RLT may be obtained from an analysis of terms of the interference signal. The terms used to determine the RT or RLT may comprise auto terms or cross terms of the interference signal, and combinations thereof. Auto terms may be generated by back-reflected signals from a sample (e.g. a retina or retinal layer), independent of a reference arm of the SS-OCT system. An auto term may correspond to a single frequency at a relatively low frequency. The frequency associated with the auto term may directly relate to a RT or RLT. A RT or RLT may be obtained from an analysis of a cross term of the interference signal. Cross terms may be generated by back-reflected signals from a sample and a reference mirror. A cross term may correspond to a pair of frequencies at relatively high frequencies. The difference between the two frequencies of the pair of frequencies may directly relate to a RT or RLT. The terms can be combined to determine a thickness of the retina, thicknesses of a plurality of layers, and relative locations of each of a plurality of layers of the retina.

Alternatively or in combination, a RT or RLT may be obtained from an analysis of the envelope of the OCT signal in the time domain. The envelope of the OCT signal may be calculated by performing a mathematical transform on the OCT signal, such as a Hilbert transform. The envelope may be subjected to a filtering operation to obtain a filtered envelope. The RT or RLT may relate to a beat frequency of the filtered envelope. Estimations of a RT or RLT using the envelope of the OCT signal may be less susceptible to noise such as that associated with motion (of the SS-OCT device or a user of the SS-OCT device).

In step 2512, the information from the plurality of estimators is processed. The processing of the multiple estimators may utilize a statistical analysis procedure. The processing of the multiple estimators may utilize an artificial intelligence or machine learning procedure, for example.

In step 2514, multiple measurement points are processed. The multiple measurement points may be processed from multiple measurements taken at a single location on a retina. The multiple measurement points may be processed from measurements taken at a plurality of location on the retina.

Although FIG. 25 shows a method 2500 for extracting a measurement of a retinal thickness (RT) or retinal layer thickness (RLT) from an OCT measurement in accordance with some embodiments, a person of ordinary skill in the art will recognize many variations and adaptations. For example, some of the steps may be deleted, some of the steps may be repeated, and some of the steps may comprise sub-steps. The steps may be performed in a different order, for example.

Figure 26:
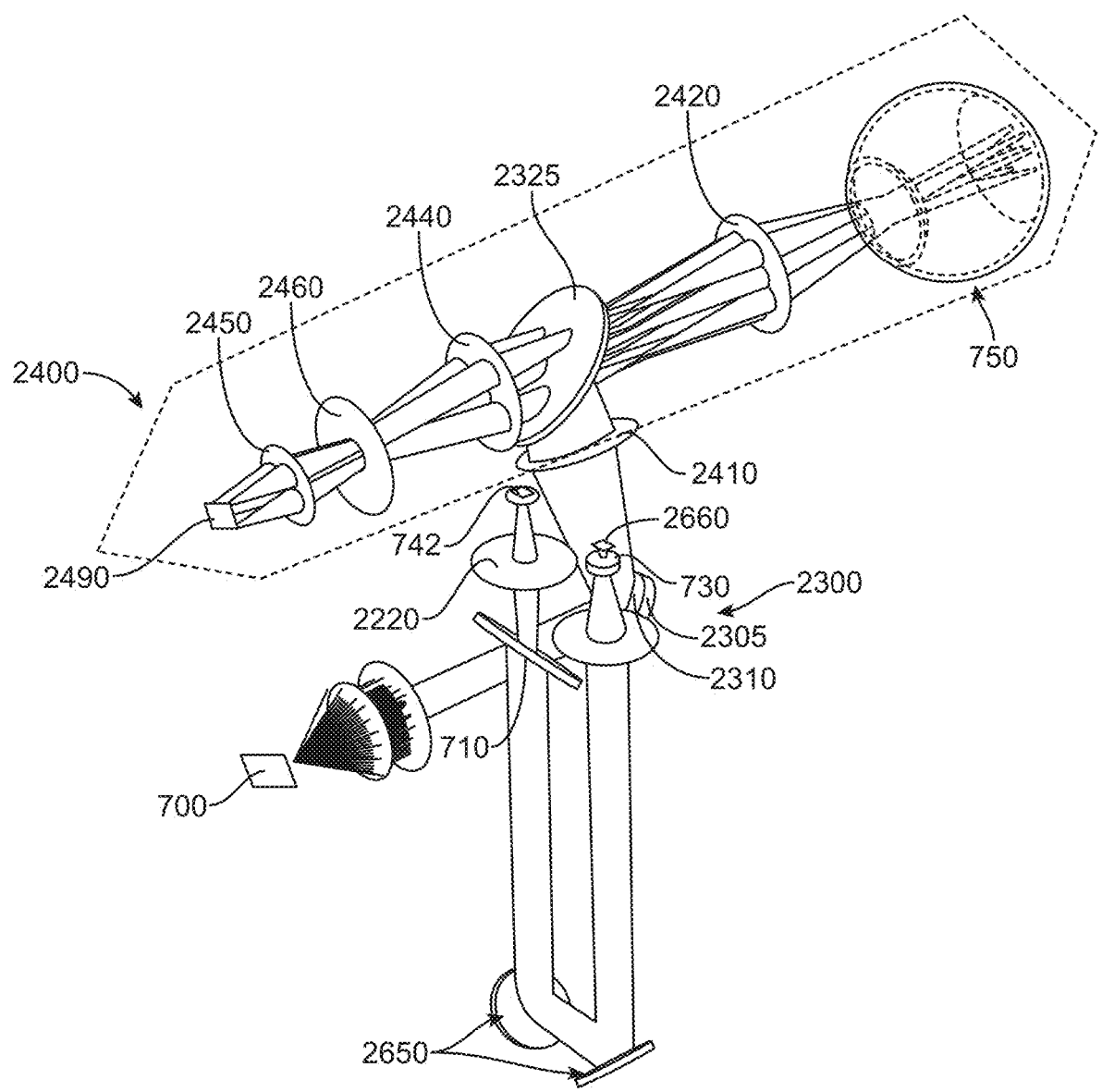
FIG. 26 shows a schematic for a SS-OCT device incorporating a visual function measurement apparatus, in accordance with some embodiments.

FIG. 26 shows a schematic for a SS-OCT incorporating a visual function measurement apparatus, in accordance with some embodiments. The system may be sized for the patient to lift the system and may comprise a weight sufficient to allow the patient to lift the system for measurements, for example. The system may comprise patient visualization system 2400, and the optical components may be arranged to provide a compact system that may be held by the patient during measurements, for example. The system may comprise display 2490, and may comprise the fundus camera as described herein. The light from the light source 700 may be directed toward a mirror 710 that splits the light into a measurement leg directed toward eye 750 and a reference leg directed toward reference mirror 730. Reference mirror 730 may be coupled to an optical detector 2660 that may detect a portion of light transmitted by the reference mirror. Optical detector 2660 may measure fluctuations in light output from the light source. Reference mirror 730 may be coupled to an actuator (not shown) to adjust the distance of the reference mirror in order to adjust the distance of the reference mirror to compensate for varying distances from patient contacting structure to the retina of the subject. The reference leg may comprise a mirror to deflect the beam. The reference mirror may comprise a plurality of mirrors such as mirror pair 2650. Locations of mirror pair 2650 may be adjusted so as adjust the optical path length of the reference leg. For example, actuators may be coupled to the mirror pair 2650 to adjust the mirrors in a trombone configuration, so as to adjust the optical path length of the reference leg.

The scanning mechanism 2300 may scan the measurement beam and receive light from retina and direct light to the retina in a confocal configuration as described herein.

Figure 34:
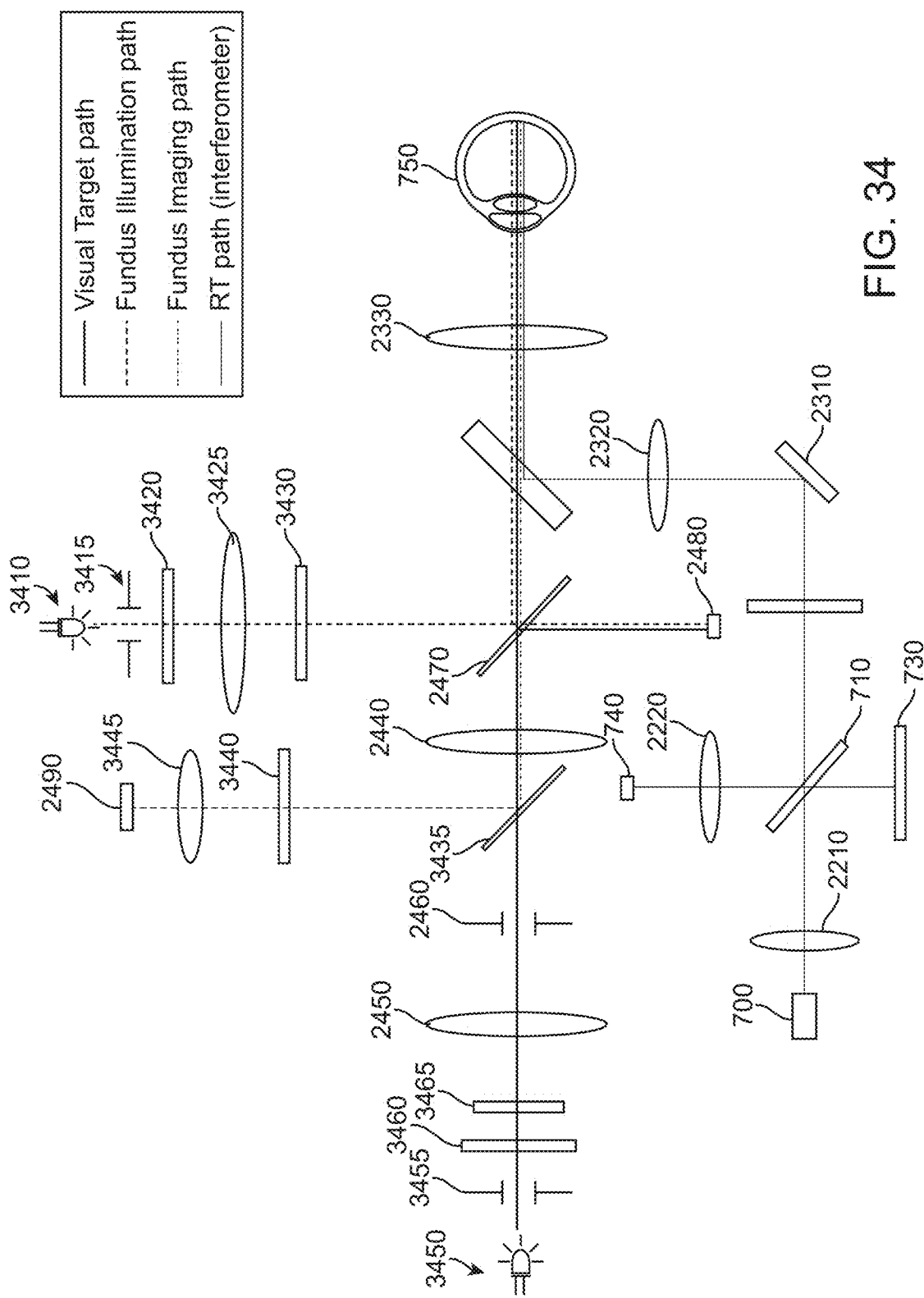
FIG. 34 shows a schematic for the optics of a SS-OCT device incorporating a visual fixation target apparatus and a fundus imaging apparatus, in accordance with some embodiments.

FIG. 34 shows a schematic 3400 for the optics of a SS-OCT device incorporating a visual fixation target apparatus and a fundus imaging apparatus, in accordance with some embodiments.

The optics may comprise a RT or RLT path comprising an interferometer, as described herein. The interferometer may comprise a light source 700, as described herein. The light source may direct light to an optional collimating lens 2210 and a beamsplitter 710, as described herein. The beamsplitter may direct a first portion of the light incident on the beamsplitter along a reference arm to reference mirror 730 and a second portion of the light incident on the beamsplitter to a measurement arm of the interferometer, as described herein. The second portion of the light may be directed to an optional filter (such as a bandpass filter) 3470 and a scanning mirror 2310 or other scanning mechanism, as described herein. The scanning mirror may direct the second portion of the light to a telescope system comprising a first telescope lens 2320 and a second telescope lens 2330, as described herein. The telescope system may further comprise a mirror 2325 to deflect scanned light deflected by the scanning mirror toward the eye 750, as described herein. Scanned light may be reflected from the eye, the retina, or one or more layers of the retina, as described herein and directed back along the path comprising elements 2330, 2325, 2320, 2310, 3470, and 710. The scanned light may then be passed by the beamsplitter 710 to an optional focusing lens 2220 and a detector 740, as described herein. The detector may detect an interference between the scanned light that has passed through the measurement arm of the interferometer and the reference light that has passed along the reference arm of the interferometer, as described herein.

The optics may further comprise a visual target path. The visual target path may comprise a visual target light source 3450. The visual target light source may comprise a light emitting diode (LED). The LED may emit light having a wavelength that is within the visible portion of the electromagnetic spectrum. For instance, the LED may emit light having a wavelength that is within a range from 400 nm to 700 nm. The LED may emit approximately green light. For instance, the LED may emit light having a wavelength of about 525 nm. The LED may emit light at a plurality of wavelengths that are within the visible portion of the electromagnetic spectrum. The visual target light source may direct light toward an aperture 3455 comprising a stop. The stop may comprise a ring stop, for example. The light may then pass to a diffuser 3460. The light may then pass to a collimating lens 2450 and a stop 2460, as described herein. The light may be directed to a hot mirror 3435. The hot mirror may be configured to pass light from the visual target path to a lens 2440, as described herein. The light may then pass to a beamsplitter 2470, as described herein. The beamsplitter may pass visual target light to the eye 750. The light may be detected by the eye and provide a target for a user to focus upon. Focusing on the target may allow a user to reduce the motion of the user's eye during fundus, RT, or RLT measurements. In some cases, the beamsplitter may pass visual target light to the eye through the mirror 2325 and the second telescope lens 2330, as described herein. The beamsplitter 2470 may be configured to direct a portion of the visual target light to a detector 2480. The portion of the visual target light directed to the detector may allow the optical power delivered to the eye to be monitored over time.

The optics may further comprise a fundus illumination path. The fundus illumination path may comprise a fundus illumination light source. The fundus illumination light source may comprise an LED. The LED may emit light having a wavelength that is within the near infrared portion of the electromagnetic spectrum. For instance, the LED may emit light having a wavelength that is within a range from 700 nm to 2500 nm. For instance, the LED may emit light having a wavelength of about 780 nm. The LED may emit light at a plurality of wavelengths that are within the near infrared portion of the electromagnetic spectrum. The fundus illumination light source may direct light toward an aperture 3415 comprising a stop. The stop may comprise a ring stop, for example. The light may then pass to a diffuser

3420. The light may then pass to a collimating lens 3425. The light may then pass to a first polarizer 3430. The first polarizer may be a linear polarizer. The first polarizer may impart a linear polarization to the light. The first polarizer may be an s-polarizer. The first polarizer may impart an s-polarization to the light. The first polarizer may be a p-polarizer. The first polarizer may impart a p-polarization to the light. The light may then pass to a beamsplitter 2470, as described herein. The beampslitter may pass fundus illumination light to the eye 750. In some cases, the beamsplitter may pass fundus illumination light to the eye through the mirror 2325 and the second telescope lens 2330, as described herein. The beamsplitter 2470 may be configured to direct a portion of the fundus illumination light to a detector 2480. The portion of the fundus illumination light directed to the detector may allow the optical power delivered to the eye to be monitored over time.

The optics may further comprise a fundus imaging target path. The fundus imaging target path may receive fundus illumination light reflected from the eye. The light may be directed through the elements 2330, 2325, 2470, 2440, and 3435. The hot mirror 3435 may be configured to direct the light to a second polarizer 3440. The second polarizer may be configured to pass light having a polarization similar to the polarization imparted by the first polarizer. The light may be directed to an imaging lens 3445 and a camera 2490, as described herein.

The imaging lens and camera may record one or more images of the fundus of a user's eye. The imaging lens and camera may be configured to record a series of images of the fundus of a user's eye. The camera may be coupled to an image processor. The image processor may be configured to recognize the fundus. For instance, the image processor may be configured to detect a vein of the fundus. The image processor may be configured to detect the vein of the fundus by comparing an image of the fundus to a template. The template may comprise a small region of an image of the eye containing the vein. The image processor may be configured to detect tubular structures of the diameter of the vein. For instance, the image processor may be configured to implement a filter, such as a Hessian multiscale filter, to detect the vein. The filter may enhance the clarity of a region of the fundus image containing the vein and the clarity of the region of the template containing the vein. The image processor may cross-correlate the enhanced region of the fundus image with the enhanced region of the template. In this manner, the location of the vein may be determined. The location of the vein may be determined for each fundus image in a series of fundus images. In this manner, the relative motion of the eye may be measured over time.

Figure 35:
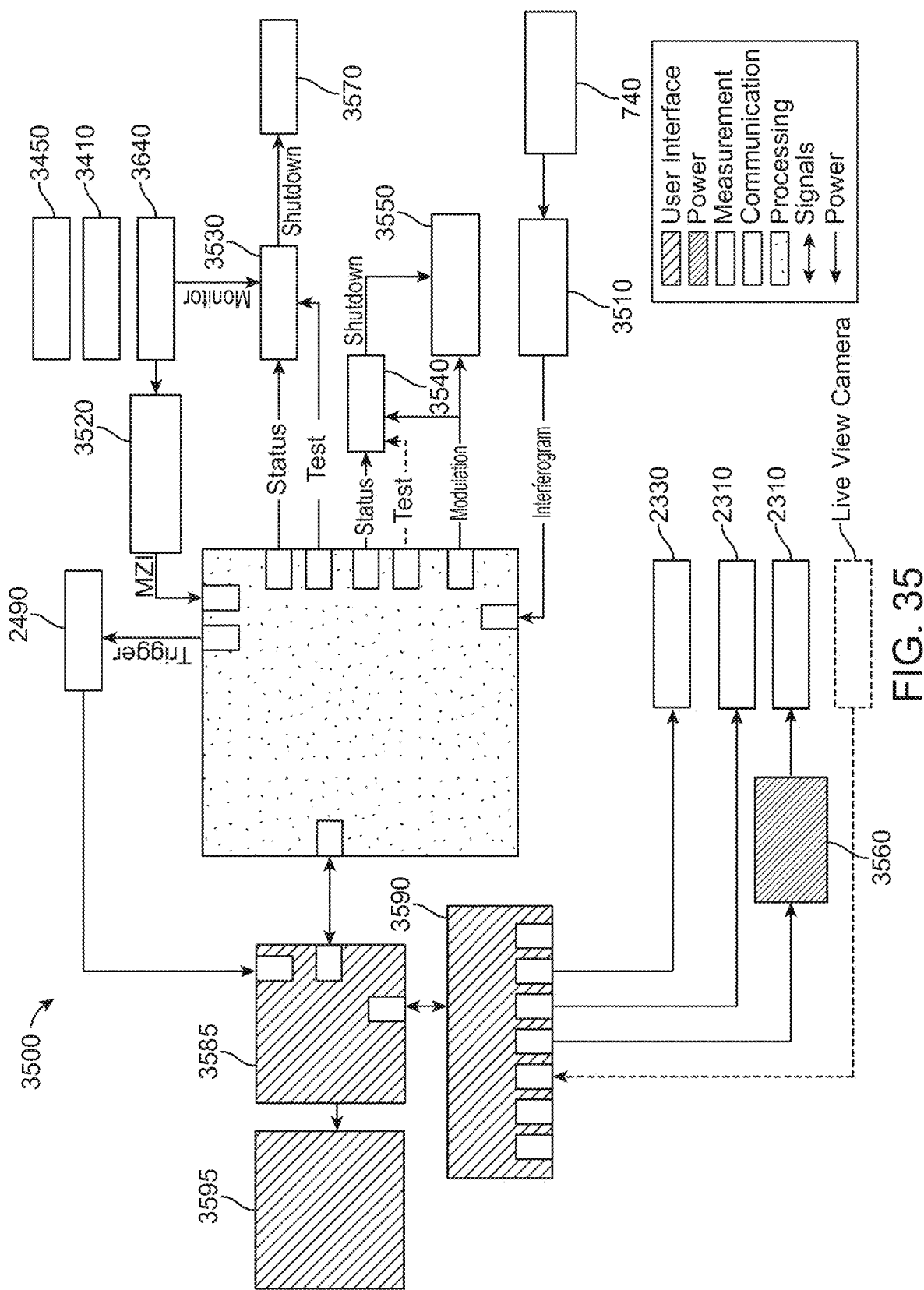
FIG. 35 shows a schematic of an electronic circuit board for controlling the optics of the compact SS-OCT systems described herein, in accordance with some embodiments.

FIG. 35 shows a schematic 3500 of electronic circuitry for controlling the optics of the compact SS-OCT systems described herein. The optics described herein may be coupled to electronic circuitry configured to control the operations of various elements of the optics. For instance, a photodetector 740 described herein may be electronically coupled to a first filter 3510, such as a low pass filter. The first filter may be configured to receive an interference signal described herein from the photodetector, filter the interference signal, and pass the filtered interference signal to a data acquisition module 3580. The data acquisition module may comprise a data acquisition card, such as a data acquisition card provided by National Instruments. The data acquisition module may comprise one or more analog to digital converters (ADCs) or one or more digital to analog converters (DACs). The data acquisition module may be configured to sample the ADCs at a sampling rate of at least 1 kilosample per second (kS/s), at least 2 kS/s, at least 5 kS/s, at least 10 kS/s, at least 20 kS/s, at least 50 kS/s, at least 100 kS/s, at least 200 kS/s, at least 500 kS/s, at least 1,000 kS/s, at least 2,000 kS/s, at least 5,000 kS/S, or at least 10,000 kS/s. The data acquisition module may be configured to sample the ADCs at a sampling rate that is within a range defined by any two of the preceding values. The data acquisition module may be configured to sample the DACs at a sampling rate of at least 1 kilosample per second (kS/s), at least 2 kS/s, at least 5 kS/s, at least 10 kS/s, at least 20 kS/s, at least 50 kS/s, at least 100 kS/s, at least 200 kS/s, at least 500 kS/s, at least 1,000 kS/s, at least 2,000 kS/s, at least 5,000 kS/S, or at least 10,000 kS/s. The data acquisition module may be configured to sample the DACs at a sampling rate that is within a range defined by any two of the preceding values.

An interferometer apparatus 3640 for enhancing phase stability described herein (for instance, with respect to FIG. 36) may be electronically coupled to a second filter 3520, such as a low pass filter. The second filter may be configured to receive a phase measurement from the interferometer apparatus 3640 as described herein, filter the phase measurement, and pass the filtered phase measurement to the data acquisition module.

The electronic circuitry may comprise safety circuitry. The electronic circuitry may comprise a first safety circuit 3530 electronically coupled to the data acquisition module. The first safety circuit may be configured to receive a first status signal from the data acquisition module. The first safety circuit may be configured to monitor a signal from the interferometer apparatus 3640. If a signal from the interferometer apparatus 3640 exceeds a safe level, the first safety circuit may send a signal to activate a first safety device 3570, such as a shutter. Activation of the first safety device may reduce the amount of optical power received by the interferometer apparatus 3640 or an eye of a subject to a safe level. In the event that the first safety device is activated, the first safety circuit may send a status signal to the data acquisition module. This status signal may be passed to an operator of the SS-OCT device to ensure that the operator is informed about the safety status.

The electronic circuitry may comprise a second safety circuit 3540 electronically coupled to the data acquisition module. The second safety circuit may be configured to a receive a second status signal from the data acquisition module. The second safety circuit may be configured to monitor a signal from a light source driver 3550, such as a VCSEL driver. If an output power from the light source driver exceeds a safe level, the second safety circuit may send a signal to shut down the light source driver or otherwise reduce the power supplied by the light source driver. Shutting down or reducing power from the light source driver may reduce the amount of optical power supplied by the light source to a safe level. The data acquisition module 3580 may be configured to send a modulation signal to the light source driver to modulate the operating current of the light source as described herein.

The data acquisition module 3580 may be electronically coupled to a fundus camera 2490 described herein. The data acquisition module may be configured to trigger a measurement from the fundus camera. A signal from the fundus camera may be directed to a computation module 3585. The computation module may comprise an external computer. The computation module may comprise a personal computer or workstation. The computation module may comprise a mobile device, such as a tablet or smartphone. The computation module may be configured to operate a visualization program, such as a graphical user device (GUI). The computation module may be configured to receive one or more fundus images from the fundus camera. The computation module may be configured to display the one or more fundus images on a display 3595. The display may be external to the computation module, such as an external monitor electronically coupled to the computation module. The display may be integrated into the computation module, as may be the case for a computation module configured as a mobile device.

The computation module may be electronically coupled to a control bus module 3590. The control bus module may comprise a universal serial bus (USB) hub. The computation module may direct signals to the control bus module 3590 to control the operation of one or more optical components of the compact SS-OCT system. For instance, the control bus module may direct a signal to a scanner interface module 3560 that controls the operation of the scanning element 2310 described herein. The scanner interface module may comprise a high voltage driver that powers the scanning element at a high voltage, such as a voltage of up to 200 V. The control bus module may direct a signal to a first OCT focusing element, such as any of lenses 2320, 3650, or 3655 described herein, to adjust a focus of the SS-OCT systems described herein. The control bus module may direct a signal to a second OCT focusing element, such as any of lenses 2330, 3650, or 3655 described herein, to adjust a focus of the SS-OCT systems described herein. The first or second focusing elements may comprise tuneable lenses. Alternatively or in combination, the first or second focusing elements may comprise moveable lenses. The control bus module may direct a signal to a live view camera. The live view camera may provide one or more images of an eye. The live view camera may provide one or more images of a side view of an eye. Images acquired by the live view camera may assist an operator of an SS-OCT device described herein in correctly aligning the device with a subject's eye. For instance, images acquired by the live view camera may allow the operator to select a proper distance between the eye and the SS-OCT device.

Though not shown in FIG. 35, the electronic circuitry may be configured to control other elements of the compact SS-OCT systems described herein. For instance, the electronic circuitry may be configured to control any or all optical elements described herein with respect to any of FIG. 5, 6A, 7A, 8A, 8B, 22, 23A, 24, 26, 34, or 36. The computation module 3585 may be configured to implement any steps of any method described herein, such as methods 1100, 1200, or 2500.

Figure 36:
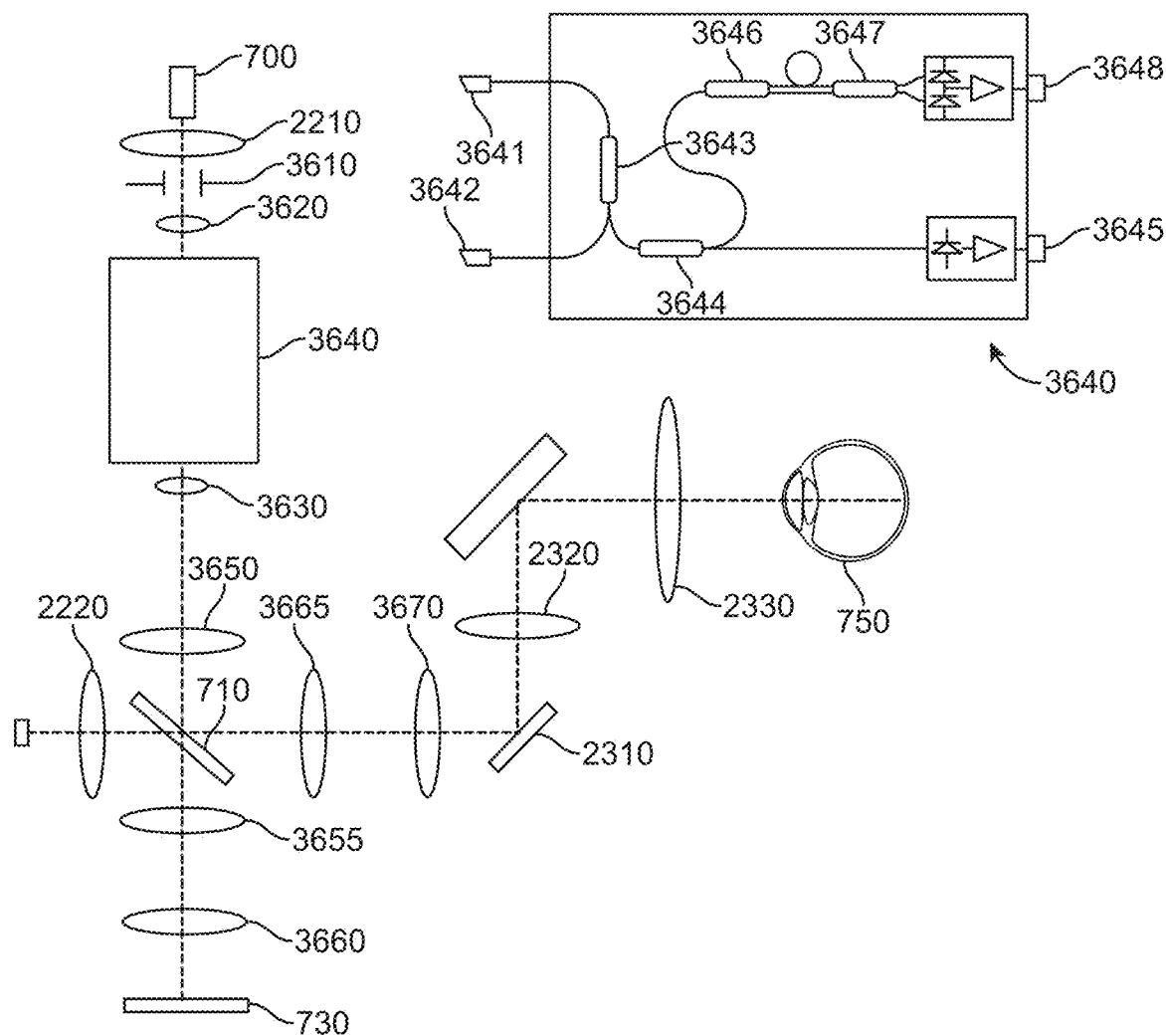
FIG. 36 shows a schematic for the optics of a SS-OCT device incorporating an interferometer for enhancing phase stability.

FIG. 36 shows a schematic 3600 for the optics of a SS-OCT device incorporating an interferometer for enhancing phase stability. The optics may comprise a light source 700, collimating lens 2210, beam splitter 710, reference mirror 730, scanning mirror 2310, telescope lenses 2320 and 2330, mirror 2325, focusing lens 2220, and detector 740, as described herein. The elements 700, 2210, 710, 730, 2310, 2320, 2330, 2325, 2220, and detector 740 may be arranged to produce an OCT signal from an eye 750, as described herein.

The optics may further comprise an aperture 2460 comprising a stop. The stop may comprise a ring stop, for example. The stop may be located between the collimating lens 2210 and a first coupling lens 3620. The first coupling lens may be a fiber coupling lens. The first coupling lens may have a numerical aperture sufficient to direct collimated light emitted by the light source into an optical fiber. The first coupling lens may be configured to direct light to an interferometer apparatus 3640.

The interferometer apparatus may be a fiber-based interferometer apparatus. Alternatively, the interferometer apparatus may be a bulk interferometer apparatus. The interferometer apparatus may be configured to direct a first portion (such as 95% of the light) of the light to a second coupling lens 3630 and a second portion (such as 5% of the light) of the light to a light analysis unit within the interferometer apparatus. The light analysis unit may direct a third portion (such as 50% of the second portion of the light) of the light to a power monitoring apparatus within the interferometer apparatus and a fourth portion (such as 50% of the second portion of the light) of the light to a Mach-Zender interferometer. The power monitoring apparatus may measure an optical power of the light incident on the interferometer apparatus and output the measurement to a power measurement output 3642. Such a measurement may allow monitoring to ensure that the optical power does not exceed a safe level. The Mach-Zender interferometer may measure a phase of the light coupled into the interferometer apparatus and output the measurement to a phase measurement output 3644. The phase may be monitored and phase drifts (such as phase drifts associated with ambient temperature fluctuations, aging of optical components, transient responses of optical or electronic components, or other factors) may be corrected. Correction of the phase drifts may narrow peaks in the frequency domain. This may increase the accuracy of the RT or RLT estimations.

A phase measurement may be obtained by a Mach-Zender interferometer, as described herein. Alternatively or in combination, the phase measurement may be obtained using another optical phase measurement apparatus, such as a Fabry-Perot cavity. The phase of the light source may be acquired simultaneously with an OCT signal.

The second coupling lens may be a fiber coupling lens. The second coupling lens may have a numerical aperture sufficient to accept light emitted by the interferometer apparatus and direct the light to first and second tunable lenses 3650 and 3655 and a focusing lens 3660. The first and second tunable lenses may be configured to vary a spot size of light emitted by the SS-OCT system on a retina.

The optics may further comprise a beam expander comprising first and second beam expander lenses 3665 and 3670.

Figure 27A:
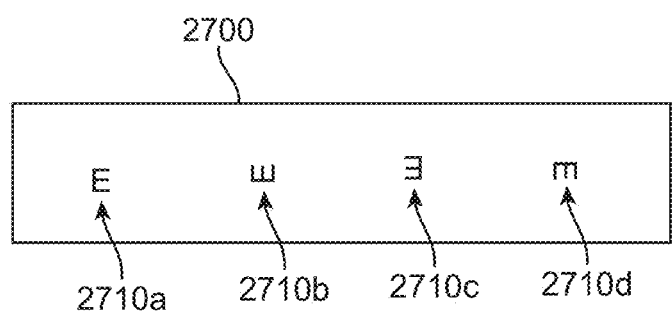
FIG. 27A and FIG. 27B show visual cues on a background, in accordance with some embodiments.

FIG. 27A shows dark visual cues on a light background. The visual cues may be presented alone, or in combination. The visual cue may comprise a letter at an orientation, such as a tumbling E, for example. The subject may input the orientation of the orientation of the letter in order to determine the visual acuity of the subject. The visual cues may comprise a plurality of dark letters 2710a, 2710b, 2710c, and 2710d, such as the letter "E", on a light background 2700. Although four letters are shown, the visual cues may comprise 1, 2, 3, 4, 5, 6, 7, 8, 9, 10, or more than 10 letters. The letters may move along the background, such as downward along the background. Other visual stimuli may be presented, such as an arrow, in which the patient indicates the orientation of the letter.

Figure 27B:
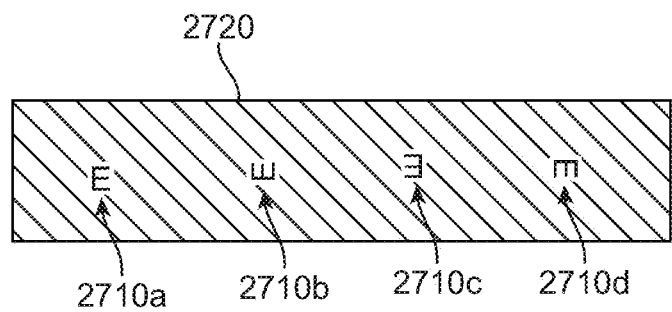

FIG. 27B shows dark visual cues on a dark background. The visual cues may comprise a plurality of dark letters 2710a, 2710b, 2710c, and 2710d, such as the letter "E", on a dark background 2720. Although four letters are shown, the visual cues may comprise 1, 2, 3, 4, 5, 6, 7, 8, 9, 10, or more than 10 letters. The letters may move along the background, such as downward along the background. The letters may be presented in different orientations, such as facing to the left, right, up, or down.

In many embodiments, the visual cues are shown on the display as described herein, and the lens may compensate for the refractive error of the subject in order to test vision of the subject. The compact SS-OCT system may comprise an input for the patient to input an orientation of the letter presented, such that the vision of the patient may be determined. The input may comprise an input configured to receive an orientation of the letter, such as a button or a plurality of buttons, for example.

FIG. 28A shows a schematic of a housing for an exemplary handheld monocular OCT system, in accordance with some embodiments. The left side of the figure shows a side view 2800 of the housing. The housing may comprise and a body 2810. The body of the housing may comprise a handle 2850 for the patient to grasp the system. The body 2810 may be coupled to a structure to contact the patient, such as an eye piece 2805, or foam or other structure. The housing may have an inner volume that contains any of the components of the handheld OCT systems and devices described herein. The reference leg of the interferometer may extend at least partially into the handle 2850, for example.

The eye piece may be configured to dock the housing to an area surrounding a subject's eye, such as the skin surrounding the subject's eye. The body may be configured to be held within a hand of the subject.

The right side of the figure shows a front view 2820 of the housing. The eye piece may comprise an area 2825 configured to dock with an area surrounding a subject's eye and an opening 2830 configured to allow OCT measurement light to travel from the OCT system to the eye and back. The opening may be further configured to present visual cues to the subject (such as one or more of the letter "E"), as described herein. The housing may comprise a mechanism 2835 that allows a subject to indicate the orientation (such as facing left, right, up, or down) of each letter presented to them.

FIG. 28B shows a housing for an exemplary handheld monocular OCT system, in accordance with some embodiments.

FIGS. 29A and 29B show a configuration for a handheld binocular OCT system, in accordance with some embodiments. Alternatively, the system may comprise a monoocular system, in which the non-measured eye is occluded with the measurement system. The left side of the figure shows a side view 2900 of the housing. The housing may comprise eye pieces 2905a and 2905b and a body 2910. The housing may have an inner volume that contains any of the components of the handheld OCT systems and devices described herein. The eye pieces may be configured to dock the housing to an area surrounding a subject's eyes, such as the skin surrounding the subject's eyes. The body may be configured to be held within both hands of the subject.

The right side of the figure shows a front view 2920 of the housing. The eye pieces may comprise areas 2925a and 2925b configured to dock with an area surrounding a subject's eyes and an opening 2930 configured to allow OCT measurement light to travel from the OCT system to one or both of the eyes and back. The opening may be further configured to present visual cues to the subject (such as one or more of the letter "E"), as described herein. The housing may comprise a mechanism 2935 that allows a subject to indicate the orientation (such as facing left, right, up, or down) of each letter presented to them.

FIG. 29C shows a housing for an exemplary handheld binocular OCT system, in accordance with some embodiments.

Figure 30:
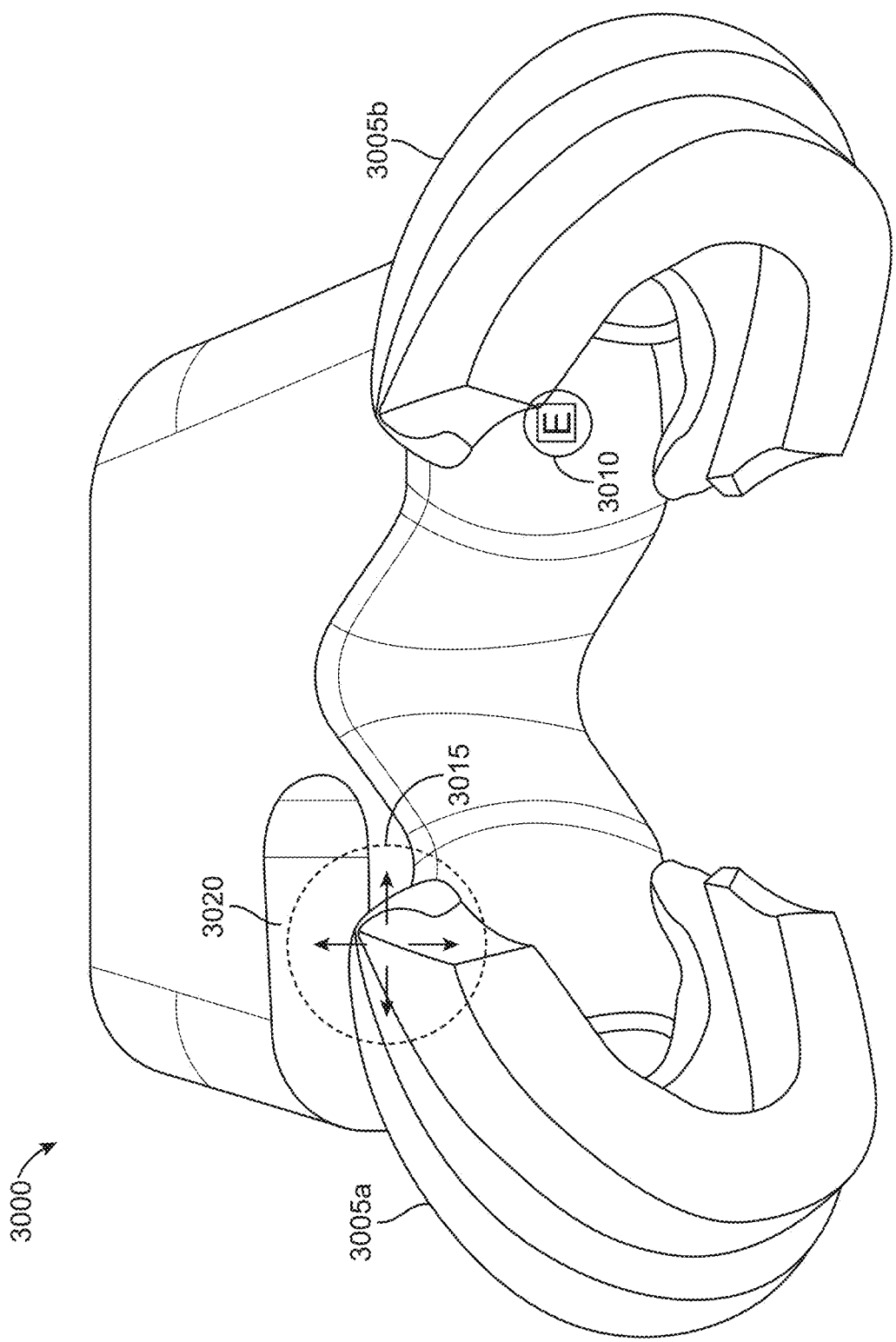
FIG. 30 shows a configuration for an exemplary handheld binocular OCT system, in accordance with some embodiments.

FIG. 30 shows a configuration for an exemplary handheld binocular OCT system, in accordance with some embodiments. The housing 3000 may comprise eye pieces 3005a and 3005b and a body 3020. The housing may have an inner volume that contains any of the components of the handheld OCT systems and devices described herein. The eye pieces may be configured to dock the housing to an area surrounding a subject's eyes, such as the skin surrounding the subject's eyes. The body may be configured to be held within both hands of the subject. One of the eye pieces may comprise an opening 3010 configured to allow OCT measurement light to travel from the OCT system to one of the eyes and back. The opening may be further configured to present visual cues to the subject (such as one or more of the letter "E"), as described herein. The housing may comprise a mechanism 3015 that allows a subject to indicate the orientation (such as facing left, right, up, or down) of each letter presented to them. The body of the housing may comprise a cutout area. The orientation of the cutout area may indicate which eye is to be measured using the OCT system. The cutout area may be located on the opposite side of the housing from the eye to be measured.

An orientation sensor such as an accelerometer may be mechanically coupled to the optics and electronically coupled to the control unit as described herein, in order to measure which eye is measured in response to an orientation of the orientation sensor.

Figure 31A:
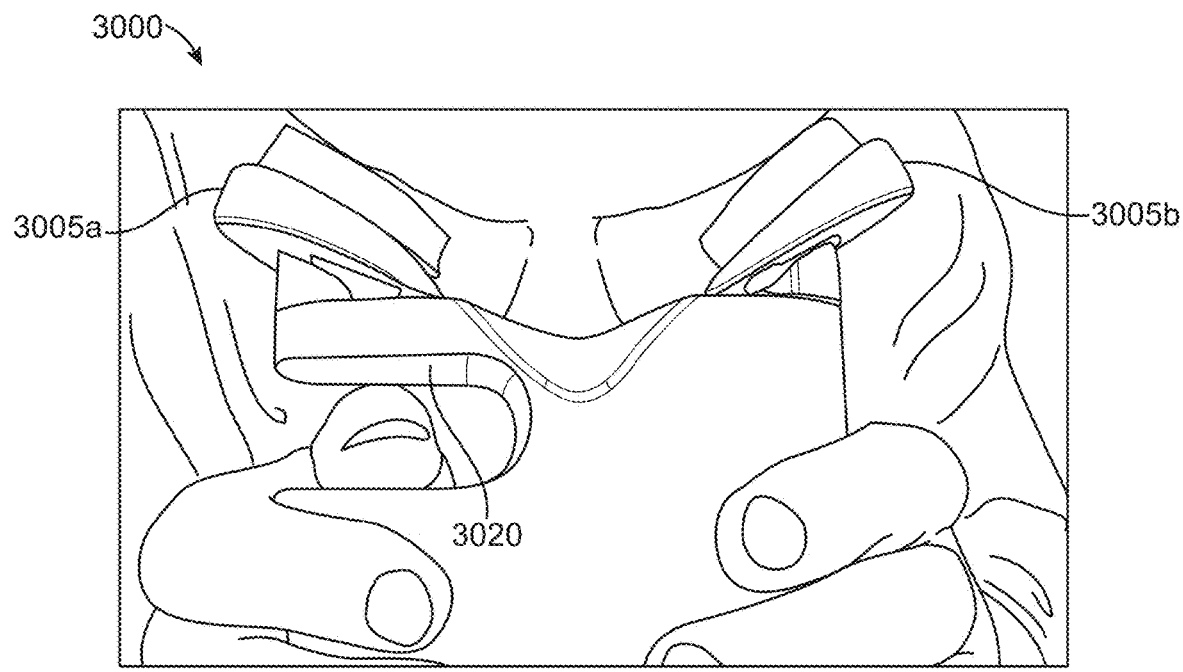
FIG. 31A shows a handheld binocular OCT system oriented to measure a subject's left eye, in accordance with some embodiments.

FIG. 31A shows a handheld binocular OCT system oriented to measure a subject's left eye.

Figure 31B:
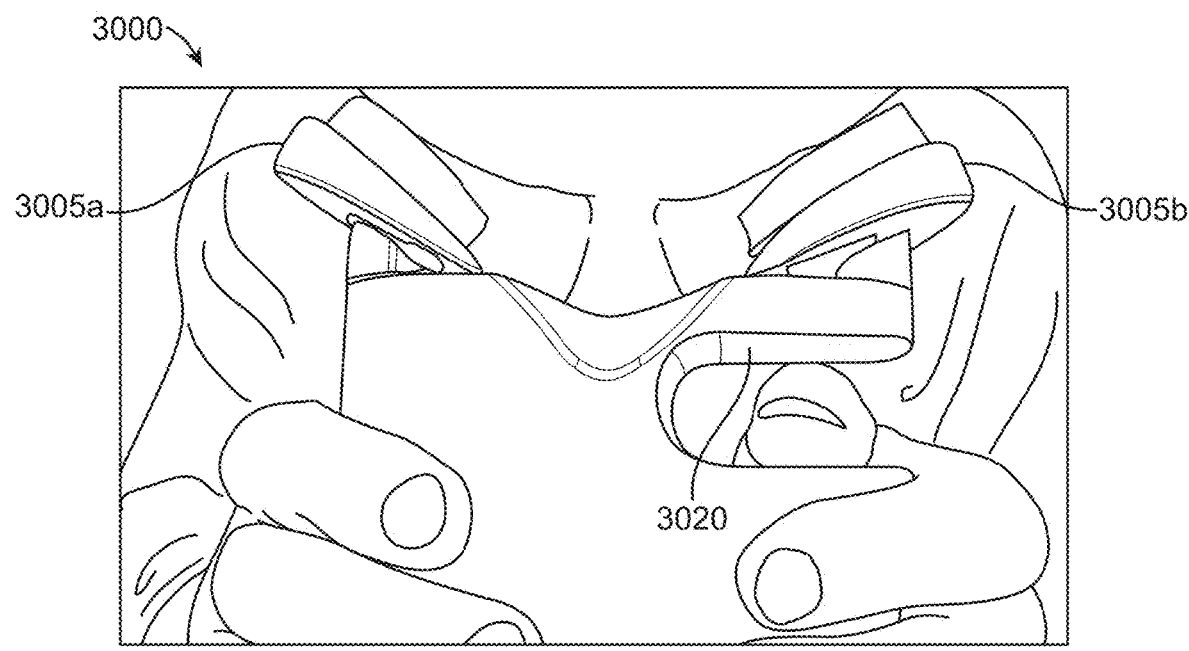
FIG. 31B shows a housing for an exemplary handheld binocular OCT system oriented to measure a subject's right eye, in accordance with some embodiments.

FIG. 31B shows a housing for an exemplary handheld binocular OCT system oriented to measure a subject's right eye.

Figure 32A:
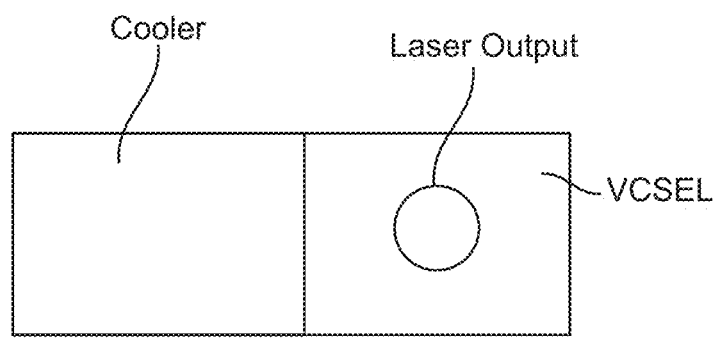
FIG. 32A shows a VCSEL coupled to a cooler to increase the range of wavelengths swept, in accordance with some embodiments.

FIG. 32A shows a VCSEL coupled to a cooler to increase a range of wavelengths swept with the VCSEL, in accordance with some embodiments. The VCSEL of the SS-OCT systems described herein may be subjected to a cooling procedure to reduce the operating temperature of the VCSEL to a temperature that is below the ambient temperature of approximately 37° C., in order to increase the range of wavelengths swept by the VCSEL. The cooling can be combined with overdriving of the VCSEL as described herein, in order to further increase the range of wavelengths swept by the VCSEL. The VCSEL of the SS-OCT systems may be cooled below ambient temperature by 10° C., 20° C., 30° C., 40° C., 50° C., 70° C., 80° C., 90° C. or more. The VCSEL of the SS-OCT systems may be cooled by an amount within a range defined by any two of the preceding values, for example cooled by an amount within a range from 20° C. to 70° C. The range of wavelengths swept can be increased by 1 nm, 2 nm, 3 nm, 4 nm, 5 nm, or increased by an amount within a range defined by any two of the preceding values. For example, a VCSEL with a specified wavelength sweep range of 5 nm can be overdriven to increase the sweep range by about 3 nm and chilled to increase the sweep range by about 2 nm to provide a total sweep range of about 10 nm. The cooler can be configured in many ways, and may comprise a Peltier cooler, a gas based cooler, a chamber comprising a gas such as nitrogen that expands to chill the VCSEL, or a chilled circulating fluid, and combinations thereof. The cooler may comprise a heat sink coupled to the VSCEL, for example.

Figure 32B:
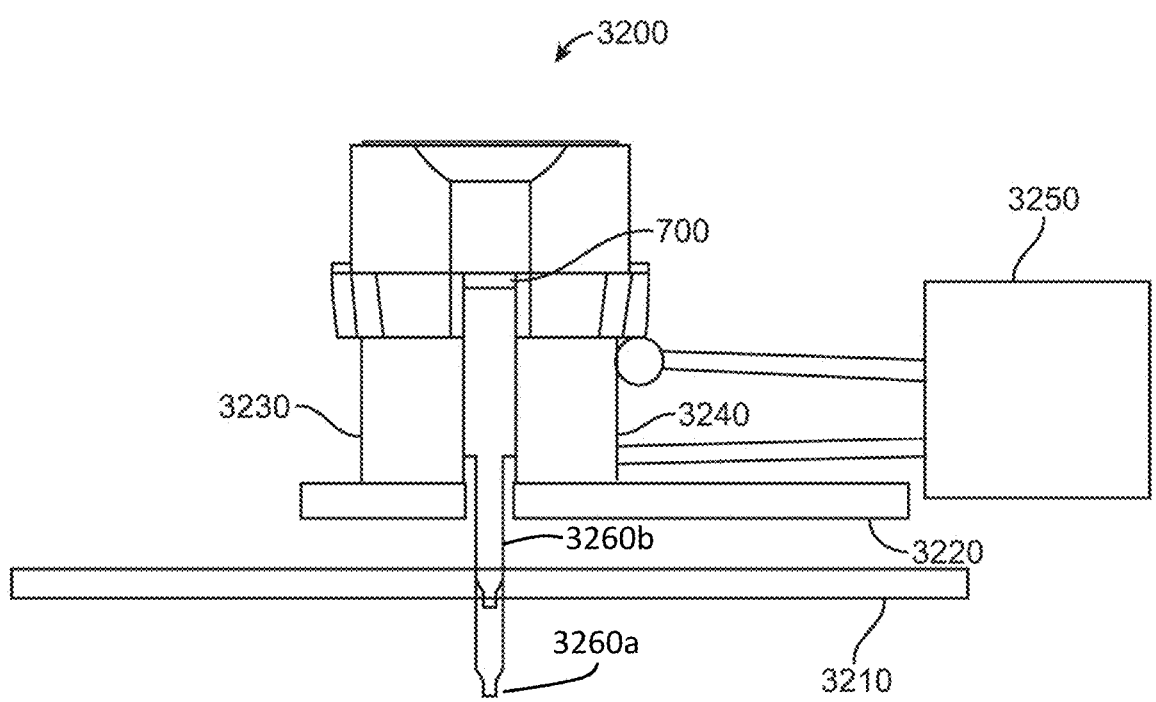
FIG. 32B shows a schematic of a VCSEL coupled to a thermoelectric cooler, in accordance with some embodiments.

FIG. 32B shows a schematic 3200 of a VCSEL coupled to a thermoelectric cooler. The VCSEL 700 may be mounted to a VCSEL driver 3210. The VCSEL driver may comprise a printed circuit board (PCB). The VCSEL may be mounted to the VCSEL driver through one or more electrical connectors, such as electrical connectors 3260a and 3260b. The VCSEL or VCSEL driver may be coupled to a heat sink 3220 configured to draw heat from the VCSEL or VCSEL driver. The VCSEL may be further coupled to a thermoelectric cooler (TEC) 3230. The TEC may comprise a Peltier cooler. The TEC may be configured to cool the VCSEL by 10° C., 20° C., 30° C., 40° C., 50° C., 70° C., 80° C., 90° C. or more. The TEC may be configured to cool the VCSEL by an amount within a range defined by any two of the preceding values. The VCSEL may be further coupled to a temperature sensor 3240. The temperature sensor may comprise a thermistor. The temperature sensor may be configured to measure an operating temperature of the VCSEL. The temperature sensor and TEC may be coupled to a TEC controller 3250. The TEC controller may control a cooling power of the TEC based on a measured temperature of the VCSEL by the temperature sensor. In this manner, the TEC, thermistor, and TEC controller may form a negative feedback system designed to maintain the VCSEL at a stable operating temperature, such as an operating temperature described herein.

Figure 33A:
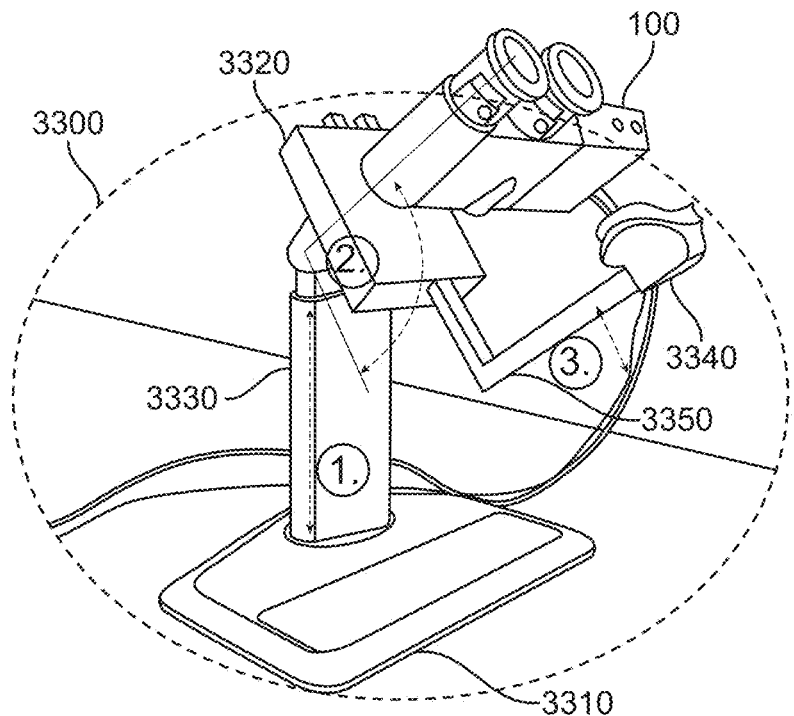
FIG. 33A shows a compact SS-OCT system placed on a support, in accordance with some embodiments

FIG. 33A shows a compact SS-OCT system as described herein placed on a support, such as a desktop mounted support. The compact SS-OCT system 100 may be any compact SS-OCT system described herein. The compact SS-OCT system may comprise any capabilities described herein. For instance, the compact SS-OCT system may comprise an OCT imaging system, an eye-tracking system, a visual fixation target, or a Badal lens, as described herein. The compact SS-OCT system may comprise one or two eyepieces.

The compact SS-OCT system may be placed a support system 3300, for example releasably mounted or attached to the support. The compact SS-OCT system may be fixably attached to the support system. The compact SS-OCT system may be removably attached to the support system. The support system may be mounted to a desktop or other surface. The support system 3300 may comprise a base 3310. The base may be attached to or placed on a desktop or other surface. The base may be fixably attached to the desktop or other surface. The base may be removably attached to the desktop or other surface.

The support system may further comprise a mounting surface 3320 to receive the compact SS-OCT system. The mounting surface may be a mounting plate. The mounting surface may provide a location to which the compact SS-OCT may be mounted. The mounting surface may be coupled to the base by a first coupler 3330. The first coupler may be configured to allow a user to change a distance between the mounting surface and the base, as indicated by the arrow labeled "1" in FIG. 33A. The distance between the mounting surface and the base may be adjustable by 1 cm, 2 cm, 5 cm, 10 cm, 20 cm, or 50 cm. The distance between the mounting surface and the base may be adjustable by a value that is within a range defined by any two of the preceding values. The distance between the mounting surface and the base may be adjusted to increase a user's comfort while using the compact SS-OCT system.

The support system may comprise a second coupler configured to allow a user to change an angle between the mounting surface and the base, as indicated by the arrow labeled "2" in FIG. 33A. The angle between the mounting surface and the base may be adjustable by 1 degree, 2 degrees, 5 degrees, 10 degrees, 20 degrees, 50 degrees, or 100 degrees. The angle between the mounting surface and the base may be adjustable by a value that is within a range defined by any two of the preceding values. The angle between the mounting surface and the base may be adjusted to increase a user's comfort while using the compact SS-OCT system.

The support system may further comprise a chinrest 3340. The chinrest may provide a location for a user to rest his or her chin while operating the compact SS-OCT system. The chinrest may be coupled to the mounting plate by an extension 3350. The support system may comprise a third coupler configured to allow a user to change a distance between the chinrest and the eyepieces, as indicated by the arrow labeled "3" in FIG. 33A. The distance between the chinrest and the eyepieces may be adjustable by a distance of 1 cm, 2 cm, 5 cm, or 10 cm. The distance between the chinrest and eyepieces may be adjustable by a value that is within a range defined by any two of the preceding values. The distance between the chinrest and the mounting surface may be adjusted to increase a user's comfort while using the compact SS-OCT system. The distance between the chinrest and the mounting surface may be adjusted to bring a user's eye into alignment with the eye pieces of the compact SS-OCT system. For instance, the distance between the chinrest and the eyepieces and the mounting surface may be adjusted to bring a user's eye into alignment with an optical axis of the compact SS-OCT system.

The compact SS-OCT system placed on the support may have a length, a width, and a height. The length may comprise a longest dimension across the system, the width may comprise a next longest dimension across the system, and the width may comprise a shortest dimension across the system. The length, width and height may extend transverse to each other, for example perpendicular to each other. The compact SS-OCT system may have a length of 10 cm, 20 cm, or 50 cm. The compact SS-OCT system may have a length that is within a range defined by any two of the preceding values. The compact SS-OCT system may have a width of 5 cm, 10 cm, or 25 cm. The compact SS-OCT system may have a width that is within a range defined by any two of the preceding values. The compact SS-OCT system may have a height of 2.5 cm, 5 cm, or 10 cm. The compact SS-OCT system may have a height that is within a range defined by any two of the preceding values.

The compact SS-OCT placed on the support may comprise a mass of 0.1 kg, 0.2 kg, 0.5 kg, 1 kg, or 2 kg. The support system may comprise a mass that is within a range defined by any two of the preceding values.

Figure 33B:
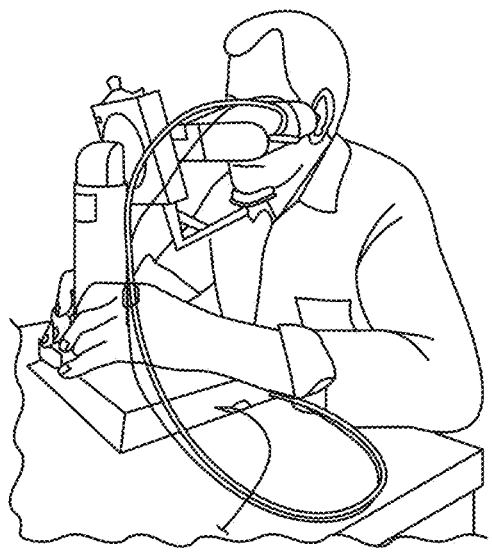
FIG. 33B shows a user using the compact SS-OCT device mounted on a support, in accordance with some embodiments.

FIG. 33B shows a user using the desktop-mounted SS-OCT device.

EXAMPLES

Example 1: Limit of Detection for RT or RLT Measurements

Figure 14:
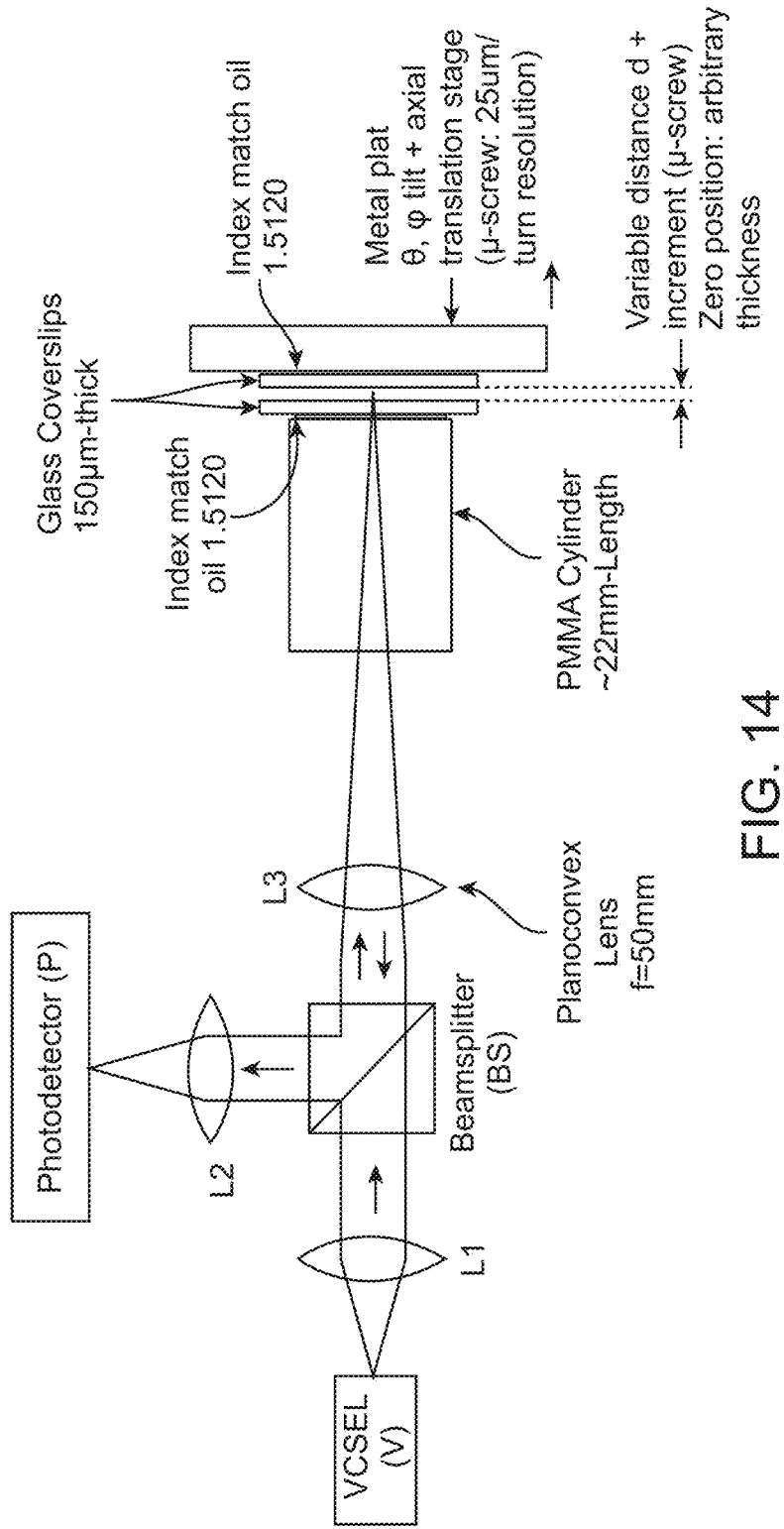
FIG. 14 shows an optical setup for determining the limit of detection of an SS-OCT system utilizing a single VCSEL and no reference arm.

FIG. 14 shows an optical setup for determining the limit of detection for measuring a change in RT or RLT using an SS-OCT system utilizing a single VCSEL and no reference arm. The setup comprises a VCSEL (V), a photodetector (P), a collimating lens (L1), a beamsplitter (BS), a lens (L2) for focusing light onto the photodetector, a lens (L3) for focusing light onto the sample, a 22 mm long cylinder made of polymethylmethacrylate (PMMA), index match oil with a refractive index of 1.5120, two 150 µm thick glass coverslips with an adjustable air gap between them, a second layer of index match oil with a refractive index of 1.5120, and a metal plate connected to a translation stage to produce changes in the distance between the first glass coverslip and the second glass coverslip. The distance between the two coverslips is varied by turning a microscrew with a resolution of 25 µm per turn. The SS-OCT signal is generated by interference between light reflected from the first glass-air interface and the second glass-air interface.

Example 2: Performance of a VCSEL Driven Out of its Rated Operating Range

Figure 15:
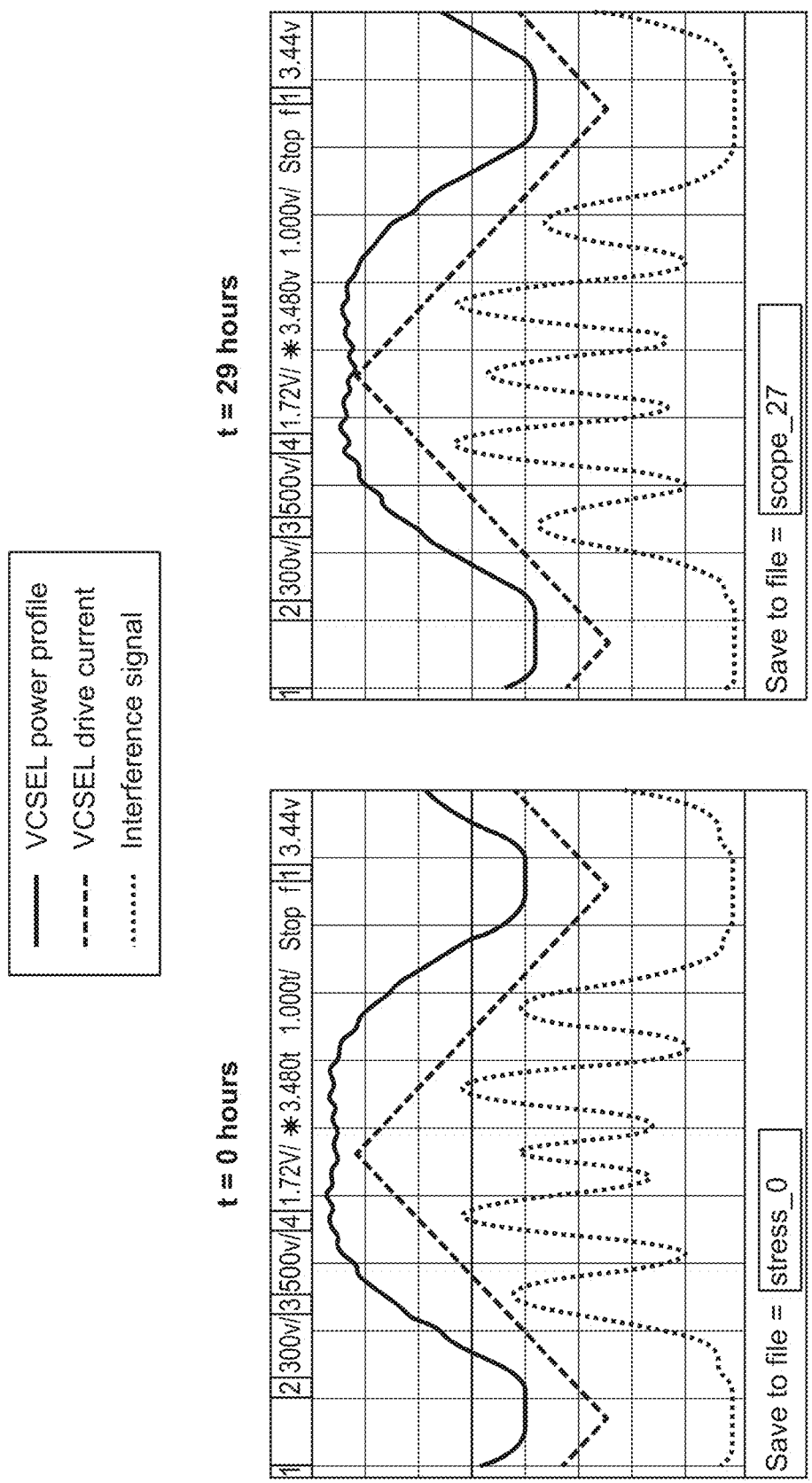
FIG. 15 shows oscilloscope signals at two different points in time for a VCSEL driven out of its rated operating range.

FIG. 15 shows oscilloscope signals at two different points in time for a VCSEL driven out of its rated operating range. The VCSEL had a central wavelength of approximately 850 nm and a rated range of emission wavelengths of approximately 1.8 nm. The VCSEL current was continuously swept in a triangular pattern with a maximum electric current of 15 mA. The current was swept at a frequency of 125 Hz. The experiment consisted of four intervals each of approximately 7.25 hours of continuous sweeping. Between each interval, the VCSEL was shut down for several hours. The VCSEL current (green), VCSEL power (red), and the interference signal (purple) were recorded at least every two hours. The measured values of all three parameters varied little between the first measurement at 0 hours of operation and a subsequent measurement after the VCSEL had been in operation for 29 hours. Thus, it can be concluded that a VCSEL driven out of its rated operating range may continue to produce useful SS-OCT measurements after at least 29 hours of use. This compares favorably with the usage requirements for a VCSEL implemented in a handheld SS-OCT device. Assuming the device is used for 20 seconds per measurement, twice per day, for five years, a VCSEL will accumulate approximately 20 hours of active use. Thus, a handheld SS-OCT device based on a VCSEL driven out of its rated operating range may continue to produce useful results for its entire intended operating life.

Example 3: OCT Signals for Varying Thicknesses

FIG. 16 shows oscilloscope signals for two different configurations of the optical setup of FIG. 14. The VCSEL had a central wavelength of approximately 850 nm and a rated range of emission wavelengths of approximately 1.8 nm. The VCSEL current was continuously swept in a triangular pattern with a maximum electric current of 15 mA. The current was swept at a frequency of 125 Hz. The VCSEL drive current (green) and the interference signal (purple) were recorded using an oscilloscope. Two glass cover slides of 150 µm thickness were placed at an arbitrary distance apart, referred to as the zero position. The zero position was chosen such that 2-3 periods were recorded from the interference signal resulting from light reflecting from the first glass cover slide and light reflecting from the second glass cover slide. Changes in the distance between the two glass coverslips produced changes in the frequency of oscillation of the interference signal. For instance, at the zero position, the interference signal varied with a frequency of approximately 950 Hz. After adding a 25.0 µm displacement from the zero position to the distance between the two coverslips, the interference signal varied with a frequency of approximately 1050 Hz.

Example 4: Extraction of Frequencies from Interference Signals

Figure 17:
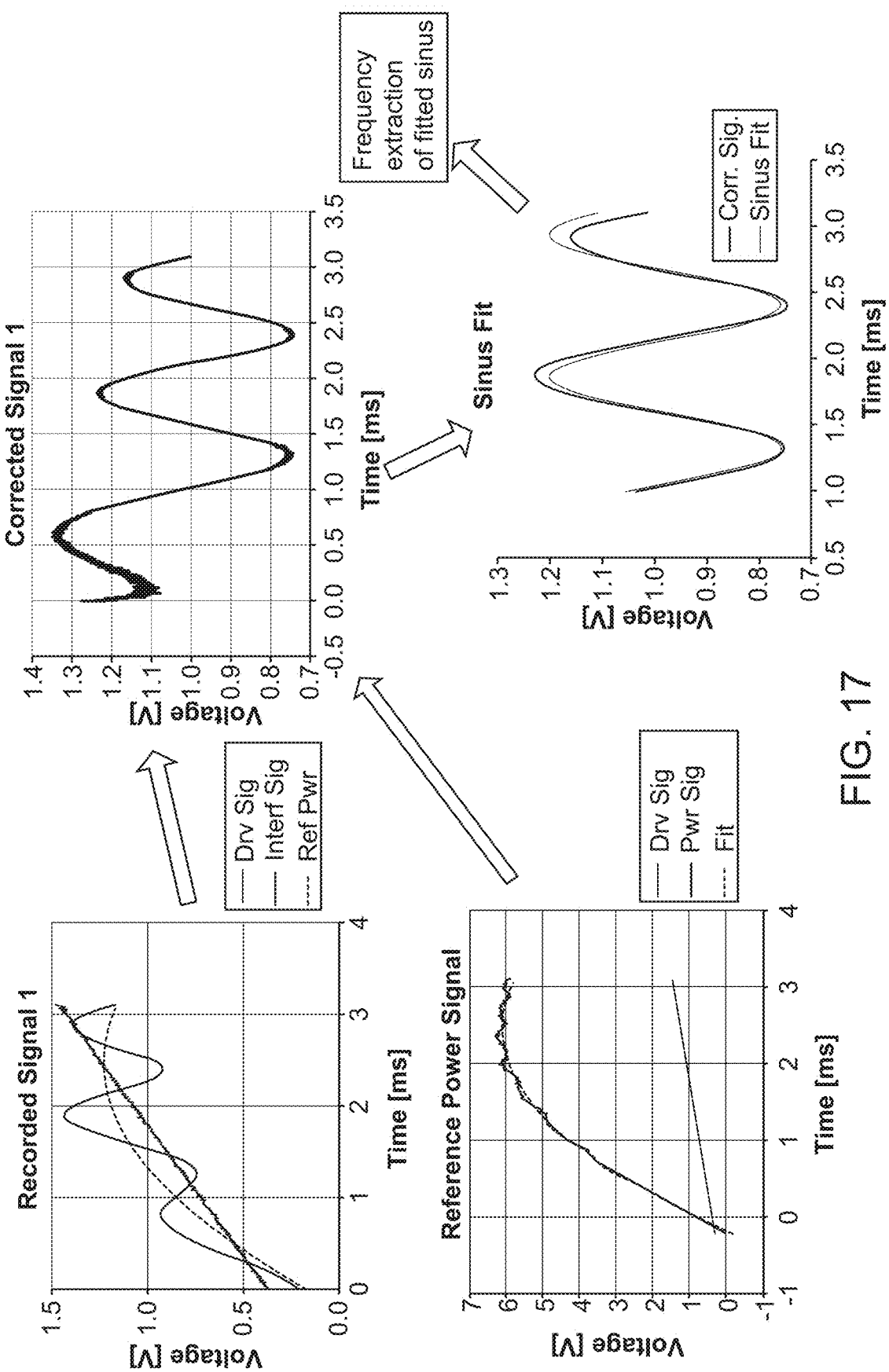
FIG. 17 shows a method of signal processing for extracting the frequency of oscillation of the interference signal generated using an SS-OCT system utilizing a single VCSEL and no reference arm.

FIG. 17 shows a method of signal processing for extracting the frequency of oscillation of the interference signal generated using an SS-OCT system utilizing a single VCSEL and no reference arm. The interference signal recorded on the oscilloscope is corrected by dividing the interference signal by the VCSEL optical power. This produces a slowly decaying sinusoid. The corrected data is then fit to a sinusoid using a non-linear least squares fitting procedure. The frequency of oscillation of the corrected interference signal is extracted from the non-linear least squares fit.

Example 5: Repeatability Measurements

Figure 18:
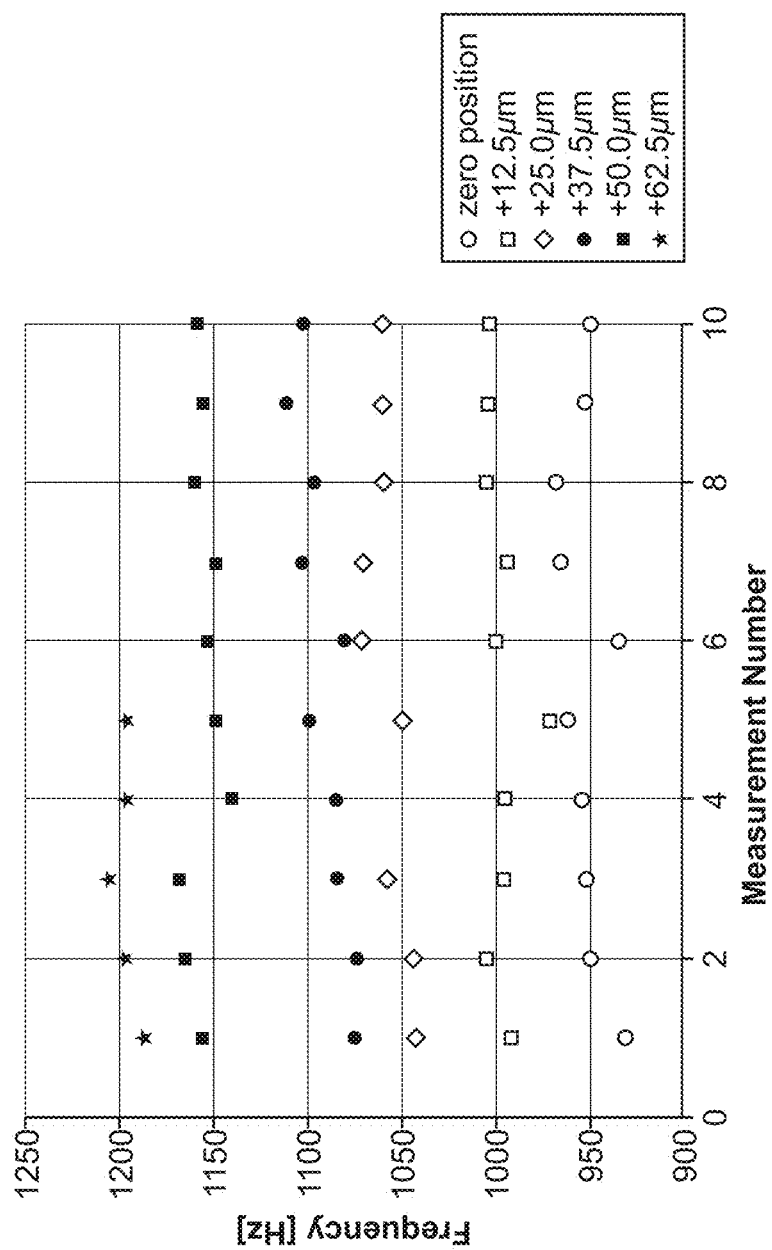
FIG. 18 shows the results of a study to determine the reproducibility of extracting the frequency of oscillation of the interference signal generated using an SS-OCT system utilizing a single VCSEL and no reference arm.

FIG. 18 shows the results of a study to determine the repeatability of extracting the frequency of oscillation of the interference signal generated using an SS-OCT system utilizing a single VCSEL and no reference arm. The distance between the two glass coverslips was varied in increments of 12.5 µm. The frequency of the sinusoidal fit was attained from the interference signal at each value of the distance between the two glass coverslips. The experiment was replicated 5 or 10 times for each value of the distance between the two glass coverslips.

Figure 19:
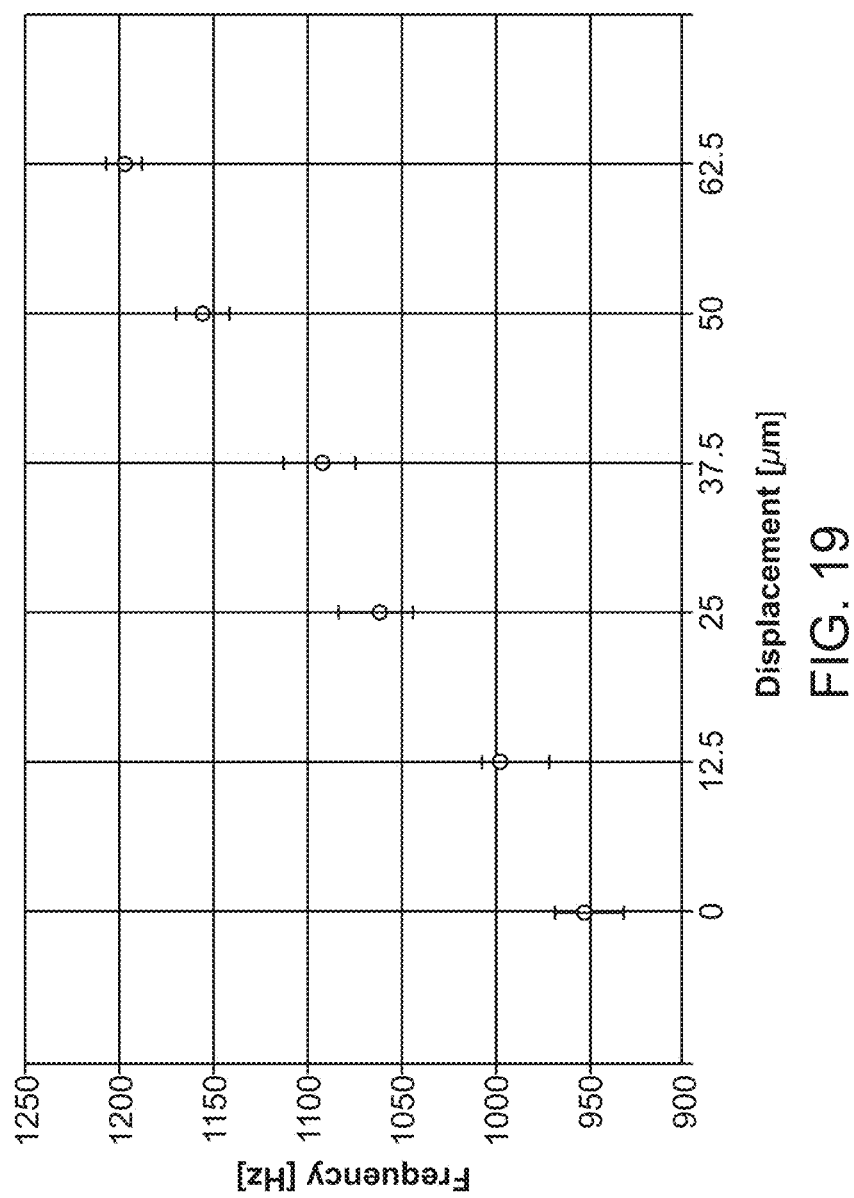
FIG. 19 shows the means and 95% confidence intervals of the frequencies obtained during the study to determine the reproducibility of extracting the frequency of oscillation of the interference signal generated using an SS-OCT system utilizing a single VCSEL and no reference arm.

FIG. 19 shows the means and 95% confidence intervals of the frequencies obtained during the study to determine the reproducibility of extracting the frequency of oscillation of the interference signal generated using an SS-OCT system utilizing a single VCSEL and no reference arm. With the exception of the 25 µm and 37.5 µm data points, each of the tested distances is separated from the other tested distances by more than two standard deviations from the distances 12.5 µm less than itself and 12.5 µm greater than itself. For all data points, each of the tested distances is separated from the other tested distances by more than two standard deviations from the distances 25.0 µm less than itself and 25.0 µm greater than itself. Thus, it can be surmised that this method for determining changes in the thickness of a layer (here, the air gap between two glass coverslips) has a limit of detection for changes in the thickness of a layer which is between 12.5 µm and 25.0 µm. This compares favorably with the operating requirements for a handheld SS-OCT system for measuring changes in the RT.

Example 6: Fundus Imaging

Figure 37A:
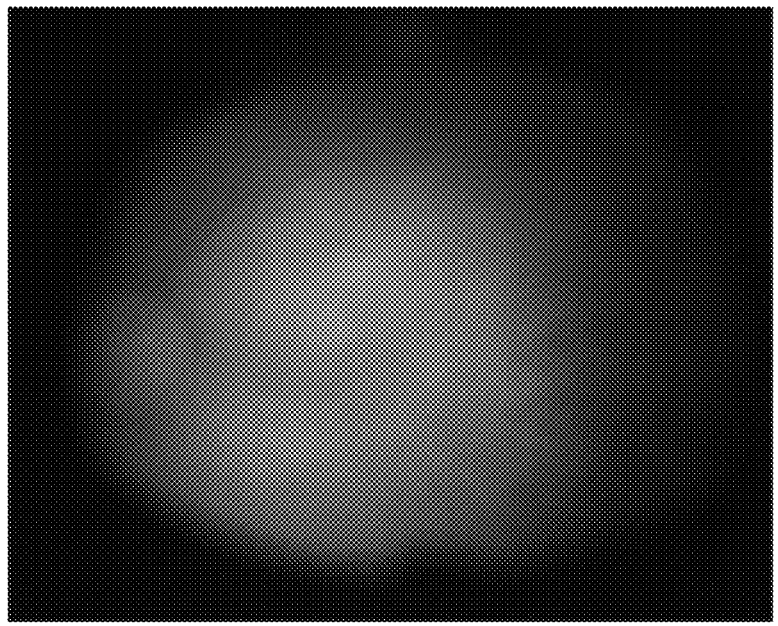
FIG. 37A, FIG. 37B, and FIG. 37C show exemplary fundus images obtained using the systems and methods described herein.
Figure 37B:
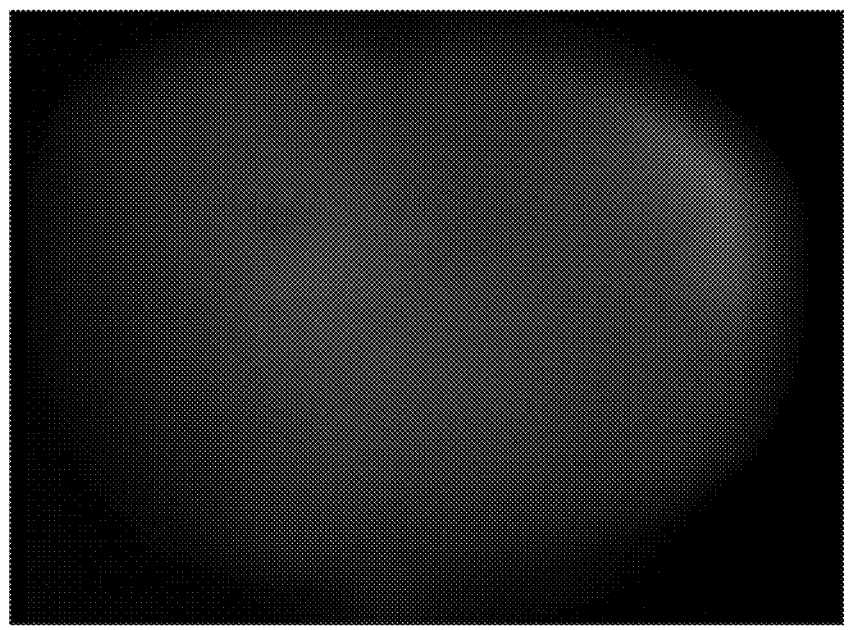
Figure 37C:
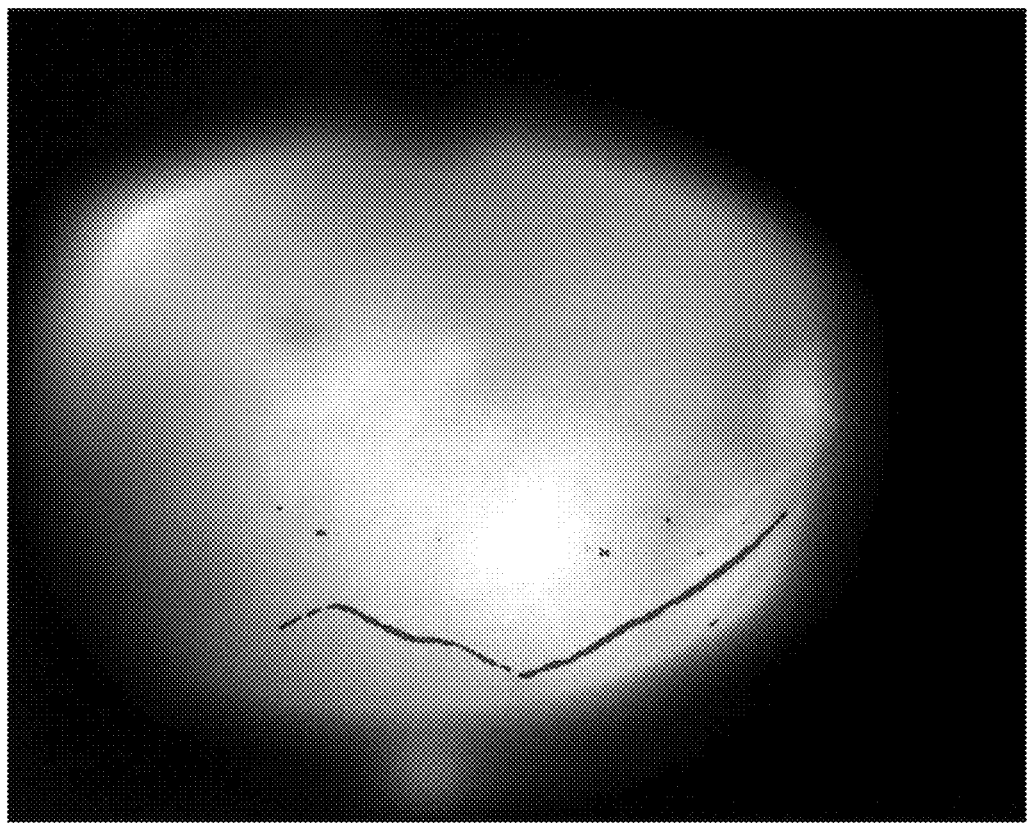

FIGS. 37A-C show exemplary fundus images obtained using the systems and methods described herein. FIG. 37A shows a fundus image with a relatively high contrast and a relatively high amount of observable structure. FIG. 37B shows a fundus image with a relatively low contrast and a relatively low amount of observable structure. FIG. 37C shows an enhanced fundus image subjected to the fundus recognition methods described herein. The fundus image in FIG. 37C was obtained by applying the fundus recognition methods described herein to the image of FIG. 37B (a fundus image with a relatively low contrast and a relatively low amount of observable structure). As shown in FIG. 37C, the vein of the fundus is clearly identified using the fundus recognition methods described herein. Thus, the fundus recognition methods are capable of detecting a location of a substructure of a fundus in a fundus image even when the fundus images are of relatively low quality. The substructure of the fundus may be used for image registration.

Example 7: Re-Sampling for Chirp Correction

Figure 38A:
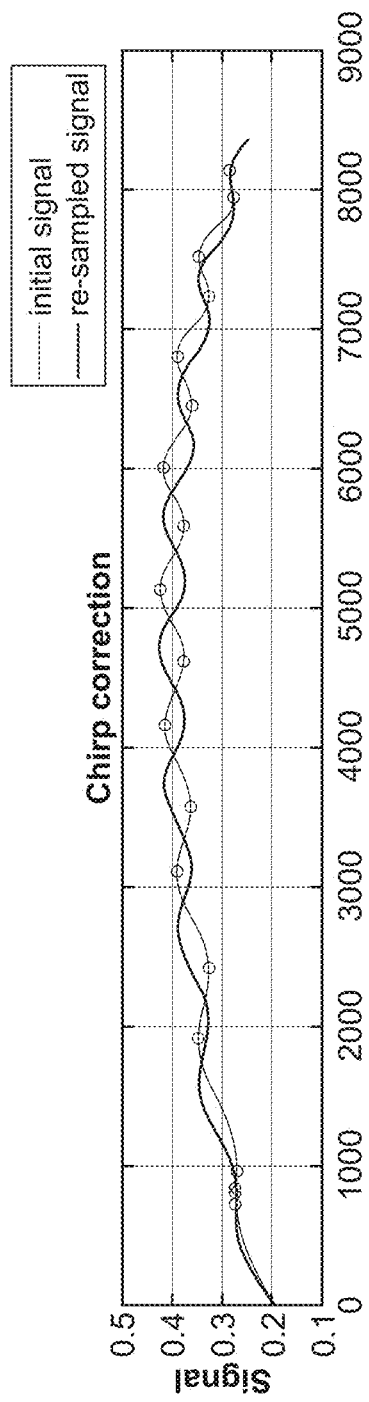
FIG. 38A, and FIG. 38B show the effects of re-sampling for chirp correction of a SS-OCT signal in the time domain.
Figure 38B:
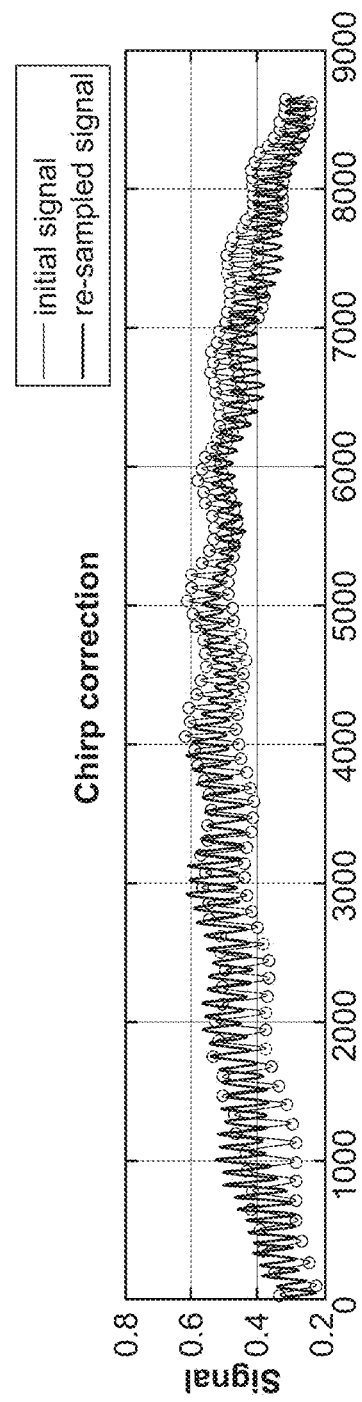

FIGS. 38A-B show the effects of re-sampling for chirp correction of a SS-OCT signal in the time domain. FIG. 38A shows the effects of re-sampling for chirp correction of a SS-OCT signal having a relatively low frequency. FIG. 38B shows the effects of re-sampling for chirp correction of a SS-OCT system having a relatively high frequency. The results of the re-sampling procedure are shown in the frequency domain in FIGS. 39A-C.

Example 8: Frequency Drift of Uncorrected and Chirp Corrected SS-OCT Signals

Figure 39A:
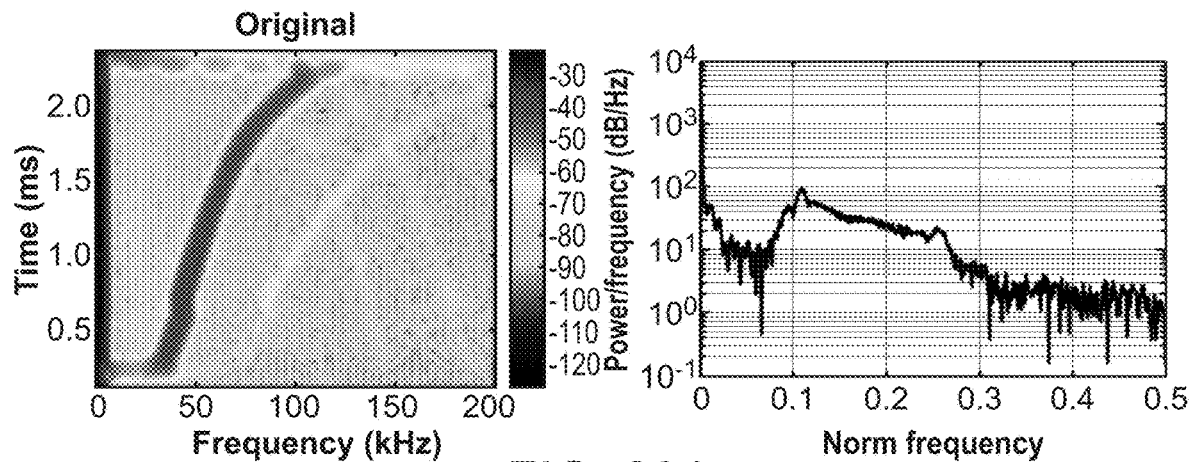
FIG. 39A, FIG. 39B, and FIG. 39C show the frequency drift of uncorrected and chirp corrected SS-OCT signals in the frequency domain.
Figure 39B:
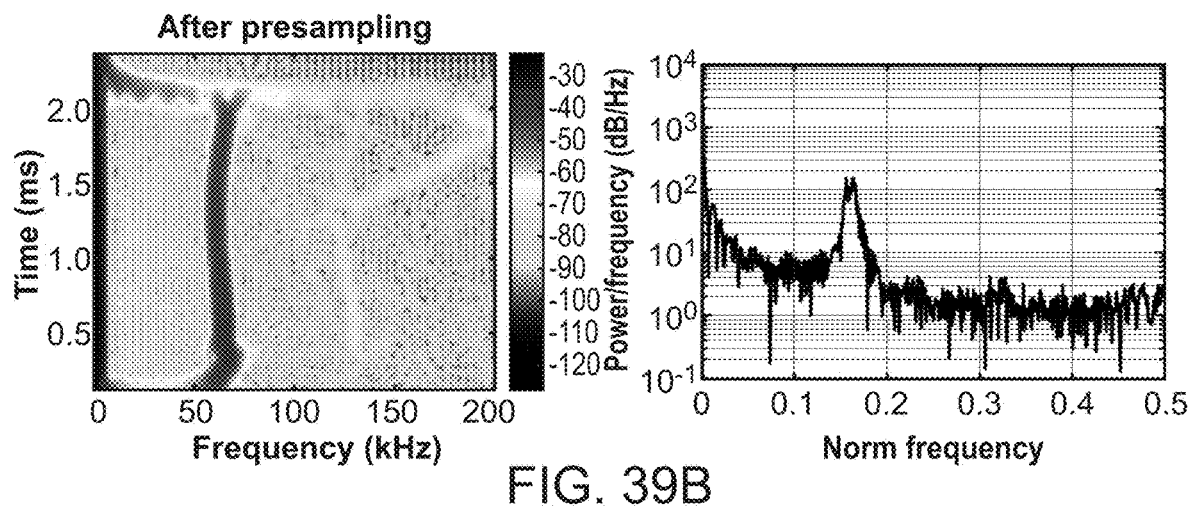
Figure 39C:
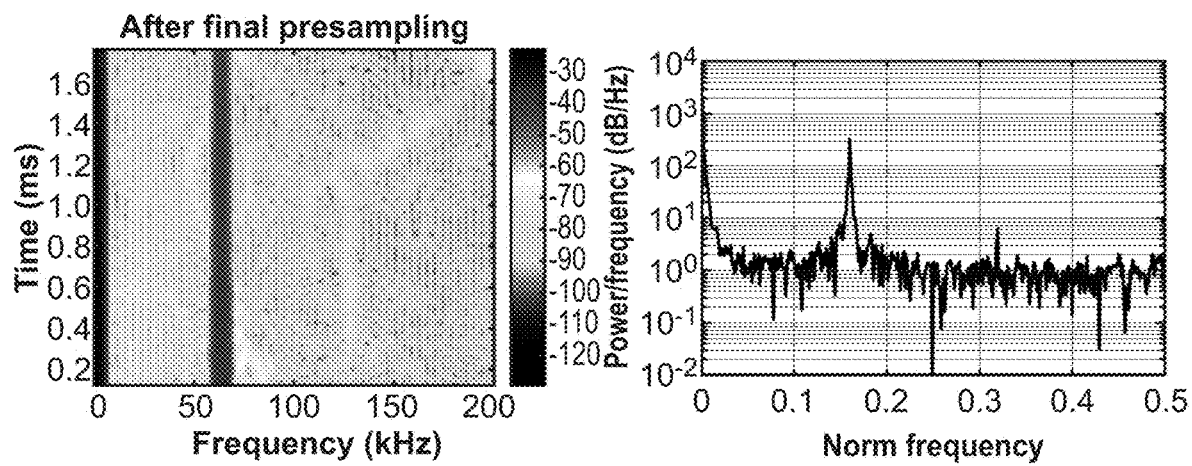

FIGS. 39A-C show the frequency drift of uncorrected and chirp corrected SS-OCT signals in the frequency domain. FIG. 39A shows frequency drift of a SS-OCT signal that has not been corrected by the re-sampling methods for chirp correction described herein. The uncorrected SS-OCT signal is subject to drift over more than 50 kHz over a period of about 2 seconds. FIG. 39B shows frequency drift of a SS-OCT signal that has been subjected to presampling for chirp correction. The signal shows significantly smaller frequency drift, varying by a few Hz over a period of about 2 seconds. FIG. 39C shows frequency drift of a SS-OCT signal that has been subjected to a final resampling for chirp correction. The signal shows still smaller frequency drift, varying by an imperceptible amount over a period of about 1.6 seconds. Thus, frequency drift may be corrected using chirp correction or resampling methods, as described herein. Reduction of the frequency drift using the re-sampling methods described herein results in a narrower measured frequency distribution, yielding more precise RT or RLT measurements with higher signal-to-noise ratios.

Example 9: Phase Drift Due to a Variety of Noise Sources

Figure 40A:
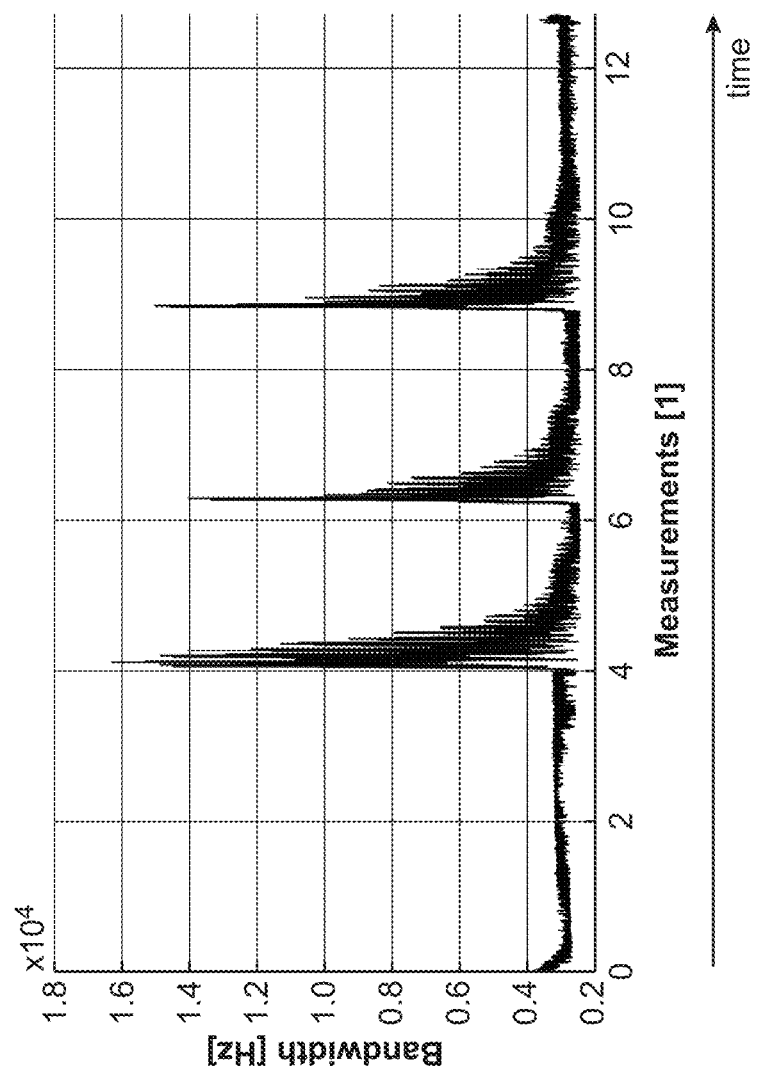
FIG. 40A, FIG. 40B, and FIG. 40C show exemplary phase drifts of uncorrected SS-OCT signals associated with a variety of sources of noise.
Figure 40B:
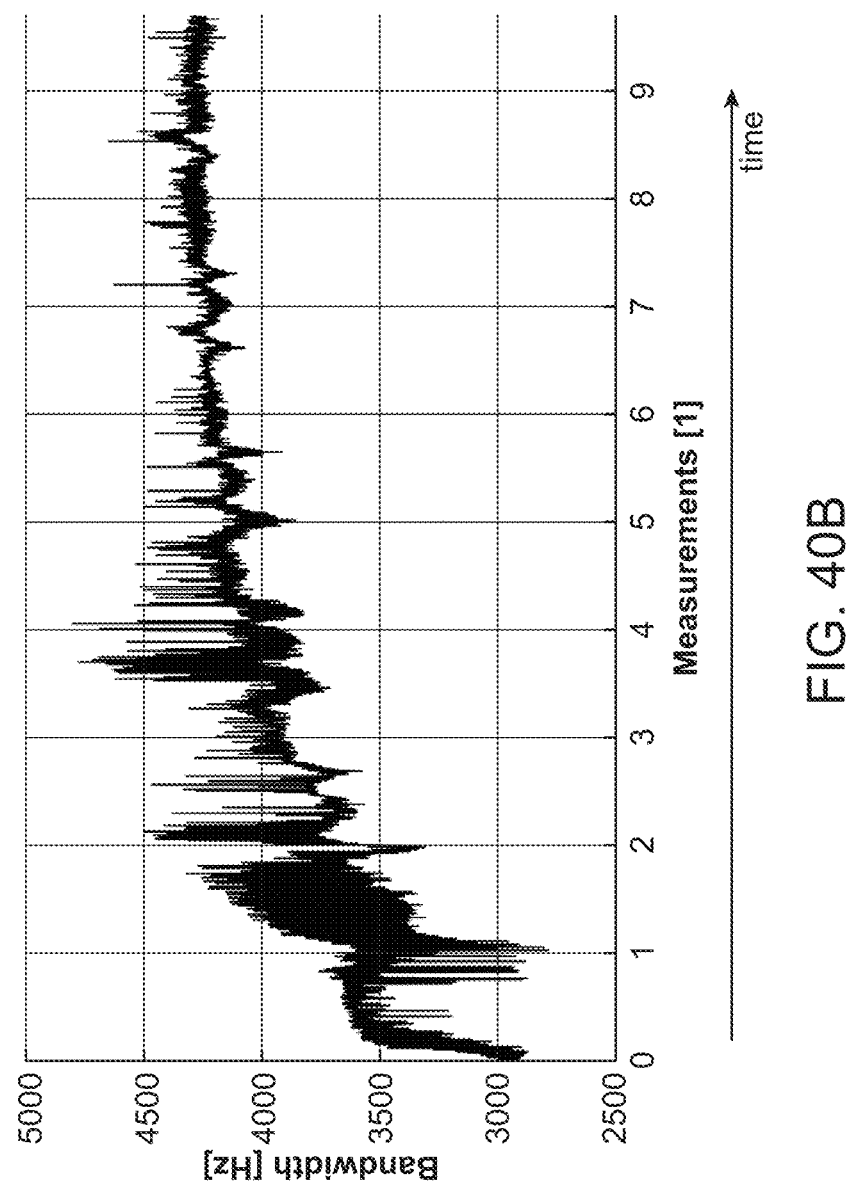
Figure 40C:
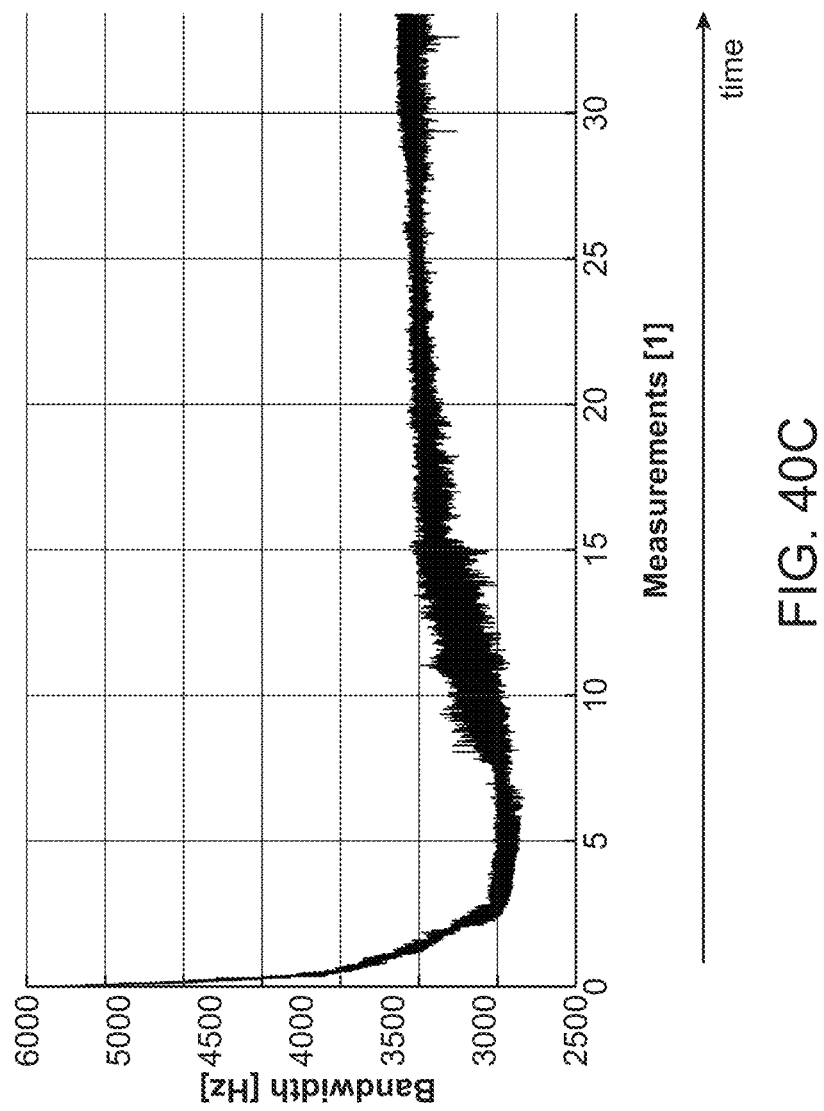

FIGS. 40A-C show exemplary phase drifts of uncorrected SS-OCT signals associated with a variety of sources of noise. FIG. 40A shows phase drift of an SS-OCT signal associated with noise resulting from vibrations. The large spikes in the bandwidth of the SS-OCT signal result from intentionally hitting the floor. FIG. 40B shows phase drift of an SS-OCT signal associated with noise resulting from varying spatial filtering of the light source. The bandwidth of the SS-OCT signal varies by up to 2 kHz over time. FIG. 40C shows phase drift of an SS-OCT signal associated with noise levels resulting from optimal conditions. After transient behavior, the SS-OCT signal settles to a relatively constant bandwidth when operation conditions are kept as constant as possible. Even in this ideal situation, the bandwidth of the SS-OCT signal still varies by up to 500 Hz over time. Thus, it can be seen that uncorrected SS-OCT signals may be subject to significant changes in bandwidth, even when operating at ideal conditions. The SS-OCT signals may be corrected to significantly reduce the variation in bandwidth over time using the resampling methods as described herein.

Example 10: Correction of Phase Shifts Associated with Patient Movement

Figure 41A:
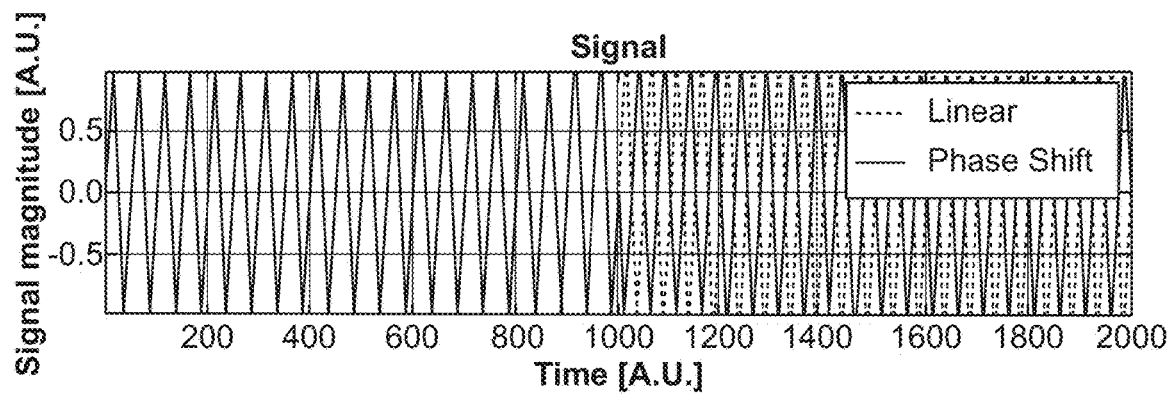
FIG. 41A, FIG. 41B, FIG. 41C, and FIG. 41D show simulations of phase shifts associated with patient movement.
Figure 41B:
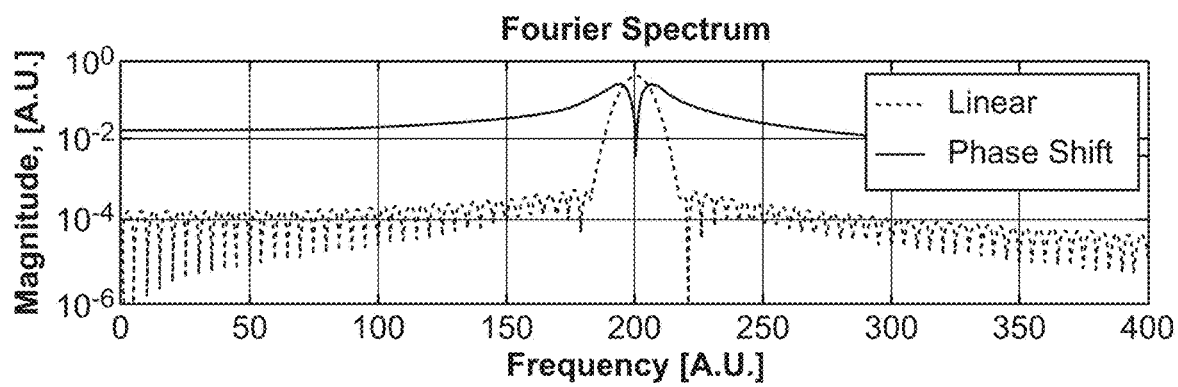
Figure 41C:
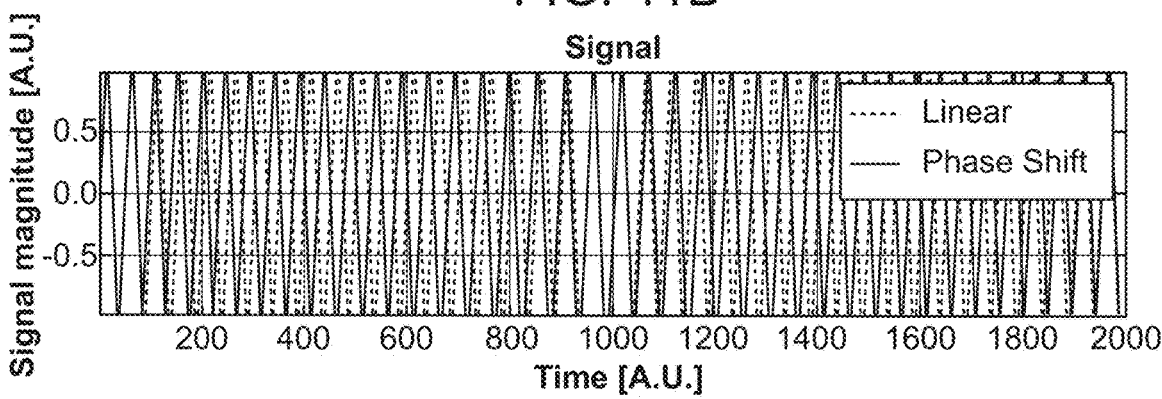
Figure 41D:
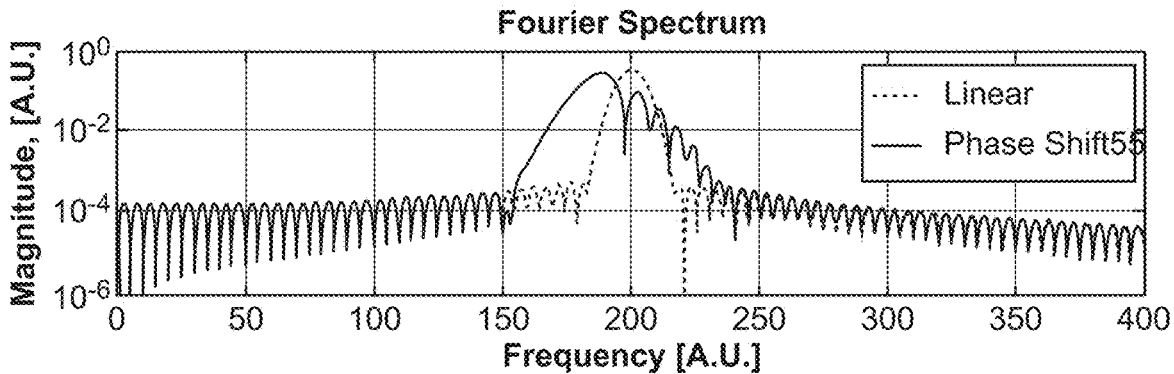

FIGS. 41A-D show simulations of phase shifts associated with patient movement. FIG. 41A shows a simulated signal subjected to a phase shift of t radians over a duration of half the signal length. FIG. 41A shows the frequency spectrum of a simulated signal subjected to a phase shift of t radians over a duration of half the signal length. A phase shift of t radians corresponds to a patient movement of approximately 225 nm for light having a wavelength of 850 nm. The phase shift imparts a significant error in the frequency spectrum. FIG. 41C shows a simulated signal subjected to a phase shift of t radians over a duration of a single cycle of the signal. FIG. 41D shows the frequency spectrum of a simulated signal subjected to a phase shift of t radians over a duration of a single cycle of the signal. Though present for only a brief amount of time, the phase shift still imparts a significant error in the frequency spectrum. These phase shifts may be corrected by utilizing fast A-scans or chirp correction methods, as described herein.

Figure 42A:
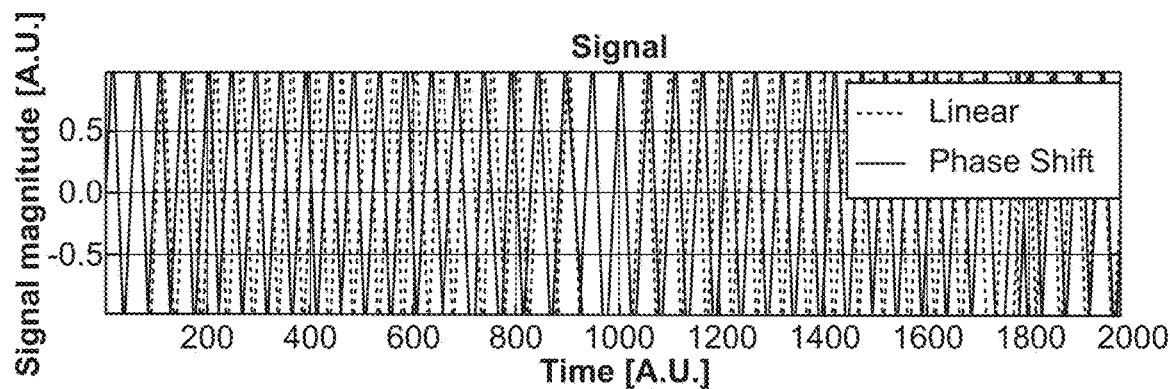
FIG. 42A, FIG. 42B, FIG. 42C, and FIG. 42D show simulations of the effect of A-scan time on the error arising from phase shifts associated with patient movement.
Figure 42B:
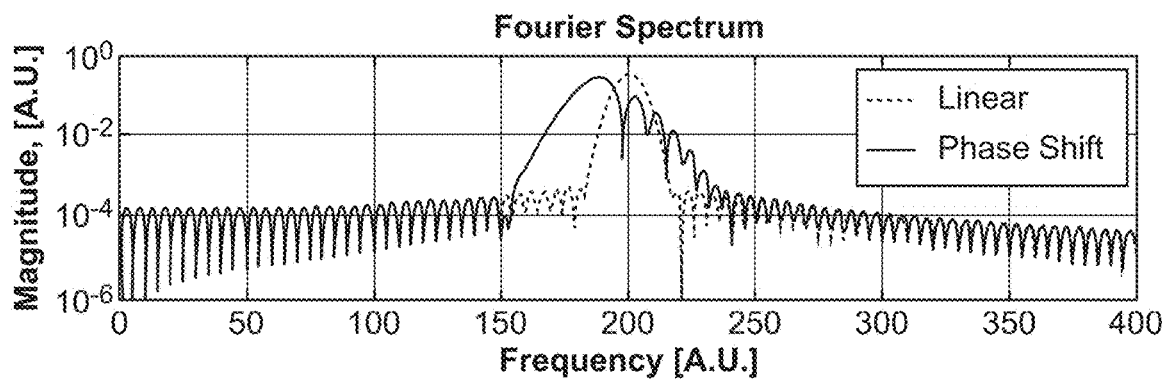
Figure 42C:
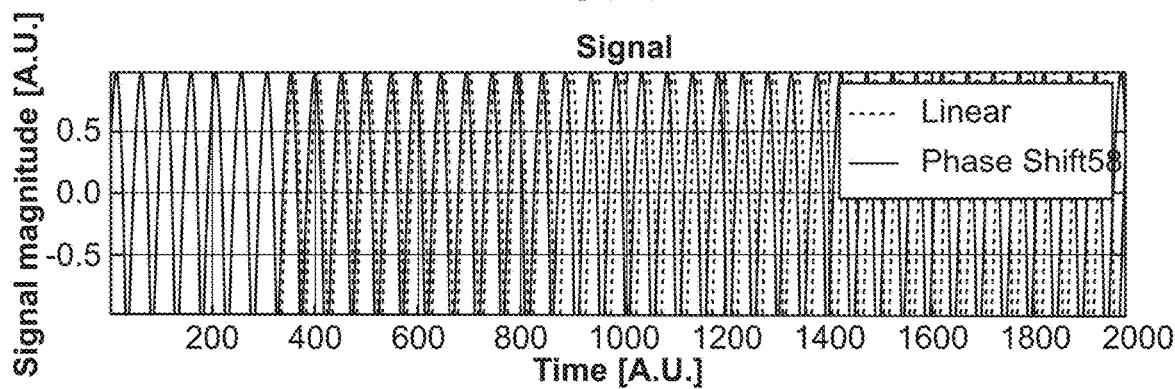
Figure 42D:
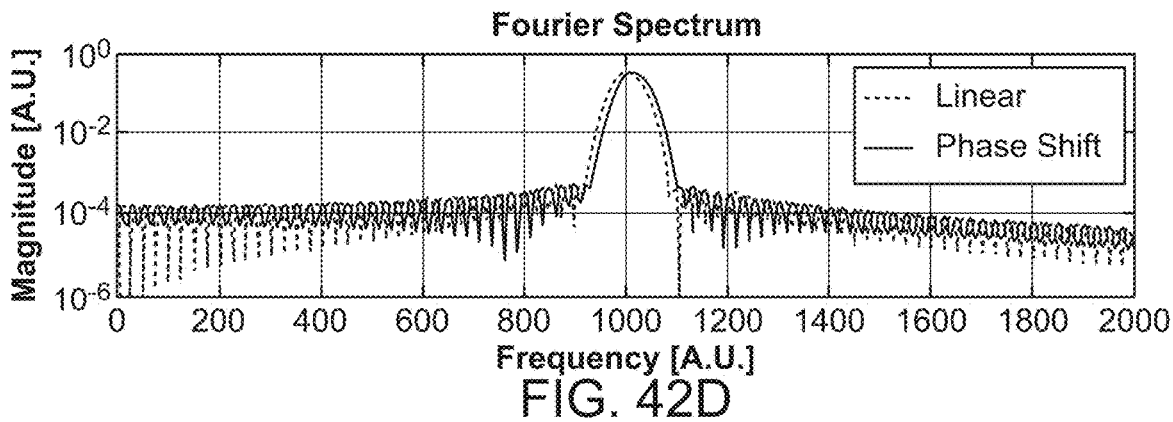

FIGS. 42A-D show simulations of the effect of A-scan time on the error arising from phase shifts associated with patient movement. FIG. 42A shows a simulated signal subjected to a phase shift of t radians over a duration of a single cycle of the signal with an A-scan duration of 2 ms. FIG. 42B shows the frequency spectrum of a simulated signal subjected to a phase shift of it radians over a duration of a single cycle of the signal with an A-scan duration of 2 ms. The phase shift imparts a significant error in the frequency spectrum for this relatively long A-scan duration. FIG. 42C shows a simulated signal subjected to a phase shift of t radians over a duration of a single cycle of the signal with an A-scan duration of 0.4 ms. FIG. 42D shows the frequency spectrum a simulated signal subjected to a phase shift of it radians over a duration of a single cycle of the signal with an A-scan duration of 0.4 ms. The phase shift imparts a significantly small error in the frequency spectrum for this relatively short A-scan duration. Thus, noise associated with patient movement may be decreased by utilizing fast A-scans, as described herein.

Example 11: Measurement of Typical Patient Movements

Figure 43A:
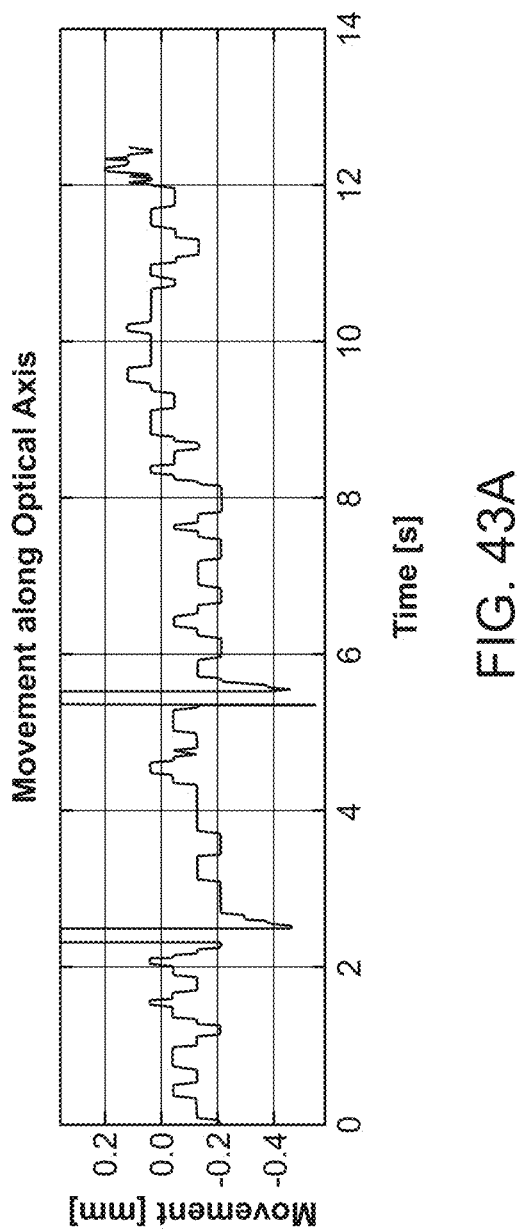
FIG. 43A, and FIG. 43B show the amplitude of typical patient movements.
Figure 43B:
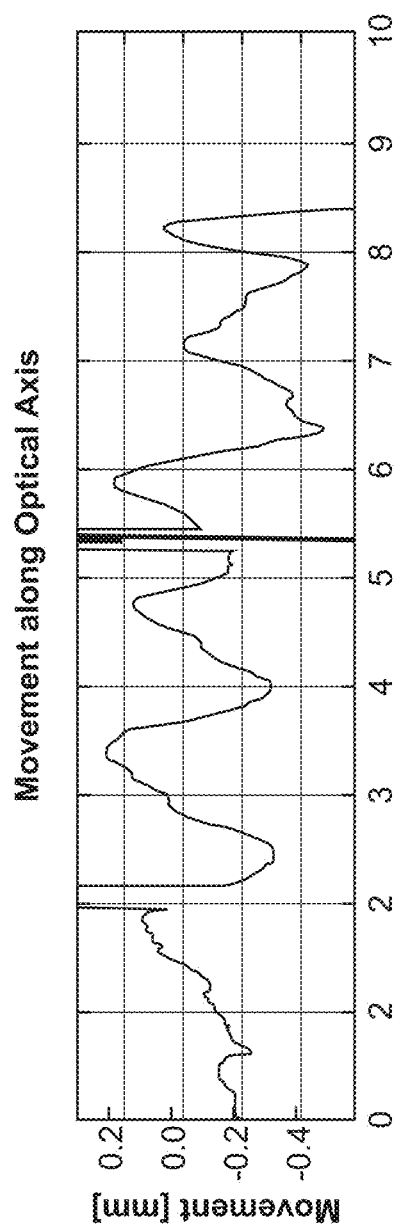

FIGS. 43A-B show the amplitude of typical patient movements. FIG. 43A shows movement along the optical axis for a patient maintaining himself as steady as possible. The large jumps between positions arise due to patient blinking. Ignoring blinking, a typical patient movement has an amplitude of about 0.25 mm and a duration of about 1.2 s, for a typical movement rate of 210 nm/ms. Such movement rates can be corrected for by using the fast A-scan methods described herein. A maximum patient movement has an amplitude of about 0.25 mm and a duration of about 0.16 s, for a maximum movement rate of 1,560 nm/ms. FIG. 43B shows movement along the optical axis for a patient who is intentionally moving. Ignoring blinking, a typical intentional patient movement has an amplitude of about 2.19 mm and a duration of about 0.76 s, for a typical intentional movement rate of 2,900 nm/ms.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A compact optical coherence tomography (OCT) system to measure a thickness of a retina, the compact OCT system comprising:
   a detector;
   a light source configured to generate a light beam comprising a plurality of wavelengths;
   a plurality of optical elements coupled to the light source to direct the beam into the eye and generate an interference signal at the detector; and
   circuitry coupled to the detector and the light source to determine the retinal thickness in response to the signal,
   wherein the compact OCT system measures a change in retinal thickness at a precision less than an axial resolution of the compact OCT system, the change in retinal thickness comprising a first thickness at a first time and a second thickness at a second time,
   wherein the light source comprises a vertical cavity surface emitting laser (VCSEL) configured to vary an emission wavelength of the light beam over a range from about 5 to 10 nm.

2. The compact OCT system of claim 1, wherein a change in retinal thickness measured with the compact OCT system is less than an axial resolution of the compact OCT system.

3. The compact OCT system of claim 1, wherein the axial resolution comprises a resolution value within a range from about 150 µm to about 30 µm.

4. The compact OCT system of claim 1, wherein the circuitry is configured to vary the wavelength with a drive current from the circuitry.

5. The compact OCT system of claim 1, wherein the retinal thickness comprises a distance between a first layer of the retina and a second layer of the retina and the retinal thickness is more than 150 µm.

6. The compact OCT system of claim 1, wherein the thickness of the retina is within a range from about 150 to 300 µm, and the OCT system comprises an axial resolution within a range from about 150 µm to about 30 µm.

7. The compact OCT system of claim 1, wherein the thickness is measured faster than characteristic frequencies of movement of the compact OCT system in relation to the eye, and wherein the movement is selected from the group consisting of movement related to the patient holding the OCT system in his hand, eye movement, and tremor.

8. The compact OCT system of claim 1, further comprising a viewing target for the patient to align the light beam with a fovea of the eye and wherein the viewing target comprises one or more of the light beam or light from a light emitting diode.

9. The compact OCT system of claim 1, wherein the VCSEL has a specified maximum rated range of wavelength variation.

10. The compact OCT system of claim 9, wherein the circuitry is configured to drive the VCSEL beyond the specified maximum range of wavelength variation by at least about 1 nm.

11. The compact OCT system of claim 1, wherein the circuitry is configured to cause an emitted wavelength to sweep over a range of wavelengths with a sweeping frequency and the circuitry is configured to determine the thickness in response to frequencies of the interference signal.

12. The compact OCT system of claim 11, wherein the sweeping frequency is faster than an ocular tremor of a user, or a hand tremor of the user.

13. The compact OCT system of claim 1, wherein the circuitry is configured to heat the light source to change the wavelength.

14. The compact OCT system of claim 1, wherein the plurality of optical elements is arranged to provide a reference optical path and a measurement optical path and the interference signal results from interference of light along the reference optical path and the measurement optical path.

15. The compact OCT system of claim 1, wherein the plurality of optical elements is arranged to provide a measurement optical path and the interference signal results from interference of light from layers of the retina along the measurement optical path.

16. The compact OCT system of claim 1, wherein the circuitry comprises a processor configured to transform the interference signal into an intensity profile of light reflected along an optical path of the beam directed into the eye and to determine the thickness of the retina in response to the intensity profile.

17. The compact OCT system of claim 16, wherein the intensity profile comprises a plurality of reflected peaks and the processor is configured with instructions to determine the thickness in response to the plurality of reflected peaks.

18. The compact OCT system of claim 17, wherein the processor is configured with instructions to determine the intensity profile in response to frequencies of the interference signal.

19. The compact OCT system of claim 16, wherein frequencies of the interference signal correspond to separation distances of layers of the retina and a rate of change of the wavelength of the light source.

20. The compact OCT system of claim 16, wherein frequencies of the interference signal correspond to separation distances of layers of the retina and a rate of change of a wavelength of the beam emitted from the light source.

21. The compact OCT system of claim 1, further comprising a viewing target to align the tomography system with a fovea of the eye and wherein the viewing target comprises one or more of the light beam, a target defined with a light emitting diode, or a VCSEL.

22. The compact OCT system of claim 1, further comprising housing to support the light source, the optical elements, the detector, and the circuitry, and wherein the housing is configured to be held in a hand of a user in front of the eye in order to direct the light beam into the eye.

23. The compact OCT system of claim 22, further comprising a sensor to measure which eye is measured in response to an orientation of the housing.

* * * * *